US010934280B2

United States Patent
Coates et al.

(10) Patent No.: US 10,934,280 B2
(45) Date of Patent: Mar. 2, 2021

(54) CONDENSED THIOPHENE DERIVATIVES USEFUL AS NAPI-IIB INHIBITORS

(71) Applicant: Eli Lilly and Company, Indianapolis, IN (US)

(72) Inventors: David Andrew Coates, New Palestine, IN (US); Kevin Robert Fales, Avon, IN (US); Jeffrey Allen Peterson, Carmel, IN (US); Jeffrey Michael Schkeryantz, Fishers, IN (US); Quanrong ' Shen, Fishers, IN (US); Matthew John Valli, Zionsville, IN (US); John Rowley Wetterau, II, Indianapolis, IN (US); Dariusz Stanislaw Wodka, Zionsville, IN (US); Yanping Xu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/321,575

(22) PCT Filed: Aug. 8, 2017

(86) PCT No.: PCT/US2017/045843
§ 371 (c)(1),
(2) Date: Jan. 29, 2019

(87) PCT Pub. No.: WO2018/034883
PCT Pub. Date: Feb. 22, 2018

(65) Prior Publication Data
US 2020/0031813 A1    Jan. 30, 2020

Related U.S. Application Data

(60) Provisional application No. 62/375,169, filed on Aug. 15, 2016.

(51) Int. Cl.
*C07D 409/12* (2006.01)
*C07D 487/08* (2006.01)
*A61K 47/32* (2006.01)

(52) U.S. Cl.
CPC ............ *C07D 409/12* (2013.01); *A61K 47/32* (2013.01); *C07D 487/08* (2013.01)

(58) Field of Classification Search
CPC ..... C07D 409/12; C07D 487/08; A61K 47/32
See application file for complete search history.

(56) References Cited

U.S. PATENT DOCUMENTS
2013/0053369 A1   2/2013   Hachiya et al.

FOREIGN PATENT DOCUMENTS

| EP | 20142772490 | 9/2014 | |
| WO | 2014003153 | 1/2014 | |
| WO | 2016026372 | 2/2016 | |
| WO | WO 2016/026372 | * 2/2016 | ........... C07D 333/70 |

OTHER PUBLICATIONS

International Search Report of the International Searching Authority pertaining to International Application No. PCT/US2017/045843; dated Sep. 25, 2017; 5 pages.
Written Opinion of the International Searching Authority pertaining to International Application No. PCT/US2017/045843; dated Sep. 25, 2017; 5 pages.

* cited by examiner

*Primary Examiner* — Erich A Leeser
(74) *Attorney, Agent, or Firm* — Macharri R Vorndran-Jones

(57) ABSTRACT

The invention provides compounds of the formula: (A), pharmaceutically acceptable salts, pharmaceutical compositions thereof and methods of using these compounds, salts, or compositions to treat hyperphosphatemia, chronic kidney disease, and/or the cardiovascular disease associated with chronic kidney disease.

(A)

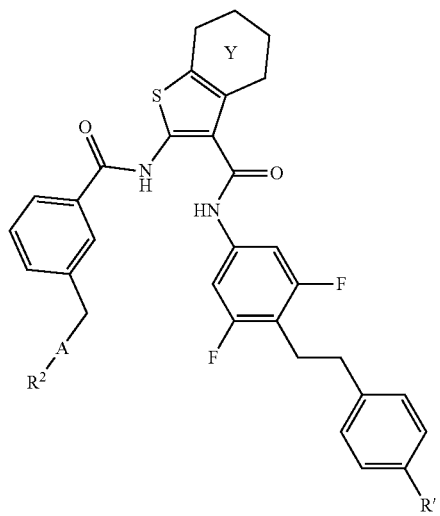

21 Claims, No Drawings

CONDENSED THIOPHENE DERIVATIVES USEFUL AS NAPI-IIB INHIBITORS

The invention provides compounds to treat the phosphate excess or hyperphosphatemia associated with chronic kidney disease (CKD), dialysis patients with end stage renal disease (ESRD), and related cardiovascular disease.

In patients with impaired renal function, such as chronic kidney disease and dialysis patients with end stage renal disease, phosphorus accumulates in the body resulting in a rise in phosphorus concentration in the blood and a phosphate excess.

In some patients this phosphate burden reaches a state referred to as hyperphosphatemia. The elevated phosphate burden in CKD and ESRD in turn brings about the hypersecretion of parathyroid hormones, i.e., secondary hyperparathyroidism, and causes bone lesions. Hyperphosphatemia has been linked with calcification of the coronary arteries and aorta, as well as cardiovascular and all-cause mortality. Vascular calcification is considered to promote dysfunction of the heart leading to death. Dysfunction of phosphate regulation has serious clinical consequences, and studies show that even small increases in serum phosphate levels, within the normal or near-normal range, may correlate with increased morbidity and mortality. Phosphate excess in CKD stage three and four patients, and the body's compensating response to the phosphate excess, has been implicated in the associated cardiovascular morbidity and mortality. Decreasing phosphate absorption in CKD stage three and four patients may mitigate or prevent these responses and preserve cardiovascular health. Controlling phosphate load early in CKD may mitigate or prevent morbidity and mortality in affected patients (C. S. Ritter and E. Slatopolsky, Phosphate Toxicity in CKD: The Killer Among Us, Clin. J. Am. Soc. Nephrol. 11:1088-1100, 2016).

Three isoforms of NaPi-II have been identified. NaPi-IIa (type IIa, also referred to as SLC34A1) is mainly expressed in the kidney, while NaPi-IIb (type IIb, also referred to as SLC34A2) is expressed in the small intestine and can be regulated by vitamin D. NaPi-IIc (type IIc, also referred to as SLC34A3) is also expressed in the kidney. Phosphate absorption in the gastrointestinal tract is performed in large part by NaPi-IIb, whereas phosphate in the blood is filtered by renal glomeruli and reabsorbed in necessary amounts mainly by NaPi-IIa and NaPi-IIc in the renal tubule (Miyamoto, et al. *Sodium-Dependent Phosphate Cotransporters: Lessons from Gene Knockout and Mutation Studies*, J. Pharm. Science, 100(9):3719-30, 2011).

In spite of progress made for treatment of phosphate excess, and/or hyperphosphatemia, there remains a significant unmet need for safe and effective therapies to treat these conditions. Current treatments employ phosphate adsorbents to suppress phosphate absorption in the gastrointestinal tract. These include for example nonmetallic polymer adsorbents, for example sevelamer carbonate and sevelamer hydrochloride, calcium salt preparations, for example precipitated calcium carbonate, and metallic adsorbents, for example lanthanum carbonate. However, these agents have each been reported to have adverse effects such as constipation, diarrhea, hypercalcemia, and metal accumulation. In addition, treatment with adsorbents requires daily intake on the order of a few grams of adsorbent, and noncompliance with therapy is a common problem. Accordingly, there remains an unmet need for treatment of phosphate excess, and/or hyperphosphatemia, which provide improved safety, efficacy, and convenience.

Inhibition of NaPi-IIb may suppress phosphate absorption in the gastrointestinal tract resulting in decreased phosphate concentration in blood as an approach to treat hyperphosphatemia (Sabbagh et al, *Intestinal Phosphate Transport*, Adv. Chronic Kidney Dis., 18(2):85-90, 2011). Suppression of phosphate absorption by NaPi-IIb inhibition employs a different mechanism of action, as compared to current phosphate adsorbents, and may provide clinically useful advantages for prevention and or treatment of phosphate excess and/or hyperphosphatemia. Further, NaPi-IIb transporter inhibitors may provide additional benefits for secondary hyperparathyroidism, chronic kidney disease, and/or cardiovascular disease associated with chronic kidney disease more generally, by decreasing the absorption of dietary phosphate.

The compounds of the present invention are inhibitors of NaPi-IIb transporter and demonstrate potent inhibition of NaPi-IIb. As such, compounds of the present invention are believed to be useful for the treatment of conditions in which NaPi-IIb mediated phosphate absorption plays a role, such as chronic kidney disease and hyperphosphatemia.

United States Application Publication US 2013/0053369 discloses certain tetrahydrobenzothiophene compounds as inhibitors of NaPi-IIb, and recites the compounds as useful in treating a number of diseases including hyperphosphatemia.

The need for a safe and convenient treatment of phosphate excess, hyperphosphatemia, chronic kidney disease, and/or cardiovascular disease associated with chronic kidney disease, without the disadvantages possessed by adsorbents, or other agents known in the field, continues to be a concern for treatment of patients renal disease. The present invention provides alternative compounds which are useful in treatment of phosphate excess, hyperphosphatemia, chronic kidney disease, and/or cardiovascular disease associated with chronic kidney disease. In addition, the compounds provided address the need for treatments of conditions associated with NaPi-IIb activity with improved efficacy and/or advantageous side effect and tolerability profiles.

The present invention provides a compound of the formula:

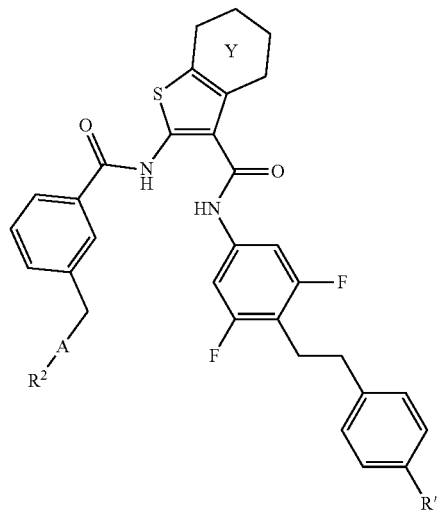

Formula II wherein Y is a fused cyclohexane ring or a fused phenyl ring, wherein A is

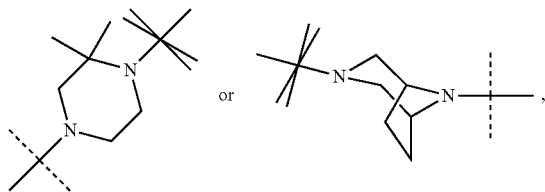

wherein the crossed lines indicate bonds for the point of attachment to the core of Formula II, and the dashed lines indicate bonds for the point of attachment to $R^2$,
wherein $R^2$ is selected from the group consisting of
—$CH_3$, —$(CH_2)_3OH$, —$(CH_2)_3OCH_3$, —$(CH_2)_3CO_2H$, —$COOCH_3$, —$COCH_3$, —$CO(CH_2)_3CH_3$, —$COCH(CH_3)_2$, —$CO(CH_2)_2CO_2H$, —$COCH_2NH_2$, —$COCH_2N(CH_3)_2$, —$SO_2N[(CH_2)_2OCH_3]_2$, —$SO_2NHCH_3$, —$SO_2(CH_2)_2OCH_3$, —$CONH(CH_2)_4OH$, —$CONH(CH_2)_4OCH_3$, —$CONHCH_3$, —$CONH(CH_2)_2CO_2H$, —$CONH(CH_2)_2OCH_3$, —$CON(CH_2CH_2OCH_3)_2$, —$CSNHCH_3$,

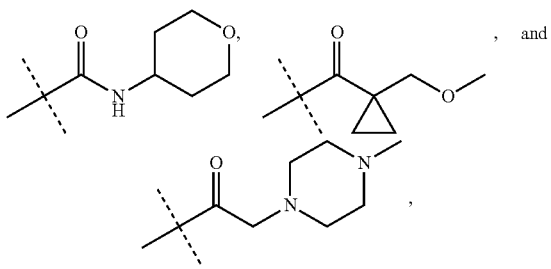

wherein the dashed lines represent the point of attachment, wherein R' is —$CO_2H$ or —$CONH_2$,
or a pharmaceutically acceptable salt thereof.

The present invention further provides a compound of Formula II as described above wherein Y is a fused cyclohexane ring, A is

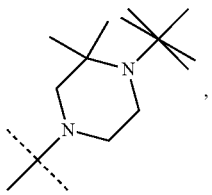

and R' is —$CO_2H$, or a pharmaceutically acceptable salt thereof.

The present invention further provides a compound of Formula II as described above wherein Y is a fused cyclohexane ring, A is

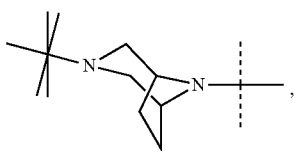

and R' is —$CO_2H$, or a pharmaceutically acceptable salt thereof.

Further, the present invention provides a compound of the formula:

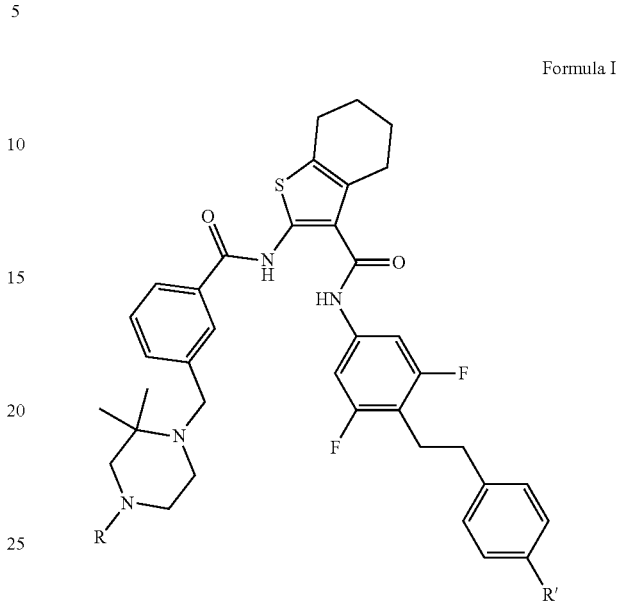

Formula I wherein R is selected from the group consisting of —$(CH_2)_3OH$, —$(CH_2)_3OCH_3$, —$(CH_2)_3CO_2H$, —$CONH(CH_2)_4OH$, —$COCH_2NH_2$, —$SO_2N[(CH_2)_2OCH_3]_2$, —$CONH(CH_2)_4OCH_3$, and —$CO(CH_2)_2CO_2H$,
wherein R' is —$CO_2H$ or —$CONH_2$,
or a pharmaceutically acceptable salt thereof.

The present invention further provides a compound of Formula I as described above wherein R' is —$CO_2H$, or a pharmaceutically acceptable salt thereof.

The following particular embodiments are compounds and/or salts of Formula I and/or II.

The present invention provides a compound which is 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, or a pharmaceutically acceptable salt thereof.

The present invention provides a compound which is 4-[2-[2,6-difluoro-4-[[2-[[3-[[4-(3-hydroxypropyl)-2,2-dimethyl-piperazin-1-yl]methyl]benzoyl]amino]-4,5,6,7-tetrahydrobenzothiophene-3-carbonyl]amino]phenyl]ethyl]benzoic acid, or a pharmaceutically acceptable salt thereof.

The present invention provides a compound which is 4-[2-[4-[[2-[[3-[[4-[bis(2-methoxyethyl)sulfamoyl]-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic acid, or a pharmaceutically acceptable salt thereof.

The present invention provides a compound which is 4-[2-[4-[[2-[[3-[[4-(3-carboxypropyl)-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic acid, or a pharmaceutically acceptable salt thereof.

The present invention provides a compound which is 4-[2-[2,6-difluoro-4-[[2-[[3-[[4-(3-methoxypropyl)-2,2-dimethyl-piperazin-1-yl]methyl]benzoyl]amino]-4,5,6,7-tetrahydrobenzothiophene-3-carbonyl]amino]phenyl]ethyl]benzoic acid, or a pharmaceutically acceptable salt thereof.

The present invention provides a compound which is 4-[2-[4-[[2-[[3-[[4-(2-aminoacetyl)-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic acid, or a pharmaceutically acceptable salt thereof.

The present invention provides a compound which is 4-[2-[2,6-difluoro-4-[[2-[[3-[[4-(4-methoxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, or a pharmaceutically acceptable salt thereof.

The present invention provides a compound which is 4-[4-[[3-[[3-[[4-[2-(4-carbamoylphenyl)ethyl]-3,5-difluoro-phenyl]carbamoyl]-4,5,6,7-tetrahydrobenzothiophen-2-yl]carbamoyl]phenyl]methyl]-3,3-dimethyl-piperazin-1-yl]-4-oxo-butanoic acid, or a pharmaceutically acceptable salt thereof.

The present invention provides a salt which is 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium.

The present invention provides a solid dispersion formulation of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium, wherein the formulation comprises 30% 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium, and 70% polyvinylpyrrolidone-vinyl acetate.

The present invention further provides a compound, or a pharmaceutically acceptable salt thereof, selected from the group consisting of:

4-[2-[2,6-difluoro-4-[[2-[[3-[(2,2,4-trimethylpiperazin-1-yl)methyl]benzoyl]amino]-4,5,6,7-tetrahydrobenzothiophene-3-carbonyl]amino]phenyl]ethyl]benzoic acid formic acid salt;

4-[2-[4-[[2-[[3-[[2,2-dimethyl-4-(methylcarbamoyl)piperazin-1-yl]methyl]benzoyl]amino]-4,5,6,7-tetrahydrobenzothiophene-3-carbonyl]amino]-2,6-difluoro-phenyl]ethyl]benzoic acid;

4-[2-[4-[[2-[[3-[[2,2-dimethyl-4-(methylcarbamothioyl)piperazin-1-yl]methyl]benzoyl]amino]-4,5,6,7-tetrahydrobenzothiophene-3-carbonyl]amino]-2,6-difluoro-phenyl]ethyl]benzoic acid;

4-[2-[4-[[2-[[3-[[4-(2-carboxyethylcarbamoyl)-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic acid;

4-[2-[2,6-difluoro-4-[[2-[[3-[[8-(methylcarbamoyl)-3,8-diazabicyclo[3.2.1]octan-3-yl]methyl]benzoyl]amino]benzothiophene-3-carbonyl]amino]phenyl]ethyl]benzoic acid, formic acid salt;

4-[2-[2,6-difluoro-4-[[2-[[3-[(4-methoxycarbonyl-2,2-dimethyl-piperazin-1-yl)methyl]benzoyl]amino]-4,5,6,7-tetrahydrobenzothiophene-3-carbonyl]amino]phenyl]ethyl]benzoic acid;

4-(2,6-difluoro-4-(2-(3-(((1R,5S)-8-pentanoyl-3,8-diazabicyclo[3.2.1]octan-3-yl)methyl)benzamido)-4,5,6,7-tetrahydrobenzo[b]thiophene-3-carboxamido)phenethyl)benzoic acid;

4-[2-[4-[[2-[[3-[[2,2-dimethyl-4-(methyl sulfamoyl)piperazin-1-yl]methyl]benzoyl]amino]-4,5,6,7-tetrahydrobenzothiophene-3-carbonyl]amino]-2,6-difluoro-phenyl]ethyl]benzoic acid;

4-[2-[2,6-difluoro-4-[[2-[[3-[[8-(tetrahydropyran-4-ylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoic acid;

4-[2-[4-[[2-[[3-[(8-acetyl-3,8-diazabicyclo[3.2.1]octan-3-yl)methyl]benzoyl]amino]-4,5,6,7-tetrahydrobenzothiophene-3-carbonyl]amino]-2,6-difluoro-phenyl]ethyl]benzoate;

4-[2-[2,6-difluoro-4-[[2-[[3-[[8-(2-methoxyethyl sulfonyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate;

4-[2-[2,6-difluoro-4-[[2-[[3-[[8-(2-methoxyethylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate;

4-[2-[2,6-difluoro-4-[[2-[[3-[[8-(4-methoxybutylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate;

4-[2-[4-[[2-[[3-[[8-[bis(2-methoxyethyl)carbamoyl]-3,8-diazabicyclo[3.2.1]octan-3-yl]methyl]benzoyl]amino]-4,5,6,7-tetrahydrobenzothiophene-3-carbonyl]amino]-2,6-difluoro-phenyl]ethyl]benzoate;

4-[2-[2,6-difluoro-4-[[2-[[3-[[8-(2-methylpropanoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate;

4-[2-[4-[[2-[[3-[[8-[2-(dimethylamino)acetyl]-3,8-diazabicyclo[3.2.1]octan-3-yl]methyl]benzoyl]amino]-4,5,6,7-tetrahydrobenzothiophene-3-carbonyl]amino]-2,6-difluoro-phenyl]ethyl]benzoic acid;

4-[2-[2,6-difluoro-4-[[2-[[3-[[8-[1-(methoxymethyl)cyclopropanecarbonyl]-3,8-diazabicyclo[3.2.1]octan-3-yl]methyl]benzoyl]amino]-4,5,6,7-tetrahydrobenzothiophene-3-carbonyl]amino]phenyl]ethyl]benzoic acid;

4-[2-[2,6-difluoro-4-[[2-[[3-[[8-[2-(4-methylpiperazin-1-yl)acetyl]-3,8-diazabicyclo[3.2.1]octan-3-yl]methyl]benzoyl]amino]-4,5,6,7-tetrahydrobenzothiophene-3-carbonyl]amino]phenyl]ethyl]benzoic acid;

4-[2-[2,6-difluoro-4-[[2-[[3-[[4-(4-hydroxybutylcarbamoyl)-2,2-dimethyl-piperazin-1-yl]methyl]benzoyl]amino]benzothiophene-3-carbonyl]amino]phenyl]ethyl]benzoic acid; and 4-[2-[4-[[2-[[3-[(4-acetyl-2,2-dimethyl-piperazin-1-yl)methyl]benzoyl]amino]-4,5,6,7-tetrahydrobenzothiophene-3-carbonyl]amino]-2,6-difluoro-phenyl]ethyl]benzoic acid.

Further, the present invention provides a pharmaceutical composition comprising a compound of formula I, or a pharmaceutically acceptable salt thereof, and a pharmaceutically acceptable carrier, diluent or excipient. Further, the present invention provides a pharmaceutical composition comprising a compound of formula II, or a pharmaceutically acceptable salt thereof, and a pharmaceutically acceptable carrier, diluent or excipient.

Further, the present invention provides a compound of formula I or II, or a pharmaceutically acceptable salt thereof, for use in therapy. The present invention provides a salt which is 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium, for use in therapy.

Further, the present invention provides a compound of formula I, or a pharmaceutically acceptable salt thereof, for use in the treatment of hyperphosphatemia. Further, the present invention provides a compound of formula II, or a pharmaceutically acceptable salt thereof, for use in the treatment of hyperphosphatemia. Further, the present invention provides a compound of formula I or II, or a pharmaceutically acceptable salt thereof, for use in the treatment of chronic kidney disease. The present invention provides a salt which is 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]

amino]phenyl]ethyl]benzoic acid, disodium, for use in the treatment of hyperphosphatemia. The present invention provides a solid dispersion formulation of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl] benzoic acid, disodium, wherein the formulation comprises 300% 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium, and 70% polyvinylpyrrolidone-vinyl acetate for use in the treatment of hyperphosphatemia.

The present invention provides a salt which is 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl] benzoic acid, disodium, for use in the treatment of chronic kidney disease. The present invention provides a solid dispersion formulation of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium, wherein the formulation comprises 30% 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium, and 70/o polyvinylpyrrolidone-vinyl acetate for use in the treatment of chronic kidney disease.

The present invention provides a compound or salt which is 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, or a pharmaceutically acceptable salt thereof, for use in the treatment of cardiovascular disease associated with chronic kidney disease. The present invention provides a salt which is 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium, for use in the treatment of cardiovascular disease associated with chronic kidney disease. The present invention provides a method of treating cardiovascular disease associated with chronic kidney disease comprising administrating to a patient in need thereof an effective amount of a compound or salt which is 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, or a pharmaceutically acceptable salt thereof.

Further, the present invention provides the use of a compound of formula I or II, or a pharmaceutically acceptable salt thereof, for the manufacture of a medicament for treating hyperphosphatemia, and/or chronic kidney disease.

Further, the present invention provides a method of treating hyperphosphatemia, comprising administering to a patient in need thereof an effective amount of a compound of formula I, or a pharmaceutically acceptable salt thereof. Further, the present invention provides a method of treating hyperphosphatemia, comprising administering to a patient in need thereof an effective amount of a compound of formula II, or a pharmaceutically acceptable salt thereof.

Further, the invention provides a method of treating hyperphosphatemia comprising administrating to a patient in need thereof an effective amount of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, or a pharmaceutically acceptable salt thereof. Further, the invention provides a method of treating hyperphosphatemia comprising administrating to a patient in need thereof an effective amount of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium. Further, the invention provides a method of treating hyperphosphatemia comprising administrating to a patient in need thereof an effective amount of a solid dispersion formulation of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl] benzoic acid, disodium, wherein the formulation comprises 30% 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium, and 70/o polyvinylpyrrolidone-vinyl acetate.

The term "pharmaceutically acceptable salt" includes an acid addition salt that exists in conjunction with the basic portion of a compound of formula I or II, or basic addition salt that exists in conjunction with the acidic portion of a compound of formula I or II. Such salts include the pharmaceutically acceptable salts, for example those listed in Handbook of Pharmaceutical Salts: Properties, Selection and Use, P. H. Stahl and C. G. Wermuth (Eds.), Wiley-VCH, New York, 2002 which are known to the skilled artisan.

In addition to pharmaceutically acceptable salts, other salts are contemplated in the invention. They may serve as intermediates in the purification of compounds or in the preparation of other pharmaceutically-acceptable salts, or are useful for identification, characterization or purification of compounds of the invention.

As used herein, the term "patient" refers to a warm blooded animal such as a mammal and includes a human. A human is a preferred patient.

Cardiovascular disease associated with chronic kidney disease may include sudden cardiac death, arrhythmia, angina, myocardial infarction, and heart failure (Kestenbaum et al., *Serum Phosphate Levels and Mortality Risk Among People with Chronic Kidney Disease*, J. Am. Soc. Nephrol. 16: 520-528, 2005).

One skilled in the art may treat hyperphosphatemia and/or chronic kidney disease by administering to a patient presently displaying symptoms an effective amount of the compound of formula I. Thus, the terms "treatment" and "treating" are intended to refer to all processes wherein there may be a slowing, interrupting, arresting, controlling, or stopping of the progression of an existing disorder and/or symptoms thereof, but does not necessarily indicate a total elimination of all symptoms.

One skilled in the art may treat hyperphosphatemia and/or chronic kidney disease by administering to a patient having recognized risk factors for hyperphosphatemia and/or chronic kidney disease an effective amount of the compound of formula I. For instance, Patients having phosphate levels in the high end of the normal range, in consideration with other factors such as hypertension and/or diabetes, may be considered as having recognized risk for hyperphosphatemia and/or chronic kidney disease, and cardiovascular disease associated with chronic kidney disease.

As used herein, the term "effective amount" of a compound of formula I or II refers to an amount which is effective in treating a disorder, such as hyperphosphatemia and/or chronic kidney disease described herein. One skilled in the art can determine an effective amount by the use of conventional techniques and by observing results obtained under circumstances considered to be informative to the current patient. In determining an effective amount or dose of a compound of formula I or II, a number of factors are considered, including, which compound of formula I or II is administered; whether co-administration of other agents exists; the species of mammal; its size, age, and general health; the degree of involvement or the severity of the disorder, such as hyperphosphatemia and/or chronic kidney disease; the response of the individual patient; the mode of administration; the bioavailability characteristics of the preparation administered; the dose regimen selected; and other relevant circumstances.

The compounds of the present invention can be administered alone or in the form of a pharmaceutical composition combined with pharmaceutically acceptable carriers or excipients, the proportion, and nature of which are determined by the solubility and chemical properties, including stability, of the compound selected, the chosen route of administration, and standard pharmaceutical practice. The compounds of the present invention, while effective themselves, may also be formulated and administered in the form of their pharmaceutically acceptable salts.

One skilled in the art of preparing formulations can readily select the proper form and mode of administration depending upon the particular characteristics of the compound selected, the disorder or condition to be treated, the stage of the disorder or condition, and other relevant circumstances (See, e.g., Remington: The Science and Practice of Pharmacy, L. V. Allen, Editor, 22$^{nd}$ Edition, Pharmaceutical Press, 2012).

Certain abbreviations are defined as follows: "AcOH" refers to acetic acid; "ACN" refers to acetonitrile; "BOP" refers to benzotriazole-1-yl-oxy-tris-(dimethylamino)-phosphonium hexafluorophosphate; "DCM" refers to dichloromethane or methylene chloride; "DIPEA" refers to N,N-diisopropylethylamine; "DMF" refers to N,N-dimethylformamide; "DMSO" refers to dimethylsulfoxide; "EDCI" refers to 3-(ethyliminomethyleneamino)-N,N-dimethylpropan-1-amine; "EtOAc" refers to ethyl acetate; "EtOH" refers to ethanol; "FBS" refers to fetal bovine serum; "HATU" refers to 1-[bis(dimethylamino)methylene]-1H-1,2,3-triazolo[4,5-b]pyridinium 3-oxid hexafluorophosphate; "HEPES" refers to 2-[4-(2-hydroxyethyl)piperazin-1-yl]ethanesulfonic acid' "HOBT" refers to hydroxybenzotriazole; 'hr' refers to hour or hours; "IC$_{50}$" refers to the concentration of an agent that produces 50% of the maximal inhibitory response possible for that agent; "LC-ES/MS" refers to Liquid Chromatography Electrospray Mass Spectrometry; "min" refers to minute or minutes; "MeOH" refers to methanol or methyl alcohol; "MTBE" refers to methyl-tert-butyl ether; "$^{33}$P" refers to phosphorus-33; "psi" refers to pounds per square inch; "PyBOP" refers to benzotriazol-1-yl-oxytripyrrolidinophosphonium hexafluorophosphate; "RT" refers to room temperature; "TEA" refers to triethylamine; "TFA" refers to trifluoroacetic acid; "THF" refers to tetrahydrofuran; "Tris" refers to 2-amino-2-hydroxymethyl-propane-1,3-diol; "U/mL" refers to units per milliliter; "PVP-VA" refers to polyvinylpyrrolidone-vinyl acetate.

Scheme 1

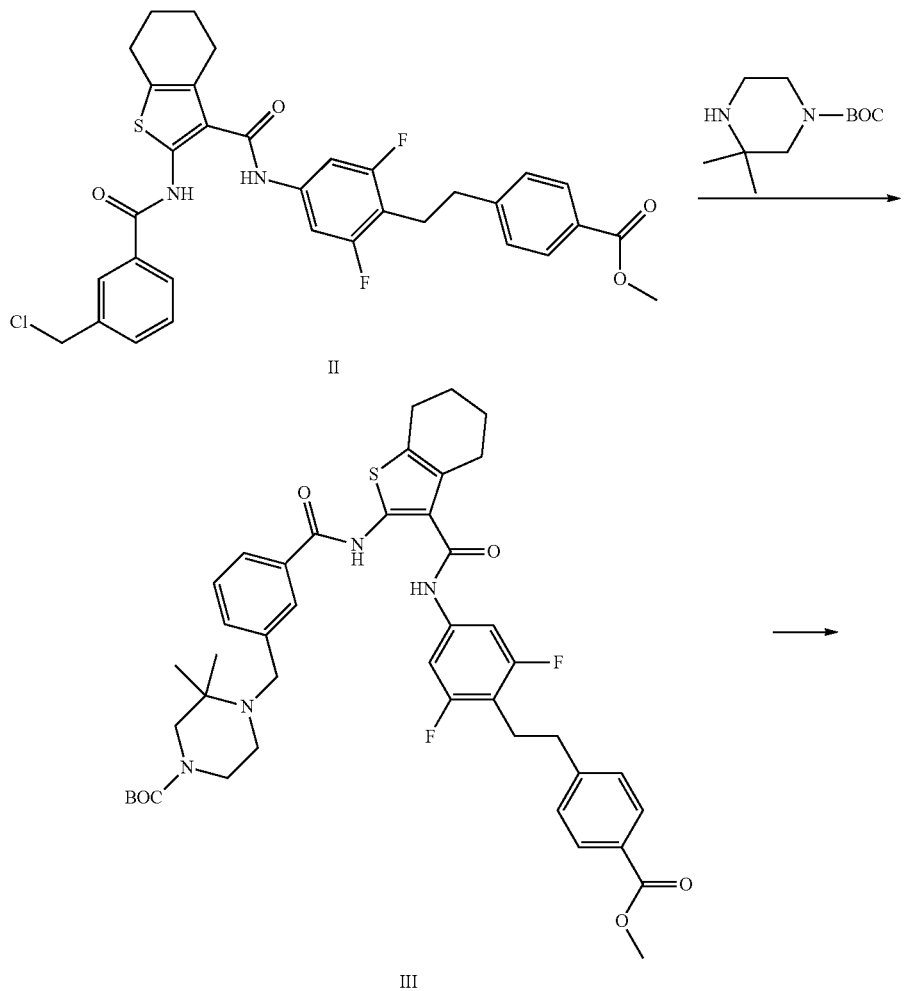

-continued
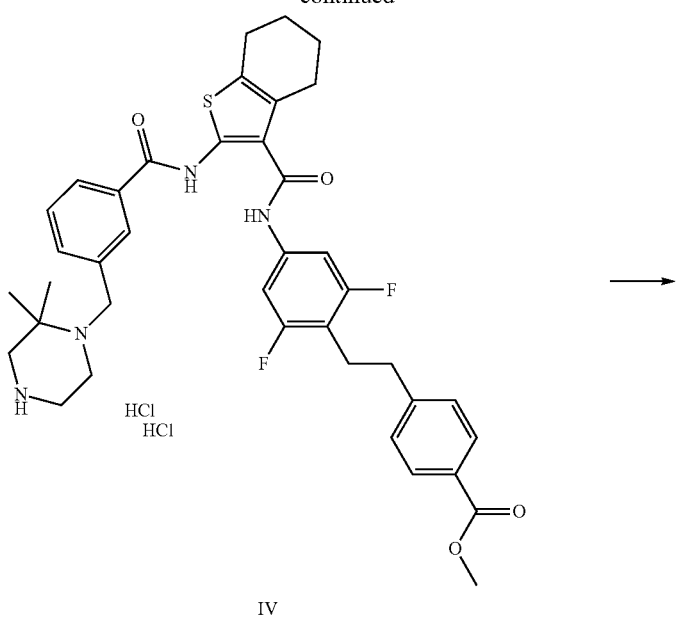
IV
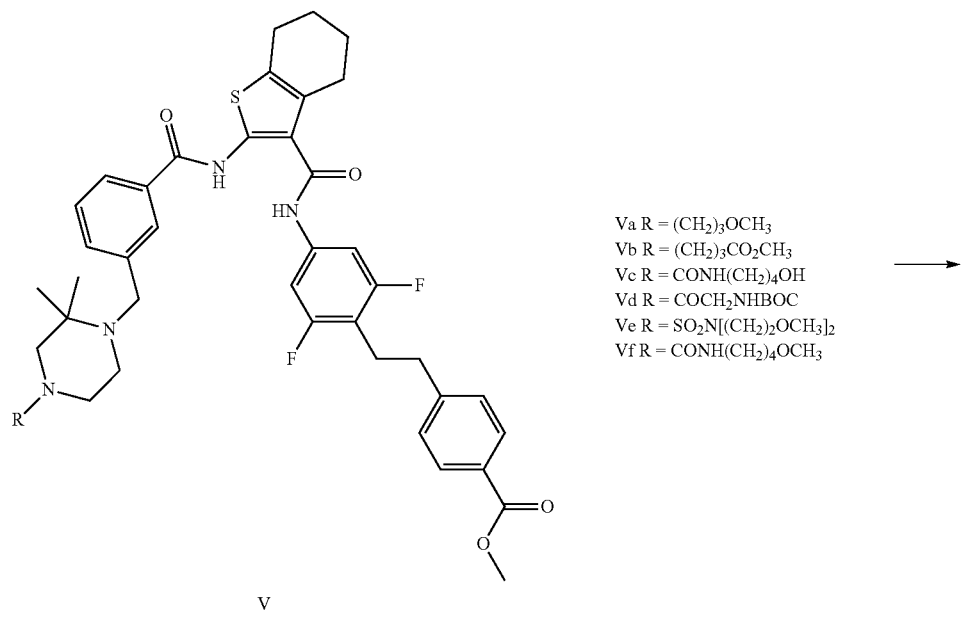
V
Va R = (CH$_2$)$_3$OCH$_3$
Vb R = (CH$_2$)$_3$CO$_2$CH$_3$
Vc R = CONH(CH$_2$)$_4$OH
Vd R = COCH$_2$NHBOC
Ve R = SO$_2$N[(CH$_2$)$_2$OCH$_3$]$_2$
Vf R = CONH(CH$_2$)$_4$OCH$_3$

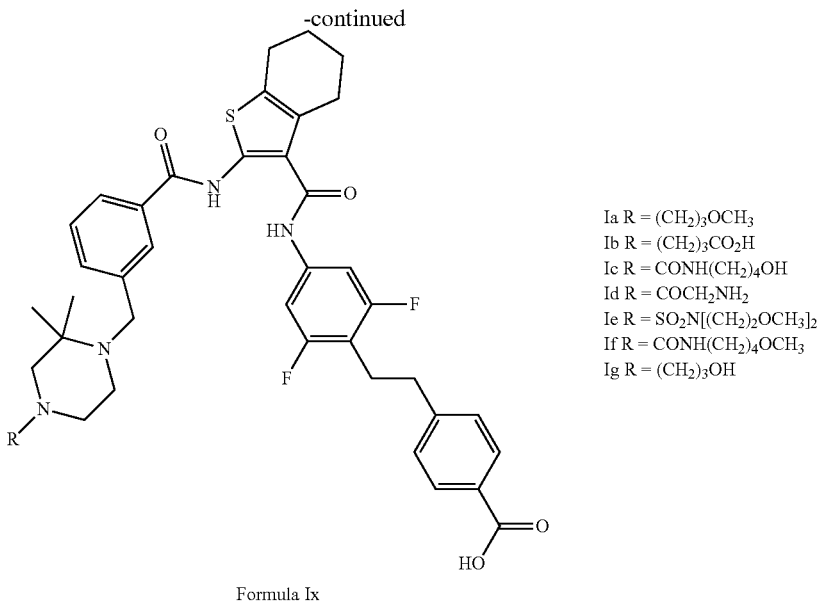

Ia R = (CH$_2$)$_3$OCH$_3$
Ib R = (CH$_2$)$_3$CO$_2$H
Ic R = CONH(CH$_2$)$_4$OH
Id R = COCH$_2$NH$_2$
Ie R = SO$_2$N[(CH$_2$)$_2$OCH$_3$]$_2$
If R = CONH(CH$_2$)$_4$OCH$_3$
Ig R = (CH$_2$)$_3$OH

Formula Ix

Scheme 1 depicts the synthetic route to compounds of Formula Ix. Generally, the alkyl halide compound II may be aminated under various conditions well appreciated in the art, for example, using an amine and an appropriate non-nucleophilic base such as TEA, DIPEA, or in a suitable organic solvent such as THF, ACN, or DMF. More specifically, about 2 equivalents of tert-butyl 3,3-dimethylpiperazine-1-carboxylate may be heated in a microwave reaction vessel at 110° C. in the presence of about 1 equivalent of alkyl halide II and about 12 equivalents of DIPEA in ACN to obtain the alkyl amine III. The Boc protecting group of Compound III may be removed under acidic conditions well described in the art. More specifically, compound II may be treated with an excess of HCl in 1,4-dioxane in DCM to yield the hydrochloride salt IV.

Subsequent alkylation of compound IV may be carried out under a wide array of conditions well known in the art, such as treatment with an alkyl halide under alkylation conditions, for example, with an appropriately substituted alkyl halide and the amine IV in the presence of a non-nucleophilic base, such as TEA, DIPEA, pyridine, or 1,8-diazabicycloundec-7-ene, in an appropriate organic solvent such as DCM, ACN or DMF. Additionally, alkylation of compound IV may be performed under reductive amination conditions, such as with an appropriately substituted aldehyde in the presence of a reducing agent such as sodium borohydride, sodium triacetoxyborohydride, or sodium cyanoborohydride, and a catalytic amount of an organic acid, such as AcOH or TFA, in an appropriate organic solvent, such as MeOH, EtOH, ACN, DCM, THF, or DMF. More specifically, compound IV may be treated with about 2 equivalents DIPEA and subsequently treated with 3-methoxyproprionaldehyde or 4-oxobutanoic acid methyl ester in the presence of about 2 equivalents of sodium triacetoxyborohydride and catalytic AcOH in DCM, to obtain compounds Va and Vb, respectively.

Acylation or sulfonylation of compound IV may be accomplished under conditions well known in the art, for example, using an acyl halide or sulfonyl halide under basic conditions using an excess of an appropriate non-nucleophilic base such as TEA or DIPEA in a suitable organic solvent such as DCM, THF, ACN, or DMF. More specifically, compound IV may be treated with about 4 equivalents of DIPEA and about 2 equivalents of N-(4-hydroxybutyl)-3,3-dimethyl-piperazine-1-carboxamide hydrochloride in a mixture of about 1:10 MeOH:ACN and heated in a microwave reactor at 100° C., to obtain the compound Vc. Acylation of the amine IV may also be performed under standard amide coupling conditions well known in the art, for example, using EDCI and HOBT, HATU, BOP, or PyBOP, in the presence of a non-nucleophilic base such as TEA or DIPEA, and in a suitable organic solvent such as MeOH, ACN, THF, DCM, or DMF, or a combination thereof. More specifically, about 1.2 equivalents of compound IV may be treated with about 0.9 equivalents of 1,8-diazabicyclo [5.4.0]undec-7-ene and subsequently treated with about 1 equivalent N-(tert-butoxycarbonyl) glycine, 0.5 equivalents HOBT, and 1.2 equivalents EDCI in DMF to obtain compound Vd. Sulfonylation of compound IV may be achieved in the presence of about 1.5 equivalents bis(2-methoxyethyl)sulfamoyl chloride and about 5 equivalents TEA in DMF with heating, to obtain compound Ve.

Moreover, acylation of amines to obtain ureas, by nucleophilic addition of an amine to an isocyanate under basic conditions, are also well described in the art. Specifically, about 1 equivalent of compound IV may be treated with about 2 equivalents of 1-isocyanato-4-methoxy-butane in the presence of about 4 equivalents TEA in DCM to obtain compound Vf.

The compounds of Formula Ix may be prepared by saponification of the methyl ester moiety of compounds V under either acidic or basic conditions as well known in the art. More specifically, compounds Va-Vf may be treated with about 1-5 equivalents of LiOH in THF, MeOH, H$_2$O, or an appropriate mixture thereof, to obtain compounds of Formula Ia-f. These conditions may simultaneously saponify the additional ester moiety in compound Vb. Additional protecting groups may be removed by well-known methods, for example, treatment of compound Ve with an excess of 4 M HCl in dioxane, after the ester saponification is completed. Moreover, additional heteroatom-protected alkyl aldehydes, specifically 3-[(tert-butyldimethylsilyl)

oxy]-1-propanal, may be treated with compound IV under reductive amination conditions as described above, deprotected in situ, and ultimately saponified as described above. More specifically, 3-[(tert-butyldimethylsilyl)oxy]-1-propanal and compound IV may be treated to reductive amination conditions, using sodium triacetoxyborohydride and catalytic AcOH as described over, with subsequent removal of the silyl group in situ, using excess HCl in 1,4-dioxane. Final saponification with LiOH, as described above, may be performed to obtain compound of Formula Ig.

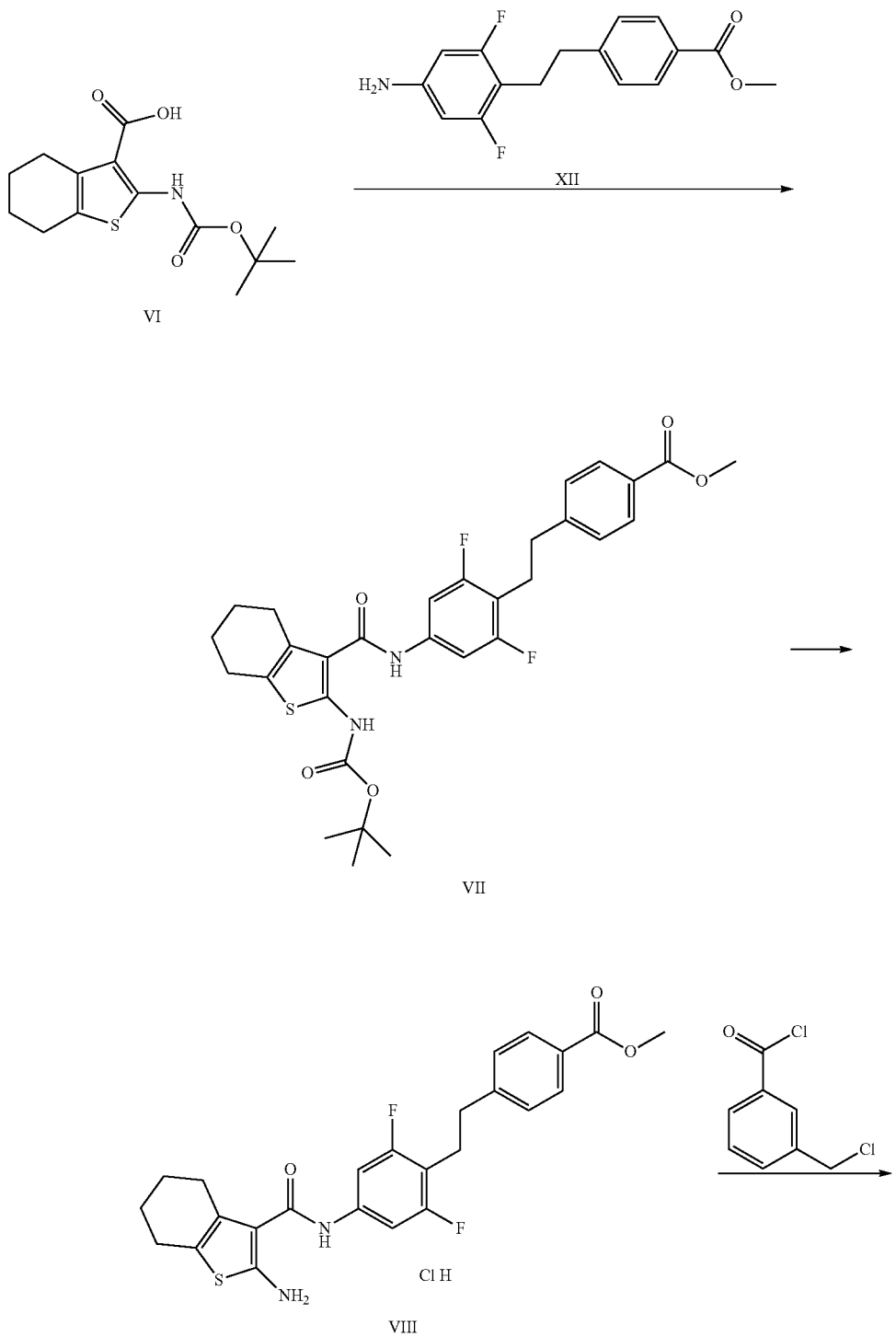

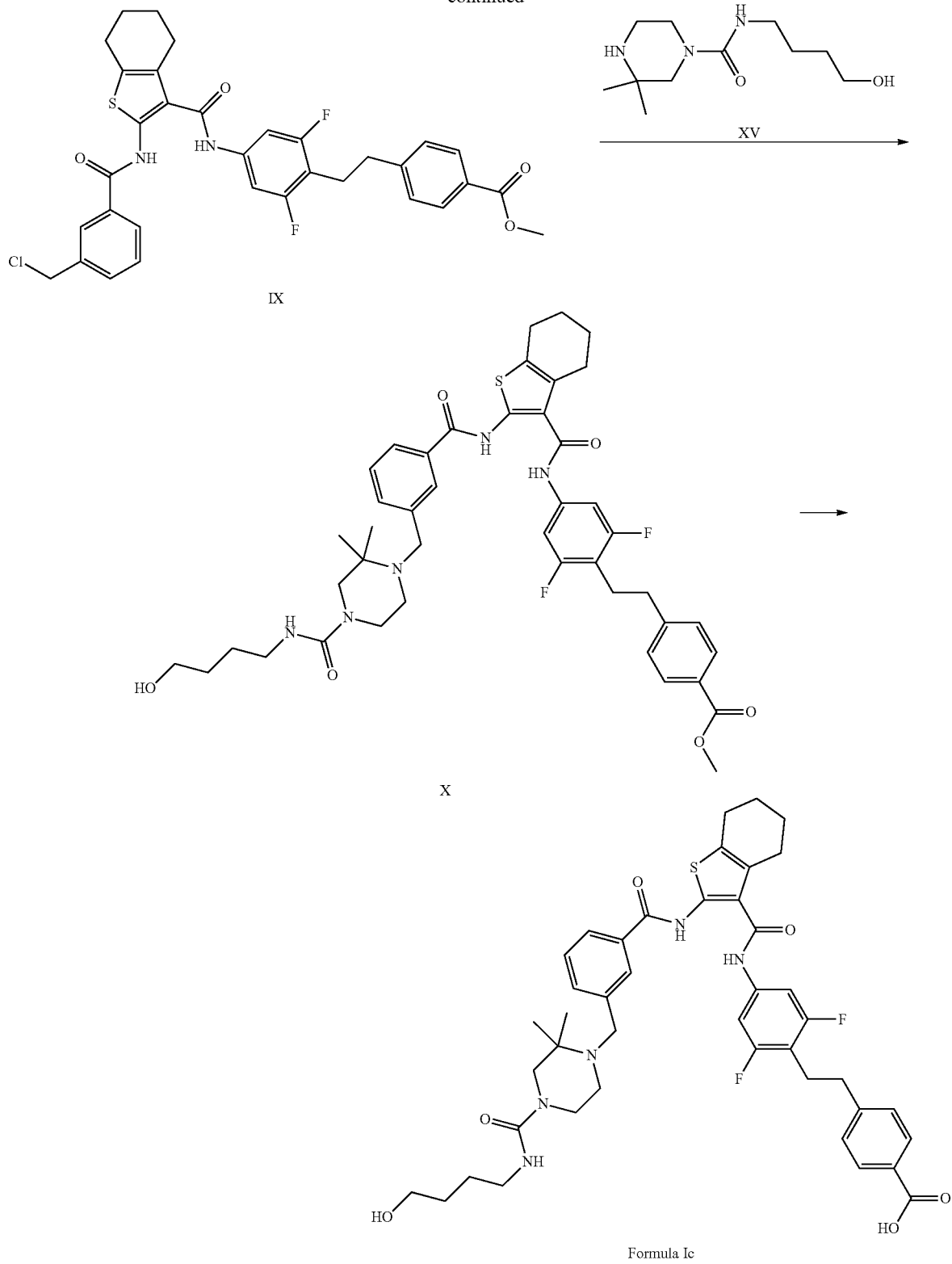

An alternative synthesis to compound of Formula Ic is depicted in Scheme 2. A mixture of about 1 equivalent methyl 4-[2-(4-amino-2,6-difluoro-phenyl)ethyl]benzoate XII and 1.1 equivalents 3-(tert-butoxycarbonylamino)-4,5,6,7-tetrahydrobenzothiophene-2-carboxylic acid (Aurum Pharmatech) in DCM may be treated with about 1.25 equivalents bis-(2-oxo-3-oxazolidinyl)phosphinic chloride in the presence of about 5 equivalents DIPEA to give the product compound VII, which may be deprotected under standard conditions well known in the art, specifically with excess 4 N HCl in 1,4-dioxane and DCM as solvent, to obtain amine compound VIII. Amine VIII may be subjected to acylation conditions as described above, specifically with about 1.1 equivalents 3-(chloromethyl)benzoyl chloride in the presence of pyridine with DCM as solvent, to obtain compound IX. The alkyl chloride IX may be aminated under a wide array of amination conditions well known in the art, more specifically with about 2 equivalents N-(4-hydroxybutyl)-3,3-dimethyl-piperazine-1-carboxamide hydrochloride in the presence of about 4 equivalents DIPEA in a mixture of ACN/MeOH as described above to obtain compound X, and subsequent saponification as described above may yield the compound of Formula Ic.

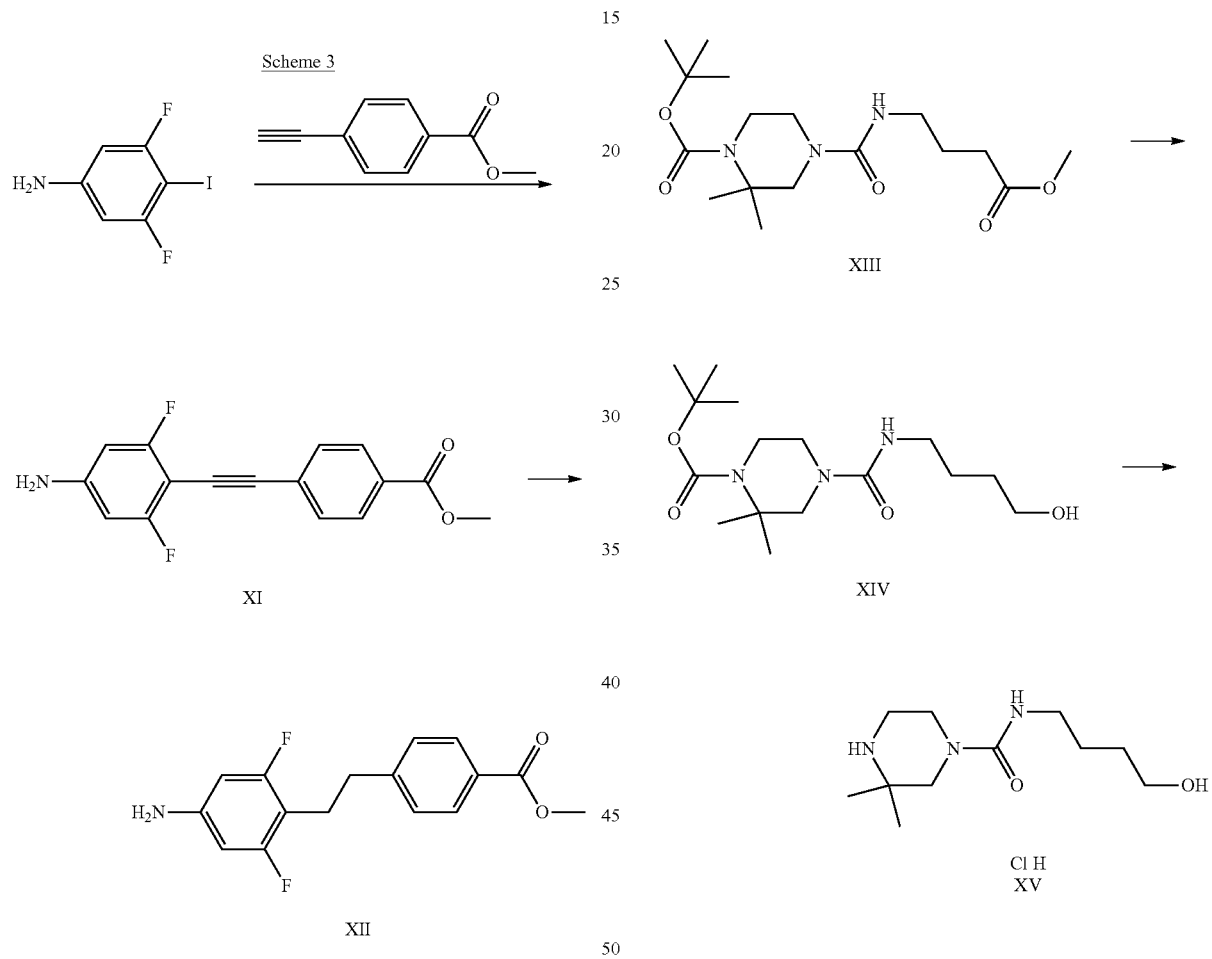

The synthesis of aniline compound XII is depicted in Scheme 3. Generally, palladium-copper mediated Sonogashira cross-coupling between an aryl halide and a substituted acetylene are well known in the art. Specifically, about 1 equivalent 3,5-difluoro-4-iodoaniline (AstaTech) and about 1 equivalent methyl 4-ethynylbenzoate (Alfa Aesar) may be heated in the presence of about 0.4 equivalents bis(triphenylphosphine)-palladium(II) dichloride and 0.07 equivalents CuI with about 10 equivalents DIPEA in THF to give the diaryl acetylene compound XI, which may be reduced under standard conditions well described in the art, specifically catalytic hydrogenation at about 60 psi in the presence of palladium black in a solvent mixture of THF/H₂O, to obtain the requisite aniline compound XII.

Scheme 4 illustrates the synthesis of amine XV. Nucleophilic addition of 1 equivalent t-butyl 2,2-dimethylpiperazine-1-carboxylate to about 1.1 equivalent of methyl 4-isocyanatobutanoate in the presence of 3 equivalents DIPEA with DCM as reaction solvent may yield the urea compound XIII. Reduction of the ester moiety may be accomplished using a wide array of conditions well described in the literature, including BH3, lithium borohydride, and diisobutyl aluminum hydride. More specifically, 1 equivalent of ester XII may be treated with about 3 equivalents of lithium borohydride in THF to give reduced product XIV; subsequent removal of the BOC protecting group as described above gives the requisite compound XV.

Scheme 5
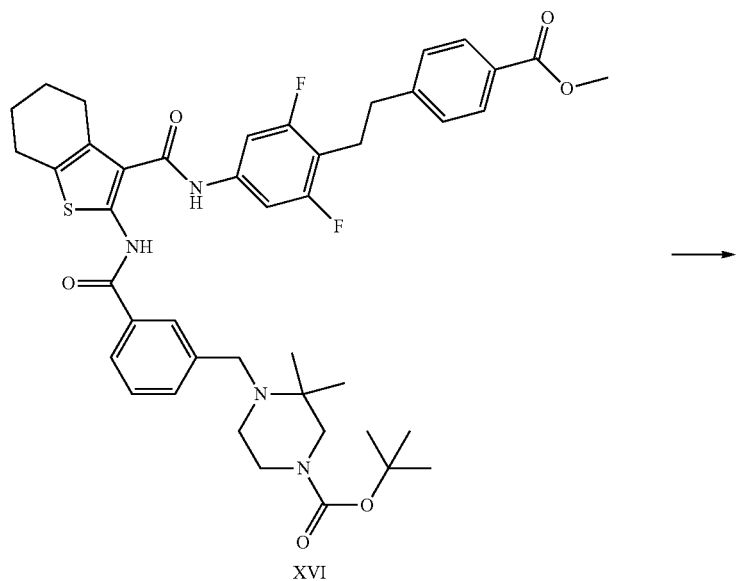
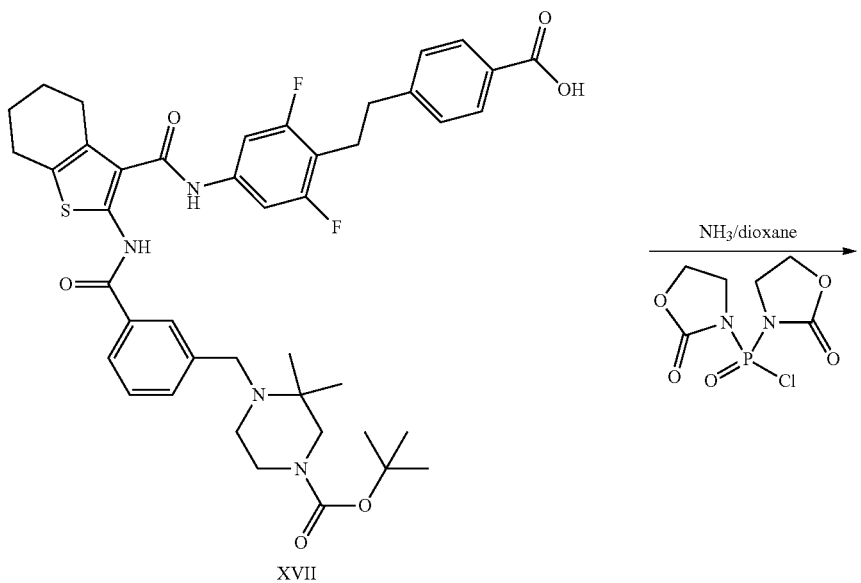

-continued
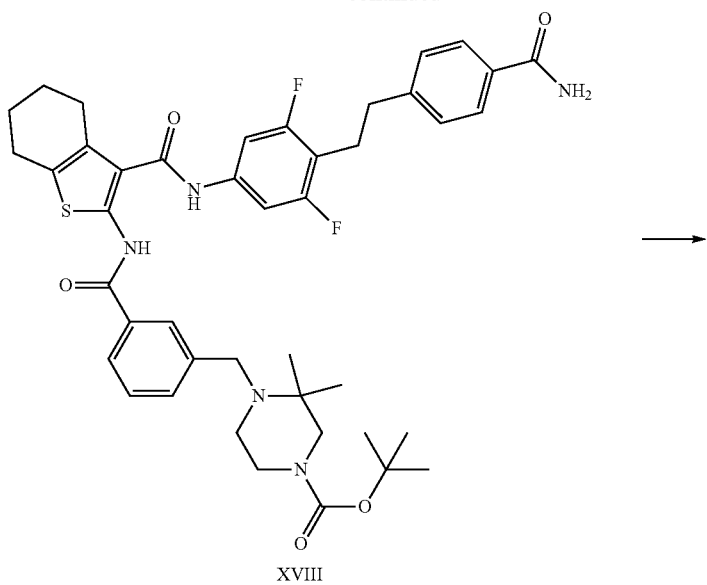
XVIII
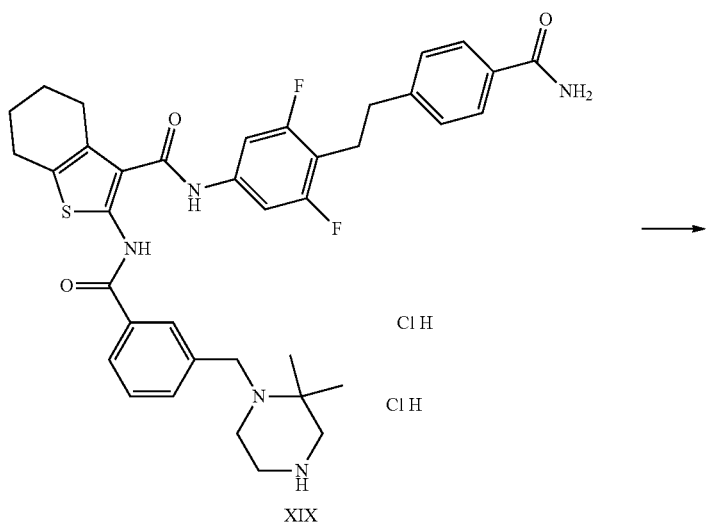
XIX
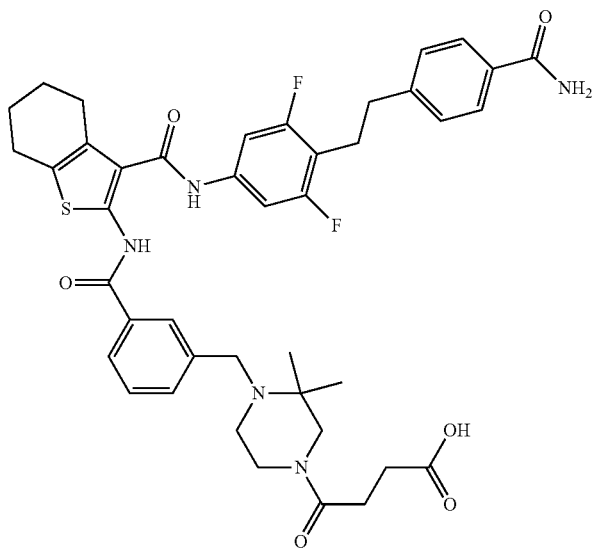
Formula Iy

Scheme 5 depicts the synthesis of compound of Formula Iy. Hydrolysis of the ester moiety in compound XVI may be achieved under conditions well known in the art, such as with an alkaline base such as NaOH, KOH, or LiOH in aqueous, organic, or biphasic solvent mixtures. More specifically, the ester XVI may be treated with 5 equivalents LiOH in a mixture of aqueous THF; mild acidification of the saponified acid may yield compound XVII. Subsequent direct amidation via the acid chloride may be accomplished under mild conditions (E. Valeur and M. Bradley, *Chem. Soc. Rev.*, 2009, 38, 606-631). More specifically, the acid chloride of acid compound XVII may be generated in situ with 1.2-2.5 equivalents of bis(2-oxo-3-oxazolidinyl)phosphinic chloride at room temperature followed by treatment with excess ammonia to obtain the desired primary amide XVIII. Removal of the BOC protecting group as described above gives the requisite compound XIX as described above. Acylation of the unmasked piperizine nitrogen may be achieved under conditions well known in the art, specifically treatment of compound XIX with 5 equivalents of a suitable non-nucleophilic base such as DIPEA in the presence of an acylating agent such as succinic anhydride to obtain the compound of Formula Iy. Other compounds of Formula I and/or II may be prepared by the skilled artisan by procedures analogous to those described herein using appropriate starting materials and modifications as needed.

Scheme 6

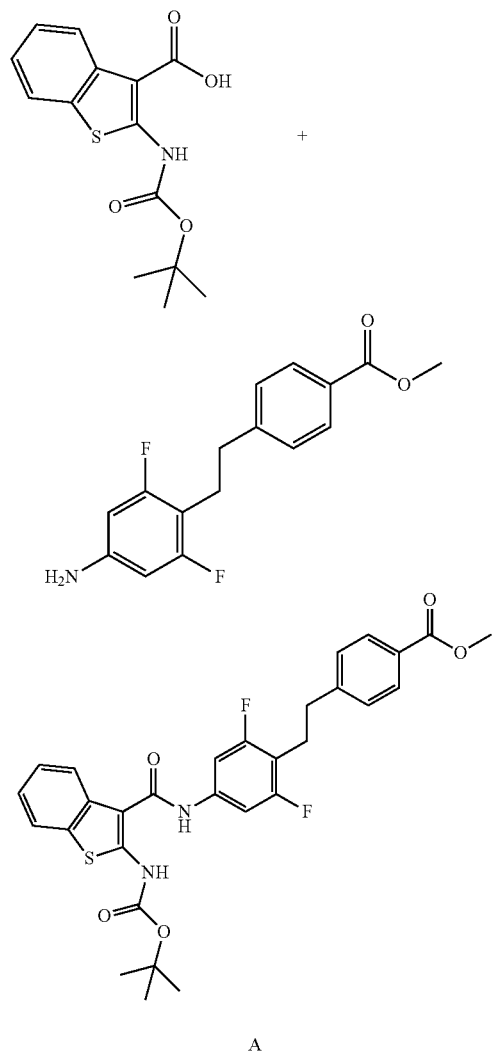

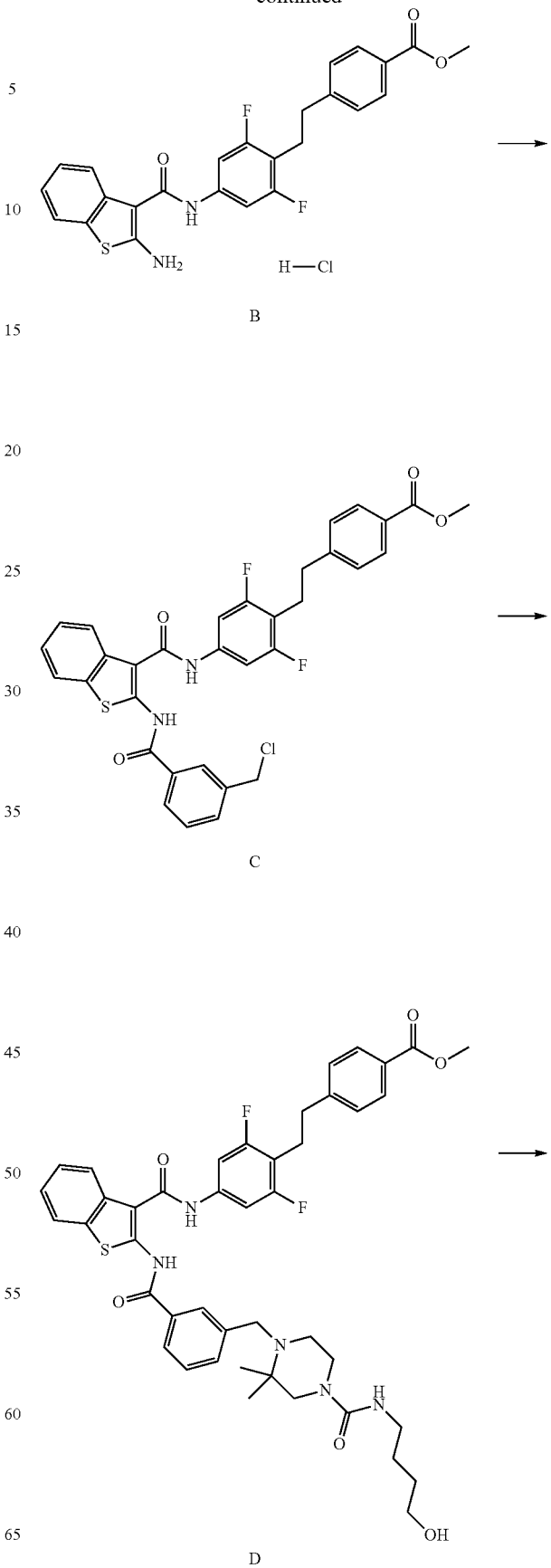

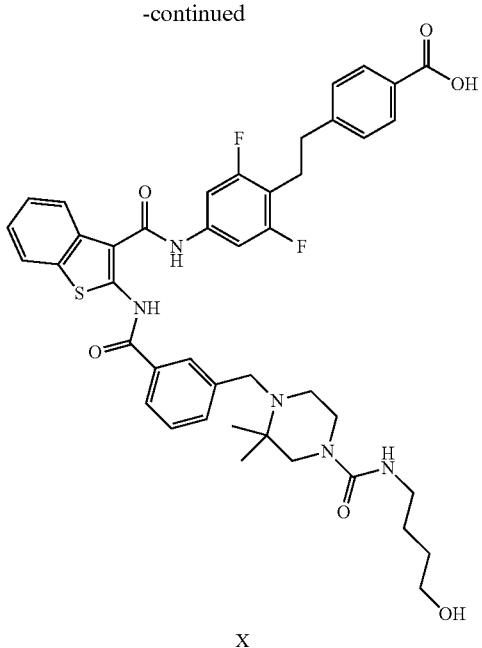

X

The synthesis of compound X is depicted in Scheme 6. A BOPCl mediated amide coupling yields compound A. Removal of the BOC protecting group as described above gives the requisite compound B. Acylation of the amino group maybe achieved under conditions well known in the art, specifically treatment of B with 3-(chloromethyl)-benzoyl chloride in presence of pyridine to obtain compound C. Nucleophilic substitution of benzylic chloride with substituted piperazine yields methyl benzoate D. Subsequent saponification as described above affords the compound X.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1×50 mm 3.5 µm; gradient: 5-100% B in 3 min, then 100% B for 0.75 min, or 5-95% B in 1.5 min, then 95% B for 0.25 min; column temperature: 50° C.+/−10° C.; flow rate: 1.2 mL/min; Solvent A: deionized water with 0.1% HCOOH; Solvent B: ACN with 0.10% formic acid; wavelength 214 nm. Alternate LC-MS conditions (high pH): column: XTERRA® MS C18 columns 2.1×50 mm, 3.5 µm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min or 5-95% B in 1.5 min, then 95% B for 0.25 min; column temperature: 50° C.+/−10° C.; flow rate: 1.2 mL/min; Solvent A: 10 mM $NH_4HCO_3$ pH 9; Solvent B: ACN; wavelength: 214 nm.

NMR spectra are performed on a Bruker AVIII HD 400 MHz NMR Spectrometer or a Varian VNMRS 300 or 400 MHz NMR Spectrometer, obtained as $CDCl_3$ or DMSO-$d_6$ solutions reported in ppm, using residual solvent [$CDCl_3$, 7.26 ppm; DMSO-$d_6$, 2.50 ppm] as reference standard. When peak multiplicities are reported, the following abbreviations may be used: s (singlet), d (doublet), t (triplet), q (quartet), m (multiplet), br s (broad singlet), dd (doublet of doublets), dt (doublet of triplets). Coupling constants (J), when reported, are reported in hertz (Hz).

Preparation 1 methyl 4-[2-(4-amino-2,6-difluoro-phenyl)ethynyl]benzoate

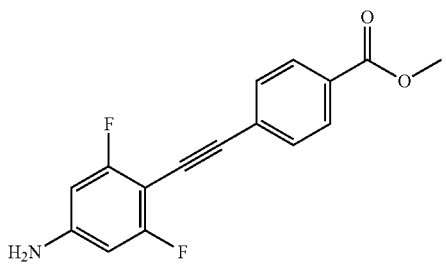 [SMILES: COC(=O)c1ccc(C#Cc2c(F)cc(N)cc2F)cc1]

A suspension of 3,5-difluoro-4-iodoaniline (14.7 g, 55.9 mmol), CuI (0.745 g, 3.91 mmol), bis(triphenylphosphine)palladium(II) dichloride (1.59 g, 2.24 mmol), methyl 4-ethynylbenzoate (9.05 g, 55.9 mmol), TEA (114 mL) and THF (44.1 mL) is stirred at 60° C. for 3 hr. The mixture is cooled to RT and the solvent evaporated to dryness under reduced pressure. EtOAc (100 mL) and $H_2O$ (100 mL) are added, and the resulting solid is filtered over diatomaceous earth. The organic layer from the filtrate is separated, dried over $MgSO_4$, and evaporated to dryness under reduced pressure. A 1:1 mixture of DCM:heptane (400 mL) is added to the resulting residue and the mixture is stirred at RT overnight. The resulting solid is collected by filtration and dried under vacuum to obtain the title compound (8.0 g, 45.8% yield) as a brown solid. $^1$H NMR (300 MHz, DMSO-$d_6$) δ 3.86 (s, 3H), 6.26-6.37 (m, 4H), 7.59 (d, J=8.2 Hz, 2H), 7.96 (d, J=8.5 Hz, 2H).

Preparation 2 methyl 4-[2-(4-amino-2,6-difluoro-phenyl)ethyl]benzoate

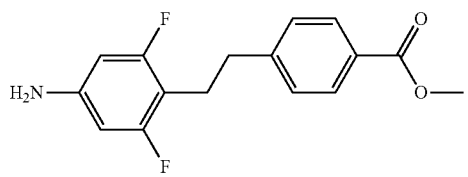 [SMILES: COC(=O)c1ccc(CCc2c(F)cc(N)cc2F)cc1]

A 500 mL Parr shaker is charged with Pd black (0.53 g, 5.0 mmol) under $N_2$. A degassed 4:1 solution of MeOH/THF (25 mL) is added followed by a degassed solution of methyl 4-[2-(4-amino-2,6-difluoro-phenyl)ethynyl]benzoate (1.17 g, 3.38 mmol) in a 4:1 mixture of MeOH/THF (25 mL) under $N_2$. The resulting mixture is purged with $N_2$ and pressurized with $H_2$ to 60 psi. The sealed vessel is heated at 40° C. for 14 hr. The resulting suspension is filtered through a pad of diatomaceous earth under $N_2$ and evaporated to dryness in vacuo. The resulting residue is purified by chromatography over silica, eluting with a gradient of 25-35% hexanes/THF, to afford the title compound as a white solid (404 mg, 400/% yield) after solvent evaporation and drying under vacuum. $^1$H NMR (400.13 MHz, DMSO-$d_6$) δ, 2.71-2.83 (m, 4H), 3.84 (s, 3H), 5.52 (s, 2H), 6.10-6.15 (m, 2H), 7.28 (d, J=8.3 Hz, 2H), 7.85 (d, J=8.2 Hz, 2H). LC-ES/MS (m/z) 292 [M+1].

Preparation 3 tert-butyl 4-[(4-methoxy-4-oxo-butyl)carbamoyl]-2,2-dimethyl-piperazine-1-carboxylate

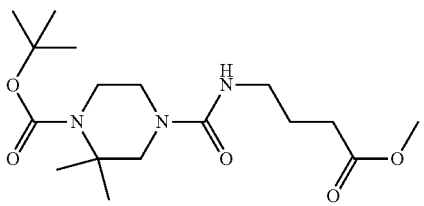 [SMILES: COC(=O)CCCNC(=O)N1CCN(C(=O)OC(C)(C)C)C(C)(C)C1]

A 30 mL scintillation vial is charged with t-butyl 2,2-dimethylpiperazine-1-carboxylate (500 mg, 2.28 mmol) and DCM (12 mL). The resulting solution is cooled in an ice/water bath and DIPEA (1.20 mL, 6.85 mmol) is added in one portion. A solution of methyl 4-isocyanatobutanoate (447 mg, 2.97 mmol) in DCM (3 mL) is added drop wise over 5 min. The reaction mixture is slowly warmed to RT and stirred for a further 15 min. The mixture is partitioned between 5% aqueous citric acid (100 mL) and DCM (20 mL). The organic layer is separated, and the aqueous layer is extracted twice more with DCM (20 mL each). The combined organic extracts are washed sequentially with saturated aqueous $NaHCO_3$ (30 mL) and saturated aqueous NaCl (30 mL), dried over anhydrous $Na_2SO_4$, filtered, and evaporated under reduced pressure. The resulting residue is purified by chromatography over silica, eluting with a gradient of 30-50% hexanes/acetone, to obtain the title compound as colorless viscous oil (848 mg, 95% yield) after solvent removal and drying under vacuum. $^1$H NMR (399.8 MHz, CDCl$_3$) δ 1.34 (s, 6H), 1.45 (s, 9H), 1.83 (t, J=6.9 Hz, 2H), 2.37 (t, J=7.1 Hz, 2H), 3.25-3.30 (m, 2H), 3.37 (t, J=5.7 Hz, 2H), 3.47 (s, 2H), 3.65 (s, 3H), 3.71 (t, J=5.7 Hz, 2H), 4.65-4.68 (m, 1H). LC-ES/MS (m/z) 358 [M+1].

Preparation 4 tert-butyl 4-(4-hydroxybutylcarbamoyl)-2,2-dimethyl-piperazine-1-carboxylate

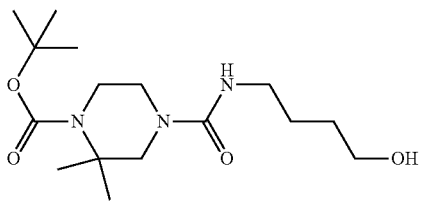 [SMILES: CC(C)(C)OC(=O)N1CCN(C(=O)NCCCCO)CC1(C)C]

A 2 M solution of LiBH$_4$ in THF (3.02 mL, 6.04 mmol) is added drop wise to a 100 mL round bottom flask containing tert-butyl 4-[(4-methoxy-4-oxo-butyl)carbamoyl]-2,2-dimethyl-piperazine-1-carboxylate (783 mg, 2.01 mmol) and THF (2 mL) at RT. The resulting mixture is stirred for 12 hr at RT. The reaction mixture is quenched with 0.5 mL of MeOH, stirred at RT for 20 min, and partitioned between 5% aqueous $NaHCO_3$ (150 mL) and DCM (50 mL). The organic layer is separated, and the aqueous layer is extracted twice more with DCM (50 mL each). The combined organic layers are washed with saturated aqueous NaCl (50 mL), dried over anhydrous $Na_2SO_4$, filtered, and evaporated to dryness under reduced pressure to afford the title compound as a white solid (634 mg, 96% yield). $^1$H NMR (399.8 MHz, CDCl$_3$) δ 1.36 (s, 6H), 1.46 (s, 9H), 1.58-1.63 (m, 4H), 3.31-3.28 (m, 2H), 3.49 (s, 2H), 3.66-3.69 (m, 2H), 3.71-3.74 (m, 2H), 3.37-3.39 (m, 2H). LC-ES/MS (m/z) 330 [M+1].

Preparation 5

N-(4-hydroxybutyl)-3,3-dimethyl-piperazine-1-carboxamide hydrochloride

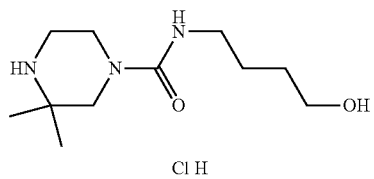 [SMILES: CC1(C)CN(C(=O)NCCCCO)CCN1 ; "Cl H"]

A 30 mL scintillation vial is charged with a solution of tert-butyl 4-(4-hydroxybutylcarbamoyl)-2,2-dimethyl-piperazine-1-carboxylate (631 mg, 1.92 mmol) in DCM (20 mL). A 4 N solution of HCl in dioxane (2.4 mL, 9.58 mmol) is added drop wise over 5 min and the resulting solution is stirred at RT for 2 hr. The volatiles are removed in vacuo and the residue is dried under vacuum to afford the title compound as a hygroscopic white oily solid (100% yield, quantitative), suitable for use in the next step without further purification. LC-ES/MS (m/z) 230 [M+1].

Preparation 6 methyl 4-[2-[4-[[2-(tert-butoxycarbonylamino)-4,5,6,7-tetrahydrobenzothiophene-3-carbonyl]amino]-2,6-difluoro-phenyl]ethyl]benzoate

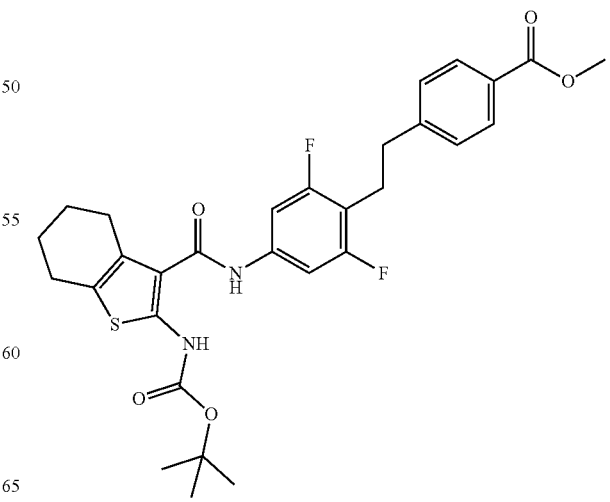

A 100 mL round bottom flask is charged with methyl 4-[2-(4-amino-2,6-difluoro-phenyl)ethyl]benzoate (2.11 g, 7.24 mmol), 3-(tert-butoxycarbonylamino)-4,5,6,7-tetrahydrobenzothiophene-2-carboxylic acid (2.37 g, 7.97 mmol), and DCM (60 mL). The resulting suspension is cooled in an ice/water bath, and DIPEA (5.05 mL, 29.0 mmol) is added drop wise to afford a yellow-brown turbid solution. Solid bis-(2-oxo-3-oxazolidinyl)phosphinic chloride (2.30 g, 9.05 mmol) is added in small portions over 30 min at 0° C. The reaction mixture is then warmed to RT and stirred for 24 hr. Additional solid 3-(tert-butoxycarbonylamino)-4,5,6,7-tetrahydrobenzothiophene-2-carboxylic acid (0.6 g, 2.0 mmol) is added followed by additional DIPEA (1.26 mL, 7.25 mmol) and solid bis-(2-oxo-3-oxazolidinyl)phosphinic chloride (0.58 g, 2.26 mmol) in small portions over 5 min. The resulting turbid brown reaction mixture is stirred at RT for 12 hr. The reaction mixture is partitioned between 5% aqueous citric acid (150 mL) and DCM (25 mL), the organic layer is separated, and the aqueous layer is extracted twice more with DCM (50 mL each). The combined organic extracts are washed sequentially with 10% aqueous NaHCO$_3$ (50 mL), saturated aqueous NaCl (50 mL), dried over anhydrous Na$_2$SO$_4$, filtered, and concentrated under reduced pressure. The resulting brown oily solid is purified by chromatography over silica, eluting with a gradient of 15-40% hexanes/(10% MTBE in DCM). The collected fractions containing desired product are combined and concentrated under reduced pressure, and the resulting residue is triturated with MTBE (15 mL). The resulting solid is collected by filtration and dried under vacuum to afford the title compound (2.75 g, 66% yield). $^1$H NMR (400.1 MHz, DMSO-d$_6$) δ 1.44 (s, 9H), 1.69-1.77 (m, 4H), 2.53-2.65 (m, 4H), 2.91 (br s, 4H), 3.84 (s, 3H), 7.30-7.34 (m, 4H), 7.86 (d, J=8.3 Hz, 2H), 9.80 (br s, 1H), 9.94 (s, 1H). LC-ES/MS (m/z) 569 [M−1].

Preparation 7 methyl 4-[2-[4-[(2-amino-4,5,6,7-tetrahydrobenzothiophene-3-carbonyl)amino]-2,6-difluoro-phenyl]ethyl]benzoate hydrochloride

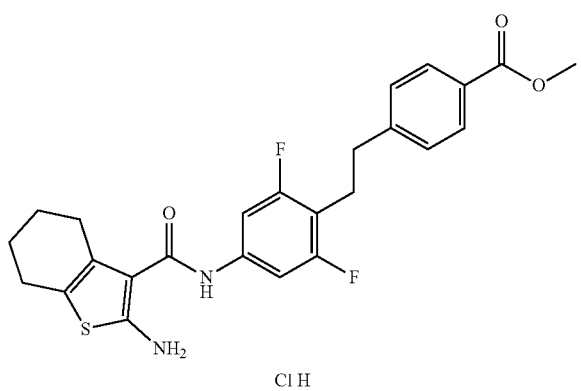 [SMILES: COC(=O)c1ccc(CCc2c(F)cc(NC(=O)c3c(N)sc4c3CCCC4)cc2F)cc1 ; "Cl H"]

A 30 mL scintillation vial is charged with methyl 4-[2-[4-[[2-(tert-butoxycarbonylamino)-4,5,6,7-tetrahydrobenzothiophene-3-carbonyl]amino]-2,6-difluoro-phenyl]ethyl] benzoate (351 mg, 0.61 mmol) and DCM (6 mL). The resulting light yellow solution is degased by passing through a gentle stream of N$_2$. A solution of 4 N HCl in dioxane (155 mL, 6.1 mmol) is added drop wise over 5 min and the resulting solution is stirred at RT for 12 hr. The reaction mixture is concentrated in vacuo and the resulting pale yellow residue is triturated with a minimal amount of DCM. The resulting solid is collected by filtration and dried under vacuum to afford the title compound as an off-white powder (337 mg, 99% yield). $^1$H NMR (399.8 MHz, DMSO-d$_6$) δ 1.73-1.75 (m, 4H), 2.40-2.44 (m, 2H), 2.56-2.59 (m, 2H), 2.85 (s, 4H), 3.80 (s, 3H), 7.26-7.28 (m, 4H), 7.81-7.83 (m, 2H), 9.21 (s, 1H). LC-ES/MS (m/z) 571 [M+1].

Preparation 8 methyl 4-[2-[4-[[2-[[3-(chloromethyl)benzoyl] amino]-4,5,6,7-tetrahydrobenzothiophene-3-carbonyl]amino]-2,6-difluoro-phenyl]ethyl]benzoate

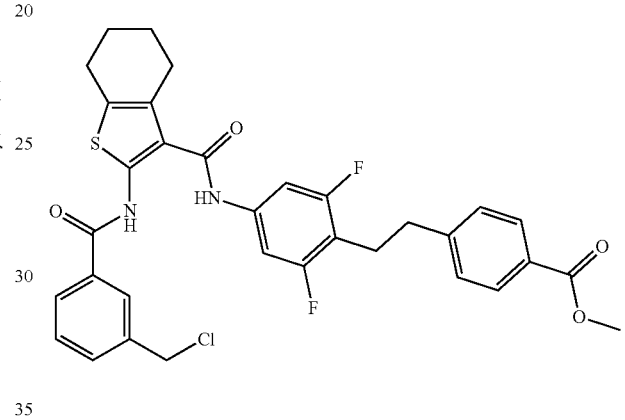

A suspension of methyl 4-[2-[4-[(2-amino-4,5,6,7-tetrahydrobenzothiophene-3-carbonyl)amino]-2,6-difluoro-phenyl]ethyl]benzoate hydrochloride (2.43 g, 4.55 mmol) in DCM (80 mL) in a 250 mL round bottom flask is cooled to 0° C. with an ice/water bath. Pyridine (0.92 mL, 11 mmol) is added drop wise with stirring over 5 min. The resulting pale yellowish solution is stirred for an additional 5 min at 0° C., and a solution of 3-(chloromethyl)benzoyl chloride (0.71 mL, 5.0 mmol) in DCM (20 mL) is added drop wise over 5 min. The reaction mixture is stirred for additional 30 min at 0° C. The reaction mixture is diluted with 150 mL of 10% aqueous citric acid and stirred at RT for 1 hr. The organic layer is separated and the aqueous layer is extracted twice more with DCM (50 mL each). The combined organic extracts are washed sequentially with 5% aqueous NaHCO$_4$, (2×50 mL) and saturated aqueous NaCl (50 mL), dried over anhydrous Na$_2$SO$_4$, filtered, and evaporated to dryness under reduced pressure. The resulting residue is triturated with EtOH (30 mL), and the resulting solid is collected by filtration, washed with EtOH (15 mL), and dried under vacuum to yield the title compound as a tan solid (2.61 g, 92% yield). $^1$H NMR (400.1 MHz, DMSO-d$_6$) δ), 1.73-1.81 (m, 4H), 2.68 (m, 4H), 2.92 (s, 4H), 3.84 (s, 3H), 4.83 (s, 2H), 7.32 (d, J=8.3 Hz, 2H) 7.38-7.344 (m, 2H), 7.56 (t, J=7.7 Hz, 1H), 7.69 (d, J=7.8 Hz, 1H), 7.82 (d, J=7.9 Hz, 1H), 7.87 (d, J=8.2 Hz, 2H), 7.96 (br s, 1H), 10.10 (s, 1H), 11.34 (s, 1H). LC-ES/MS (m/z−) 621 [M−1].

Preparation 9 methyl 4-[2-[2,6-difluoro-4-[[2-[[3-[[4-(4-hydroxybutyl carbamoyl)-2,2-dimethyl-piperazin-1-yl]methyl]benzoyl]amino]-4,5,6,7-tetrahydrobenzothiophene-3-carbonyl]amino]phenyl]ethyl]benzoate

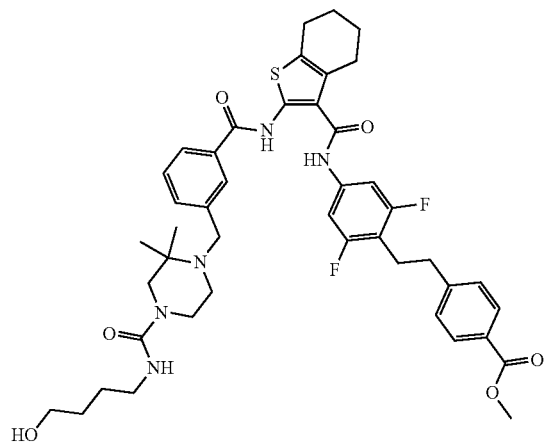 [SMILES: COC(=O)c1ccc(CCc2c(F)cc(NC(=O)c3c(NC(=O)c4cccc(CN5CCN(C(=O)NCCCCO)CC5(C)C)c4)sc4c3CCCC4)cc2F)cc1]

A 2 mL microwave vial is charged with methyl 4-[2-[4-[[2-[[3-(chloromethyl)benzoyl]amino]-4,5,6,7-tetrahydrobenzothiophene-3-carbonyl]amino]-2,6-difluoro-phenyl]ethyl]benzoate (50 mg, 0.08 mmol), N-(4-hydroxybutyl)-3,3-dimethyl-piperazine-1-carboxamide hydrochloride (42.7 mg, 0.16 mmol) and DIPEA (0.056 mL, 0.32 mmol) in a mixture of ACN (1.5 mL) and MeOH (50 µL). The resulting yellow suspension is heated in a BIOTAGE® Initiator microwave synthesizer at 110° C. for 4 hr. The reaction mixture is concentrated in vacuo and the residue is partitioned between 5% aqueous NaHCO$_3$ (75 mL) and DCM (25 mL). The organic layer is separated, the aqueous layer is extracted with twice more with DCM (25 mL each), and the combined organic extracts are washed with saturated aqueous NaCl (25 mL), dried over anhydrous Na$_2$SO$_4$, filtered, and evaporated to dryness under reduced pressure. The resulting residue is purified by reverse phase chromatography over C-18 silica, eluting with a gradient of 0-100% of a mixture of 5% HCOOH in H$_2$O/ACN, to afford the title compound as a light yellow foamy solid (30.2 mg, 46% yield) after solvent evaporation. $^1$H NMR (400.1 MHz, DMSO-d$_6$) δ 1.05 (s, 6H), 1.37-1.44 (m, 4H), 1.80-1.85 (m, 4H), 2.25-2.27 (m, 2H), 2.65-2.677 (m, 4H), 2.91 (br s, 4H), 2.96-3.05 (m, 2H), 3.12 (s, 2H), 3.17-3.26 (m, 2H), 3.35-3.41 (m, 2H), 3.51 (s, 2H), 3.84 (s, 3H), 4.36 (t, J=5.1 Hz, 1H), 6.35-6.39 (m, 1H), 7.32 (d, J=8.3 Hz, 2H), 7.51-7.56 (m, 4H), 7.70-7.80 (m, 1H), 7.87 (m, 3H), 10.01 (br s, 1H), 11.45 (br s, 1H). LC-ES/MS (m/z) 816 [M+1].

Preparation 10 tert-butyl 4-[[3-[[3-[[3,5-difluoro-4-[2-(4-methoxycarbonylphenyl)ethyl]phenyl]carbamoyl]-4,5,6,7-tetrahydrobenzothiophen-2-yl]carbamoyl]phenyl]methyl]-3,3-dimethyl-piperazine-1-carboxylate

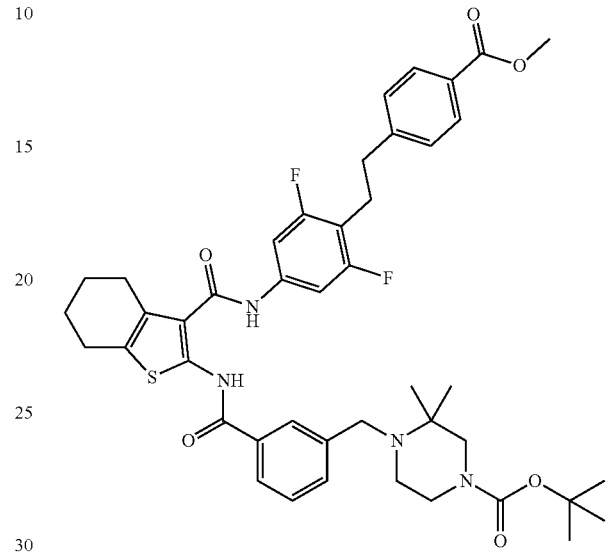

A 20 mL microwave reaction vessel is charged with methyl 4-[2-[4-[[2-[[3-(chloromethyl)benzoyl]amino]-4,5,6,7-tetrahydrobenzothiophene-3-carbonyl]amino]-2,6-difluoro-phenyl]ethyl]benzoate (1.85 g, 2.97 mmol), tert-butyl 3,3-dimethylpiperazine-1-carboxylate (0.91 g, 4.16 mmol), and DIPEA (2.07 mL, 11.9 mmol) in 15 mL of ACN. The resulting yellow suspension is heated in a BIOTAGE® Initiator microwave synthesizer at 110° C. for 4 hr. The reaction mixture is concentrated in vacuo and the residue is partitioned between 5% aqueous NaHCO$_3$ (150 mL) and DCM (50 mL). The organic layer is separated, the aqueous layer is extracted with DCM (2×25 mL). The combined organic layers are washed with saturated aqueous NaCl (50 mL), dried over anhydrous Na$_2$SO$_4$, filtered, and concentrated to dryness under reduced pressure. The resulting residue is purified by chromatography over silica, eluting with a gradient of 0-100% of a mixture of 9:1 DCM/acetone in hexane, to afford the title compound as a yellow solid (1.63 g, 69% yield) after solvent evaporation. $^1$H NMR (400.1 MHz, DMSO-ds) δ 1.04 (s, 6H), 1.38 (s, 9H), 1.81-1.74 (m, 4H), 2.28 (t, J=5.0 Hz, 2H), 2.70 (br s, 4H), 2.91 (s, 4H), 3.13 (s, 2H), 3.26 (s, 2H), 3.52 (s, 2H), 3.84 (s, 3H), 7.31 (d, J=8.3 Hz, 2H), 7.44-7.39 (m, 2H), 7.55-7.46 (m, 2H), 7.75 (d, J=7.6 Hz, 1H), 7.87 (m, 3H), 9.99 (s, 1H), 11.49 (s, 1H). LC-ES/MS (m/z) 801 [M+1].

Preparation 11 methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride

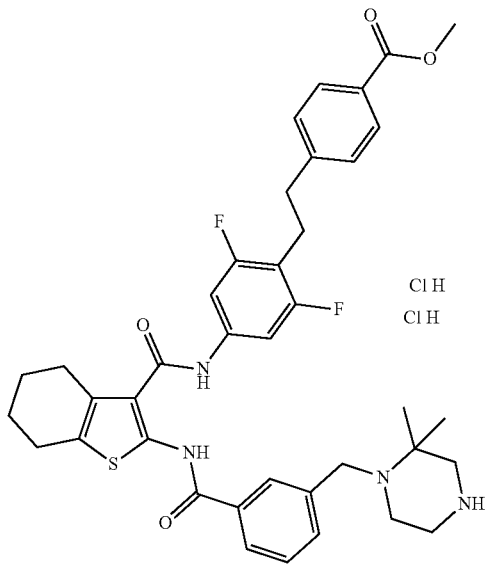 [SMILES: COC(=O)c1ccc(CCc2c(F)cc(NC(=O)c3c(NC(=O)c4cccc(CN5CCNCC5(C)C)c4)sc4c3CCCC4)cc2F)cc1 ; "Cl H" ; "Cl H"]

A solution of tert-butyl 4-[[3-[[3-[[3,5-difluoro-4-[2-(4-methoxycarbonylphenyl)ethyl]phenyl]carbamoyl]-4,5,6,7-tetrahydrobenzothiophen-2-yl]carbamoyl]phenyl]methyl]-3,3-dimethyl-piperazine-1-carboxylate (1.13 g, 1.41 mmol) in DCM (14.1 mL) is stirred at RT and 4 N HCl in dioxane (3.5 mL, 14.1 mmol) is added via syringe. Upon complete addition, the reaction is stirred at RT overnight and concentrated to dryness under reduced pressure. The solid is triturated with DCM/Et$_2$O, the resulting precipitate is collected via vacuum filtration, and the filter cake is dried in a vacuum oven at 50° C. to afford the title compound as a white solid (0.93 g, 1.20 mmol, 85% yield). LC-ES/MS (m/z) 701 [M+1].

Preparation 12 methyl 4-[2-[4-[[2-[[3-[[4-[bis(2-methoxyethyl)sulfamoyl]-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoate

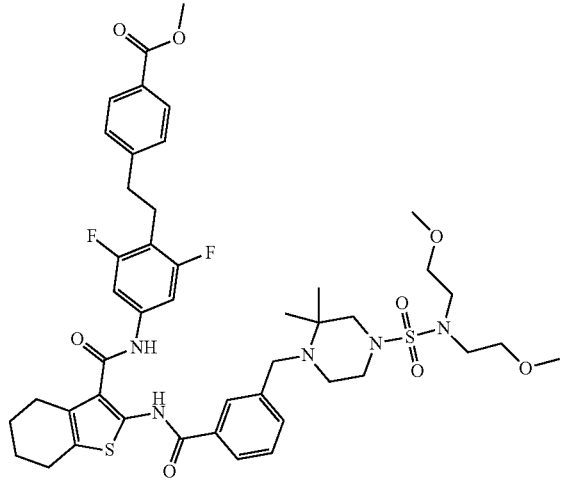 [SMILES: COCCN(CCOC)S(=O)(=O)N1CCN(Cc2cccc(C(=O)Nc3sc4c(c3C(=O)Nc3cc(F)c(CCc5ccc(C(=O)OC)cc5)c(F)c3)CCCC4)c2)C(C)(C)C1]

To a solution of methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride (190.8 mg, 0.24 mmol) and TEA (0.165 mL, 1.18 mmol) in 4 mL of THF, bis(2-methoxyethyl)sulfamoyl chloride (87 mg, 0.36 mmol) in 4 mL of THF is added drop wise. The resulting mixture is heated to 50° C. for 18 hr. After cooling to RT, the reaction mixture is diluted with a mixture of 5% aqueous NaHCO$_3$ (75 mL) and DCM (25 mL). The layers are separated, and the aqueous layer is washed with additional DCM (2×25 mL). The organic extracts are combined, washed with saturated aqueous NaCl (25 mL), dried over anhydrous Na$_2$SO$_4$, filtered, and concentrated under reduced pressure. The resulting residue is purified by chromatography over silica, eluting with a gradient of 10-30% of a mixture of acetone in hexanes, to afford the desired product as a light yellow solid (150.1 mg, 70.8% yield) after solvent evaporation. $^1$H NMR (400.1 MHz, DMSO-d$_6$) δ 1.13 (s, 6H), 1.85-1.70 (m, 4H), 2.43-2.36 (m, 2H), 2.75-2.65 (m, 4H), 3.03-2.86 (m, 8H), 3.24 (s, 6H), 3.36-3.32 (m, 4H), 3.44 (t, J=5.8 Hz, 4H), 3.54 (s, 2H), 3.84 (s, 3H), 7.32 (d, J=8.3 Hz, 2H), 7.52-7.38 (m, 3H), 7.56 (d, J=7.6 Hz, 1H), 7.74 (d, J=7.6 Hz, 1H), 7.91-7.84 (m, 3H), 10.00 (s, 1H), 11.47 (s, 1H). LC-ES/MS (m/z) 896 [M+1].

Preparation 13 methyl 4-[2-[2,6-difluoro-4-[[2-[[3-[[4-(4-methoxy-4-oxo-butyl)-2,2-dimethyl-piperazin-1-yl]methyl]benzoyl]amino]-4,5,6,7-tetrahydrobenzothiophene-3-carbonyl]amino]phenyl]ethyl]benzoate

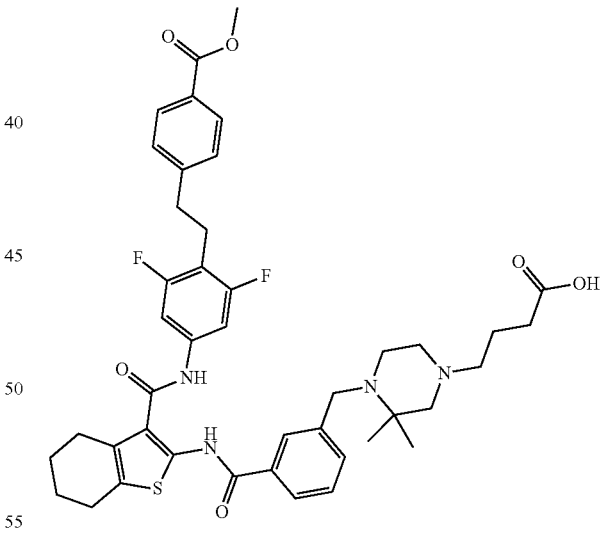

To a solution of methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride (148.4 mg, 0.1688 mmol), DIPEA (60 µL, 0.34 mmol) and 4-oxobutanoic acid methyl ester (40 mg, 0.34 mmol) in 4 mL of DCM is added AcOH (0.01 mL), followed by sodium triacetoxyborohydride (0.073 g, 0.34 mmol). The resulting reaction mixture is allowed to stir at RT for 12 hr. The reaction mixture is diluted with a mixture of 5% aqueous NaHCO$_3$ (75 mL) and DCM (25 mL). The layers are separated, and the aqueous layer is washed with additional DCM (2×25 mL). The organic extracts are combined, washed with saturated aqueous NaCl (25 mL), dried over anhydrous Na₂SO₄, filtered, and concentrated under reduced pressure. The resulting residue is purified by chromatography over silica, using a gradient of 35-40% of a mixture of 9:1 EtOH/DCM in hexane, to afford the desired product as a light yellow solid (132.1 mg, 91.8% yield) after solvent evaporation. ¹H NMR (400.1 MHz, DMSO-$d_6$) δ 1.09 (s, 6H), 1.70-1.58 (m, 2H), 1.87-1.70 (m, 4H), 2.20-2.09 (m, 2H), 2.36-2.27 (m, 4H), 2.63-2.54 (m, 2H), 2.75-2.64 (m, 4H), 2.92 (s, 4H), 3.30-3.28 (m, 2H), 3.65-3.53 (m, 5H), 3.84 (s, 3H), 7.32 (d, J=8.3 Hz, 2H), 7.58-7.37 (m, 4H), 7.72-7.69 (m, 1H), 7.91-7.83 (m, 3H), 9.99 (s, 1H), 11.45 (s, 1H). LC-ES/MS (m/z) 801 [M+1].

Preparation 14 methyl 4-[2-[2,6-difluoro-4-[[2-[[3-[[4-(3-methoxypropyl)-2,2-dimethyl-piperazin-1-yl]methyl]benzoyl]amino]-4,5,6,7-tetrahydrobenzothiophene-3-carbonyl]amino]phenyl]ethyl]benzoate

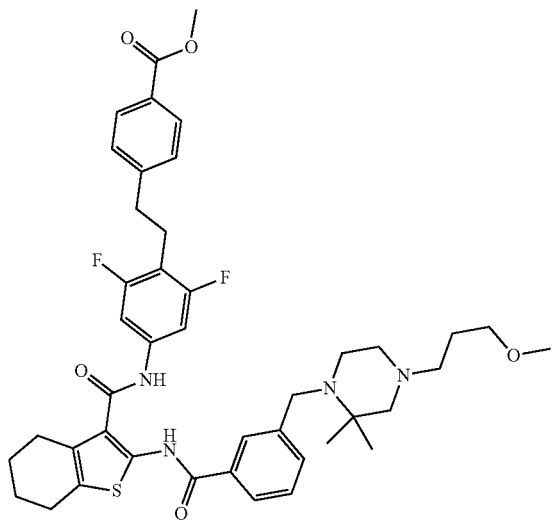 [SMILES: COCCCN1CCN(Cc2cccc(C(=O)Nc3sc4c(c3C(=O)Nc3cc(F)c(CCc5ccc(C(=O)OC)cc5)c(F)c3)CCCC4)c2)C(C)(C)C1]

To a solution of methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride (0.108 g, 0.13 mmol), 3-methoxypropionaldehyde (0.023 g, 0.25 mmol), and DIPEA (0.043 mL, 0.25 mmol) in 4 mL of DCM, AcOH (0.01 mL) is added, followed by sodium triacetoxyborohydride (0.053 g, 0.25 mmol). The resulting reaction mixture is stirred at RT for 12 hr. The reaction mixture is diluted with of 5% aqueous NaHCO₃ (75 mL) and of DCM (25 mL). The layers are separated, and the aqueous layer is washed with additional DCM (2×25 mL). The organic extracts are combined, washed with saturated aqueous NaCl (25 mL), dried over anhydrous Na₂SO₄, filtered, and concentrated under reduced pressure. The resulting residue is purified by chromatography over silica, using a gradient of 25-80% acetone in hexane, to afford the desired product as a light yellow solid (26.2 mg, 27.6% yield) after solvent evaporation. ¹H NMR (400.1 MHz, DMSO-$d_6$) δ 11.44 (m, 1H), 9.98 (m, 1H), 7.92-7.82 (m, 3H), 7.76-7.70 (m, 1H), 7.57-7.38 (m, 4H), 7.36-7.27 (m, 2H), 3.84 (s, 4H), 3.27-3.16 (m, 2H), 2.97-2.87 (m, 4H), 2.76-2.64 (m, 4H), 2.37-2.28 (m, 2H), 2.25-2.15 (m, 2H), 1.90-1.71 (m, 4H), 1.67-1.54 (m, 2H), 1.09 (s, 6H). LC-ES/MS (m/z) 773 [M+1].

Preparation 15 methyl 4-[2-[4-[[2-[[3-[[4-[2-(tert-butoxycarbonylamino)acetyl]-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoate

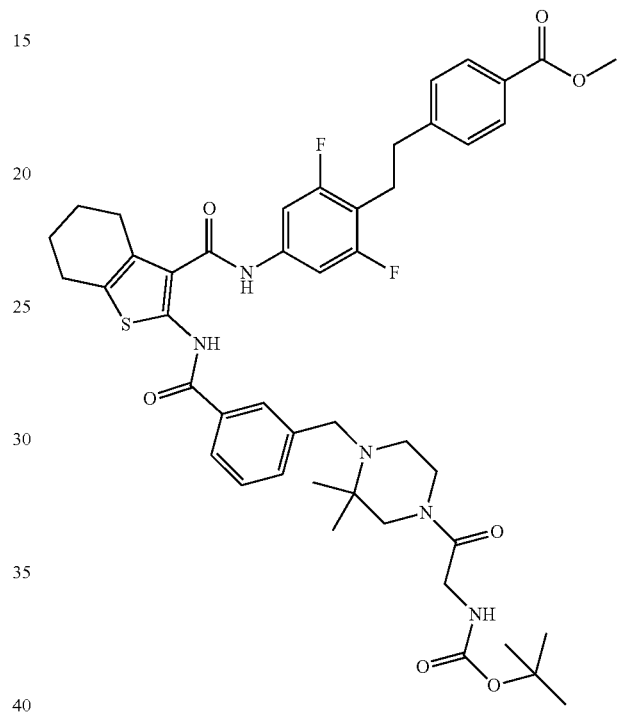

To a round bottom flask is added methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride (500 mg, 1.4 mmol), DMF (25 mL), and 1,8-diazabicyclo [5.4.0]undec-7-ene (0.19 mL, 1.27 mmol). The mixture is stirred briefly and treated with HOBT (103 mg, 0.67 mmol), EDCI (250 mg, 1.6 mmol), and N-(tert-butoxycarbonyl)glycine (132 mg, 0.75 mmol). The mixture is stirred at RT for 18 hours. The mixture is diluted with water (25 mL) and the resulting slurry is stirred at RT for 3 hr. The resulting light yellow solid is collected by filtration, washed with water, and air-dried. The resulting powder is dissolved in DCM, dried over anhydrous MgSO₄, filtered, and concentrated under reduced pressure. The residue is purified by chromatography over silica, eluting with 15% EtOAc in DCM for 20 min then 25% EtOAc in DCM, to afford the title compound (451 mg, 38% yield) after solvent evaporation. ¹H NMR (400.13 MHz, DMSO) δ 11.52-11.46 (m, 1H), 9.99 (s, 1H), 7.90-7.86 (m, 3H), 7.76-7.74 (m, 1H), 7.57-7.55 (m, 1H), 7.52-7.47 (m, 1H), 7.44-7.39 (m, 2H), 7.33 (d, J=7.6 Hz, 2H), 6.76-6.71 (m, 1H), 3.84 (s, 3H), 3.81-3.76 (m, 2H), 3.57-3.54 (m, 2H), 3.43-3.38 (m, 2H), 3.32 (s, 12H, water), 3.28-3.22 (m, 2H), 2.91 (s, 4H), 2.70 (s, 4H), 2.51-2.50 (m, 16H, DMSO), 2.39-2.35 (m, 2H), 1.87-1.81 (m, 4H), 1.40-

1.35 (m, 10H), 1.29-1.25 (m, 1H), 1.07 (d, J=21.1 Hz, 6H). LC-ES/MS (m/z) 858 [M+1].

Preparation 16 methyl 4-[2-[2,6-difluoro-4-[[2-[[3-[[4-(4-methoxy-butylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoate

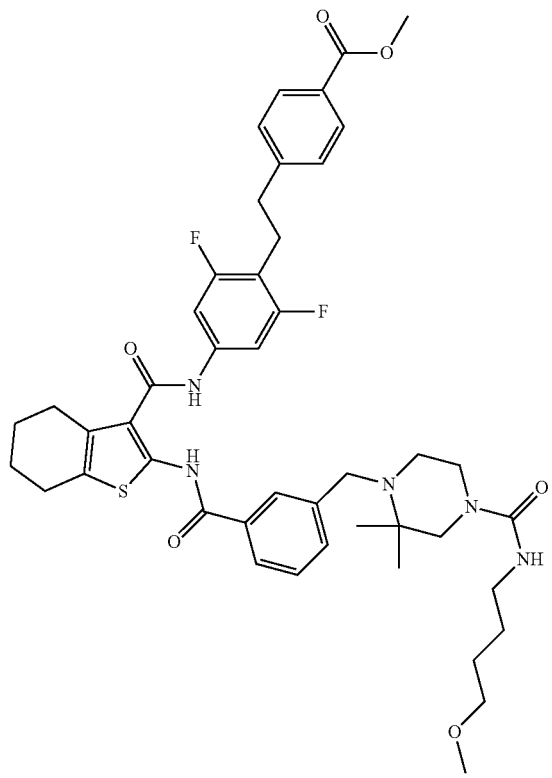 [SMILES: COCCCCNC(=O)N1CCN(Cc2cccc(C(=O)Nc3sc4c(c3C(=O)Nc3cc(F)c(CCc5ccc(C(=O)OC)cc5)c(F)c3)CCCC4)c2)C(C)(C)C1]

In a 30 mL scintillation vial, a solution of methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride (120 mg, 0.155 mmol) and TEA (63 mg, 0.62 mmol) in DCM (3 mL) is stirred at RT as a solution of 1-isocyanato-4-methoxy-butane (30 mg, 0.23 mmol) in DCM (1 mL) is added via syringe. The resulting reaction mixture is allowed to stir at RT for 4 hours. The reaction mixture is concentrated under reduced pressure and purified by chromatography over silica, eluting with a gradient of 0-100% EtOAc/hexanes, to afford the title compound as a tan foam (102 mg, 790/% yield) after solvent evaporation. $^1$H NMR (400.1 MHz, DMSO-d$_6$) δ 1.03 (s, 6H), 1.35-1.45 (m, 4H), 1.68-1.82 (m, 4H), 2.21-2.25 (m, 2H), 2.63-2.70 (m, 4H), 2.89 (s, 4H), 2.95-3.02 (m, 2H), 3.095 (s, 2H), 3.18 (s, 3H); 3.15-3.22 (m, 2H), 3.25-3.30 (m, 2H), 3.48 (s, 2H), 3.815 (s, 3H), 6.334 (t, J=5.5 Hz, 1H), 7.30 (d, J=7.9 Hz, 2H), 7.35-7.42 (m, 2H), 7.42-7.50 (m, 1H), 7.50-7.55 (m, 1H), 7.71 (d, J=7.6 Hz, 1H), 7.83-7.89 (m, 3H), 9.981 (s, 1H), 11.44 (s, 1H). LC-ES/MS (m/z) 830 [M+1].

Preparation 17

4-[2-[4-[[2-[[3-[(4-tert-butoxycarbonyl-2,2-dimethyl-piperazin-1-yl)methyl]benzoyl]amino]-4,5,6,7-tetrahydrobenzothiophene-3-carbonyl]amino]-2,6-difluoro-phenyl]ethyl]benzoic Acid

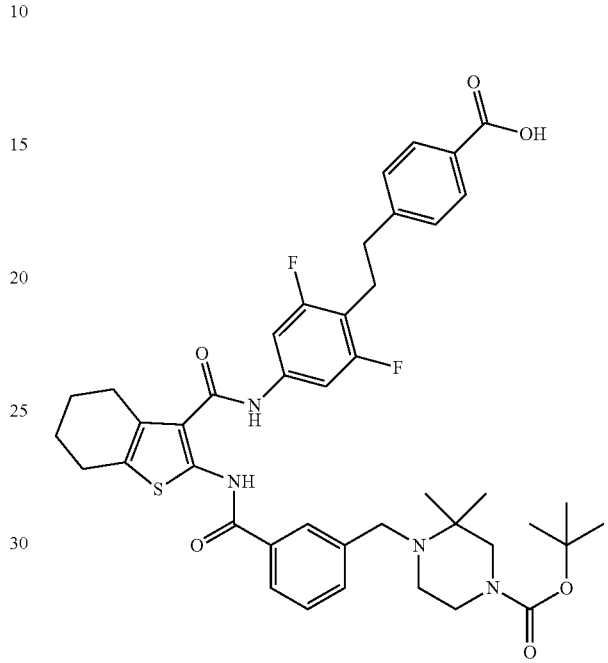

A 60 mL scintillation vial is charged with tert-butyl 4-[[3-[[3-[[3,5-difluoro-4-[2-(4-methoxycarbonylphenyl)ethyl]phenyl]carbamoyl]-4,5,6,7-tetrahydrobenzothiophen-2-yl]carbamoyl]phenyl]methyl]-3,3-dimethyl-piperazine-1-carboxylate (3.92 g, 4.8 mmol), lithium hydroxide (570 mg, 24 mmol), THF (20 mL), MeOH (10 mL) and H$_2$O (10 mL) and the resulting suspension is stirred at RT for 12 hr. The reaction mixture is diluted with H$_2$O (40 mL) and concentrated in vacuo to ~2 volume. The pH of the resulting mixture is adjusted to ~5-6 with 10% aqueous citric acid and the resulting colorless suspension is partitioned between 150 mL of water and 50 mL of 4:1 chloroform/isopropanol. The organic layer is separated, the pH of the aqueous layer is adjusted again to pH~5 with 10% aqueous citric acid, and the mixture is extracted twice with additional 4:1 chloroform/isopropanol (2×50 mL). The organic layers are combined, washed with saturated aqueous NaCl, dried over anhydrous Na$_2$SO$_4$, filtered, and the filtrate is concentrated under reduced pressure to give the title compound (3.7 g, >99% yield) as an off-white solid that may be used in the subsequent step without additional purification. LC-ES/MS (m/z) 787 [M+1].

Preparation 18 tert-butyl 4-[[3-[[3-[[4-[2-(4-carbamoylphenyl)ethyl]-3,5-difluoro-phenyl]carbamoyl]-4,5,6,7-tetrahydrobenzothiophen-2-yl]carbamoyl]phenyl]methyl]-3,3-dimethyl-piperazine-1-carboxylate

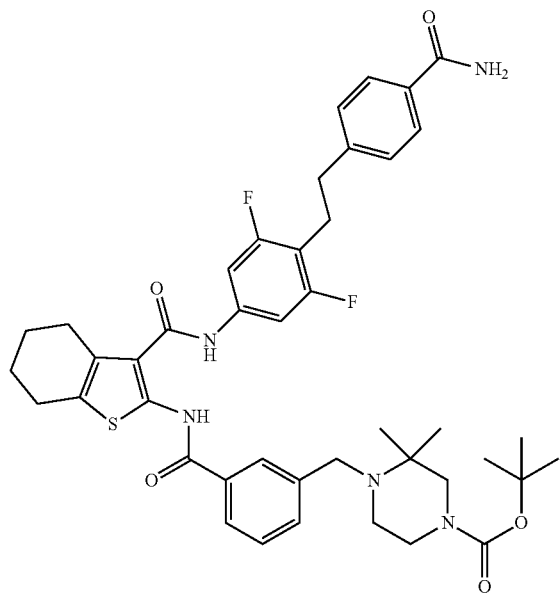 [SMILES: CC(C)(C)OC(=O)N1CCN(Cc2cccc(C(=O)Nc3sc4c(c3C(=O)Nc3cc(F)c(CCc5ccc(C(N)=O)cc5)c(F)c3)CCCC4)c2)C(C)(C)C1]

A 500 mL round bottom flask is charged with a solution of 4-[2-[4-[[2-[[3-[(4-tert-butoxycarbonyl-2,2-dimethyl-piperazin-1-yl)methyl]benzoyl]amino]-4,5,6,7-tetrahydrobenzothiophene-3-carbonyl]amino]-2,6-difluoro-phenyl]ethyl]benzoic acid (3.50 g, 4.45 mmol) and DIPEA (3.1 mL, 17.8 mmol) in DCM (75 mL). To this solution solid bis(2-oxo-3-oxazolidinyl)phosphinic chloride (1.4 g, 5.3 mmol) is added in small portions over 10 min and the resulting suspension is stirred at RT for 10 min. A 0.5 M solution of NH₃ in 1,4-dioxane (40 mL, 22.25 mmol) is added in one portion and the resulting suspension is stirred for 2 h at RT. Additional bis(2-oxo-3-oxazolidinyl)phosphinic chloride (0.7 g, 2.7 mmol) is added in small portions over 5 min and the resulting suspension is left to stir for 12 h at RT. Additional bis(2-oxo-3-oxazolidinyl)phosphinic chloride (0.7 g, 2.7 mmol) is again added in small portions over 5 min and the resulting suspension is left to stir for 12 h at RT. The resulting reaction mixture is partitioned between 300 mL of 5% aqueous NaHCO₃ and 50 mL of DCM. The layers are separated, and the aqueous layer is extracted twice with additional DCM (2×100 mL). The combined organic layers are washed with saturated aqueous NaCl, dried over anhydrous Na₂SO₄, filtered, and concentrated to dryness in vacuo. The resulting yellow foamy residue is purified by chromatography over silica, eluting with a gradient of 10-12% acetone/DCM; the mobile phase is then switched to 35% MeOH/DCM. The collected fractions containing desired product are combined and concentrated under reduced pressure and the residue is triturated with DCM. The resulting solid is collected by filtration and dried under vacuum to afford the title compound. The trituration filtrate is recovered and evaporated to dryness in vacuo. The resulting residue is purified by chromatography over silica, eluting with a gradient of 5-10%° MeOH in DCM and the collected fractions containing desired product are combined and evaporated and added to the material obtained from the first purification to give the title compound as a light yellow solid (2.43 g, 70%° yield). ¹H NMR (400.1 MHz, DMSO-d₆) δ 1.05 (s, 6H), 1.39 (s, 9H), 1.68-1.90 (m, 4H), 2.29 (m, 2H), 2.70 (m, 4H), 2.89 (m, 4H), 3.14 (s, 2H), 3.28 (s, 2H), 3.51 (s, 2H), 7.16-7.34 (m, 3H), 7.36-7.58 (m, 4H), 7.68-7.73 (m, 3H), 7.90 (m, 2H), 10.00 (s, 1H), 11.49 (s, 1H). LC-ES/MS (m/z) 786 [M+1].

Preparation 19

N-[4-[2-(4-carbamoylphenyl)ethyl]-3,5-difluoro-phenyl]-2-[[3-[(2,2-dimethylpiperazin-1-yl)methyl]benzoyl]amino]-4,5,6,7-tetrahydrobenzothiophene-3-carboxamide dihydrochloride

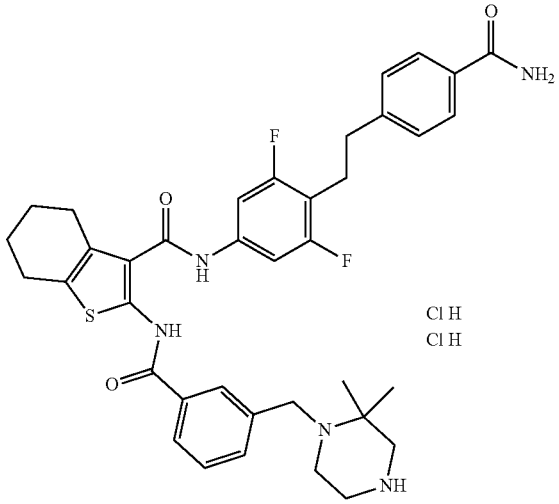 [SMILES: CC1(C)CNCCN1Cc1cccc(C(=O)Nc2sc3c(c2C(=O)Nc2cc(F)c(CCc4ccc(C(N)=O)cc4)c(F)c2)CCCC3)c1 ; "Cl H" ; "Cl H"]

A solution of tert-butyl 4-[[3-[[3-[[4-[2-(4-carbamoylphenyl)ethyl]-3,5-difluoro-phenyl]carbamoyl]-4,5,6,7-tetrahydrobenzothiophen-2-yl]carbamoyl]phenyl]methyl]-3,3-dimethyl-piperazine-1-carboxylate (2.43 g, 3.1 mmol) in a mixture of DCM (80 mL) and MeOH (8 mL) in a 250 mL round-bottom flask is thoroughly degassed under nitrogen, and a 4 N solution of HCl in 1,4-dioxane (16 mL, 62 mmol) is added drop wise over 10 min. The resulting solution is stirred for 12 h at RT. Volatiles are removed in vacuo to give the title compound as a yellow, hygroscopic solid (2.45 g, >99%) which may be used in the next step without further purification.

Preparation 20 methyl 4-[2-[2,6-difluoro-4-[[2-[[3-[(2,2,4-trimethylpiperazin-1-yl)methyl]benzoyl]amino]-4,5,6,7-tetrahydrobenzothiophene-3-carbonyl]amino]phenyl]ethyl]benzoate

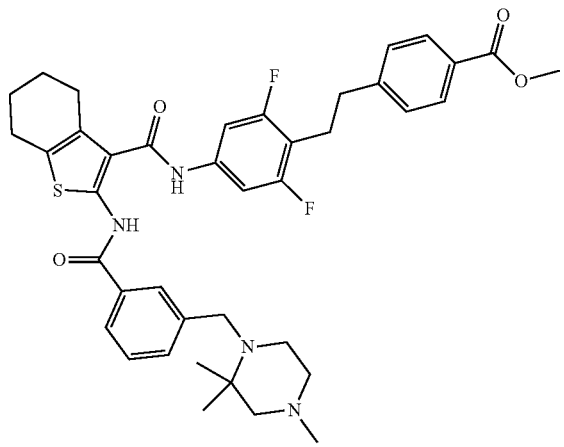 [SMILES: COC(=O)c1ccc(CCc2c(F)cc(NC(=O)c3c(NC(=O)c4cccc(CN5CCN(C)CC5(C)C)c4)sc4c3CCCC4)cc2F)cc1]

A 5 mL microwave reaction vessel is charged with methyl 4-[2-[4-[[2-[[3-(chloromethyl)benzoyl]amino]-4,5,6,7-tetrahydrobenzothiophene-3-carbonyl]amino]-2,6-difluorophenyl]ethyl]benzoate (225 mg, 361 mmol) and a solution of 1,3,3-trimethylpiperazine (65 mg, 0.488 mmol) and DIPEA (0.25 mL, 1.4 mmol) in 3 mL of ACN. The resulting yellow suspension is heated in a BIOTAGE® Initiator microwave synthesizer at 110° C. for 3 hr. The reaction mixture is concentrated in vacuo and the residue is partitioned between 5% aqueous NaHCO$_3$ (75 mL) and DCM (25 mL). The organic layer is separated, the aqueous layer is extracted with DCM (2×25 mL). The combined organic layers are washed with saturated aqueous NaCl (25 mL), dried over anhydrous Na$_2$SO$_4$, filtered, and concentrated to dryness under reduced pressure. The resulting residue is purified by chromatography over silica, eluting with a gradient of 20-50% of a mixture of 10% 7N NH$_3$/MeOH in dcm in MTBE, to afford the title compound as a light yellow solid (195 mg, 760/% yield) after solvent evaporation. $^1$H NMR (400.1 MHz, DMSO-d$_6$): δ 1.11 (two s, 6H). 1.90-1.64 (m, 4H), 2.25-1.94 (m, 4H), 2.40-2.26 (m, 2H), 2.50 (under residual dmso resonance, 3H), 2.79-2.60 (br s, 4H), 2.92 (s, 4H), 3.77-3.76 (br, 2H), 3.84 (s, 3H), 7.32 (m, 2H), 7.60-7.36 (m, 4H), 7.79-7.67 (m, 1H), 7.87 (m, 3H), 9.99 (s, 1H), 11.46 (s, 1H). LC-ES/MS (m/z) 715 [M+1].

Preparation 21 tert-butyl 4-[(3-methoxy-3-oxo-propyl)carbamoyl]-2,2-dimethyl-piperazine-1-carboxylate

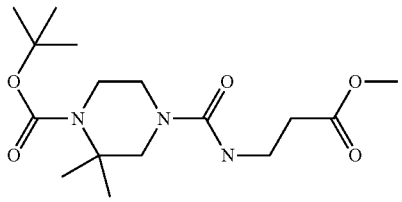 [SMILES: COC(=O)CCNC(=O)N1CCN(C(=O)OC(C)(C)C)C(C)(C)C1]

20 mL scintillation vial is charged with a solution of tert-butyl 2,2-dimethylpiperazine-1-carboxylate (500 mg, 2.29 mmol) in DCM (12 mL) and cooled down in ice bath. While cooling DIPEA (1.20 mL, 6.86 mmol) is added followed by a solution of methyl 3-isocyanatopropanoate (404 mg, 2.97 mmol) in DCM (3 mL) added dropwise over 5 min. The resulting mixture is allowed to warm up to rt and stirred at rt for 15 min. The rxn mixture is diluted with 5% aqueous citric acid (100 mL) and DCM (25 mL), and the layers are separated. The aqueous layer is extracted with DCM (2×25 mL). The organic extracts are combined, washed with saturated aqueous NaCl (25 mL), dried over anhydrous Na$_2$SO$_4$, filtered, and concentrated under reduced pressure. The resulting residue is purified by chromatography over silica, eluting with a gradient of 30-53% of acetone in hexanes, to afford the title compound as a colorless thick oil (726 mg, material contains ~10% of residual DCM, 83% yield) after solvent evaporation. $^1$H NMR (399.8 MHz, CDCl$_3$): δ 1.34 (s, 6H), 1.45 (s, 9H), 2.58-2.48 (m, 2H), 3.37 (t, J=5.7 Hz, 2H), 3.54-3.43 (m, 4H), 3.75-3.62 (m, 5H), 5.08-4.99 (m, 1H). LC-ES/MS (m/z) 344 [M+1].

Preparation 22 methyl 3-[(3,3-dimethylpiperazine-1-carbonyl)amino]propanoate hydrochloride

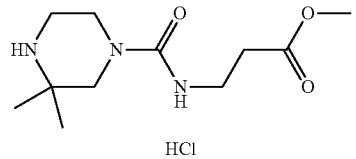

HCl

To a 20 mL scintillation vial containing a solution of tert-butyl 4-[(3-methoxy-3-oxo-propyl)carbamoyl]-2,2-dimethyl-piperazine-1-carboxylate (250 mg, 0.65 mmol) in DCM (7 mL), 4 N hydrochloric acid in dioxane (1.63 mL, 6.54 mmol) is added dropwise with stirring. The resulting suspension is stirred at rt for 1 hr, concentrated in vacuo and the residue is dried under vacuum to obtain the title compound as white hygroscopic solid which is used in the next step without as it is. LC-ES/MS (m/z) 244 [M+1].

Preparation 23 methyl 4-[2-[2,6-difluoro-4-[[2-[[3-[[4-[(3-methoxy-3-oxo-propyl)carbamoyl]-2,2-dimethyl-piperazin-1-yl]methyl]benzoyl]amino]-4,5,6,7-tetrahydrobenzothiophene-3-carbonyl]amino]phenyl]ethyl]benzoate

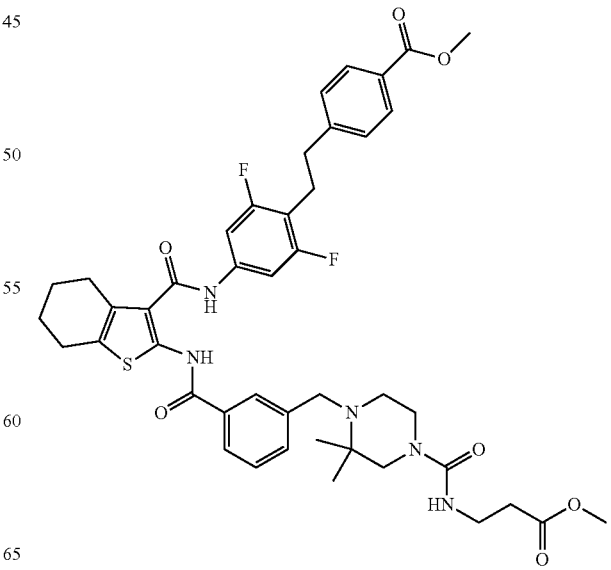

A 5 mL microwave reaction vessel is charged with methyl 4-[2-[4-[[2-[[3-(chloromethyl)benzoyl]amino]-4,5,6,7-tetrahydrobenzothiophene-3-carbonyl]amino]-2,6-difluorophenyl]ethyl]benzoate (180 mg, 0.29 mmol), a solution of methyl 3-[(3,3-dimethylpiperazine-1-carbonyl)amino]propanoate hydrochloride (162 mg, 0.58 mmol) and N,N-DIPEA (0.202 mL, 1.16 mmol) in a mixture of 3 mL of ACN and 0.5 mL of MeOH. The resulting yellow suspension is heated in a BIOTAGE® Initiator microwave synthesizer at 110° C. for 3 hr. The reaction mixture is concentrated in vacuo and the residue is partitioned between 5% aqueous $NaHCO_3$ (75 mL) and DCM (25 mL). The organic layer is separated; the aqueous layer is extracted with DCM (2×25 mL). The combined organic layers are washed with saturated aqueous NaCl (25 mL), dried over anhydrous $Na_2SO_4$, filtered, and concentrated to dryness under reduced pressure. The resulting residue is purified by chromatography over C-18 silica, eluting with a gradient of 15-80% of a mixture of 0.1% formic acid/ACN in 0.1% formic acid/$H_2O$ for 15 minutes, to obtain the title compound as a pale orange solid (81 mg, 34% yield) after solvent evaporation. LC-ES/MS (m/z) 830 [M+1].

Preparation 24 tert-butyl 3-[[3-[[3-[[3,5-difluoro-4-[2-(4-methoxycarbonylphenyl)ethyl]phenyl]carbamoyl]-4,5,6,7-tetrahydrobenzothiophen-2-yl]carbamoyl]phenyl]methyl]-3,8-diazabicyclo[3.2.1]octane-8-carboxylate

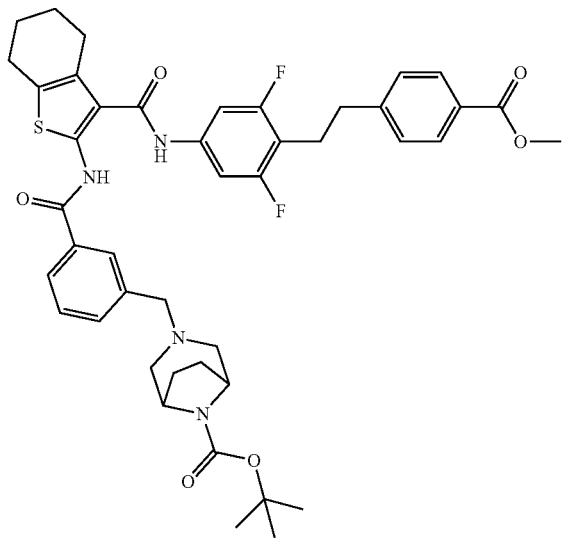 [SMILES: COC(=O)c1ccc(CCc2c(F)cc(NC(=O)c3c(NC(=O)c4cccc(CN5CC6CCC(C5)N6C(=O)OC(C)(C)C)c4)sc4c3CCCC4)cc2F)cc1]

A 20 mL microwave reaction vessel is charged with methyl 4-[2-[4-[[2-[[3-(chloromethyl)benzoyl]amino]-4,5,6,7-tetrahydrobenzothiophene-3-carbonyl]amino]-2,6-difluoro-phenyl]ethyl]benzoate (1.80 g, 2.89 mmol) and a solution of tert-butyl 3,8-diazabicyclo [3.2.1]octane-8-carboxylate (760 mg, 3.47 mmol) and DIPEA (1.01 mL, 5.78 mmol) in ACN (12 mL). The resulting yellow suspension is heated in a BIOTAGE® Initiator microwave synthesizer at 110° C. for 1 hr. The reaction mixture is concentrated in vacuo and the residue is partitioned between 5% aqueous $NaHCO_3$ (150 mL) and DCM (50 mL). The organic layer is separated, the aqueous layer is extracted with DCM (2×50 mL). The combined organic layers are washed with saturated aqueous NaCl (50 mL), dried over anhydrous $Na_2SO_4$, filtered, and concentrated to dryness under reduced pressure. The resulting residue is purified by chromatography over silica, eluting with a gradient of 15-45% of EtOAc in hexanes to afford the title compound as a light yellow solid (2.23 g, 97% yield) after solvent evaporation. $^1$H NMR (400.1 MHz, DMSO-$d_6$): δ 1.38 (s, 9H), 1.95-1.60 (m, 8H), 2.16 (d, J=10.0 Hz, 2H), 2.57 (d, J=10.0 Hz, 1H), 2.70 (br s, 4H), 2.92 (s, 4H), 3.51 (s, 2H), 3.84 (s, 3H), 4.08-3.96 (m, 2H), 7.35-7.26 (m, 2H), 7.45-7.35 (m, 2H), 7.58-7.45 (m, 2H), 7.79-7.72 (m, 1H), 7.92-7.79 (m, 3H), 10.00 (s, 1H), 11.41 (s, 1H). LC-ES/MS (m/z) 799 [M+1].

Preparation 25 methyl 4-[2-[4-[[2-[[3-(3,8-diazabicyclo[3.2.1]octan-3-ylmethyl)benzoyl]amino]-4,5,6,7-tetrahydrobenzothiophene-3-carbonyl]amino]-2,6-difluorophenyl]ethyl]benzoate dihydrochloride

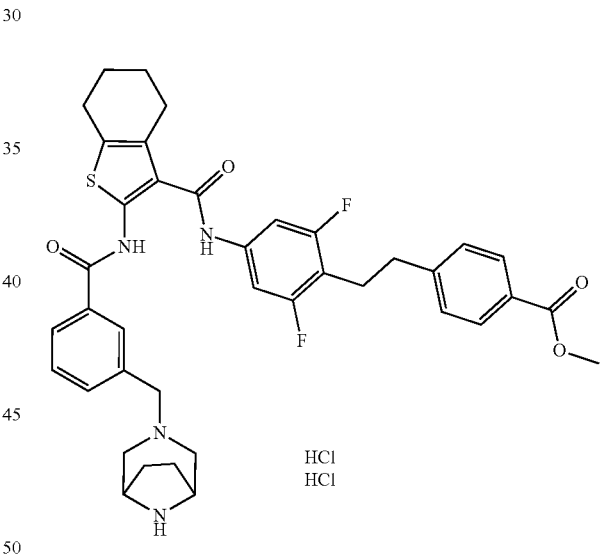

Under $N_2$, to a 250 mL RBF containing a solution tert-butyl 3-[[3-[[3-[[3,5-difluoro-4-[2-(4-methoxycarbonylphenyl)ethyl]phenyl]carbamoyl]-4,5,6,7-tetrahydrobenzothiophen-2-yl]carbamoyl]phenyl]methyl]-3,8-diazabicyclo[3.2.1]octane-8-carboxylate (2.23 g, 2.79 mmol) in DCM (45 mL), 4 N hydrochloric acid in dioxane (7.0 mL, 28 mmol) is added dropwise with stirring. The resulting suspension is stirred at rt for 12 hr, concentrated in vacuo and the residue is dried under vacuum to afford the title compound as light yellowish solid which is used in the next step without further purification. LC-ES/MS (m/z) 699 [M+1].

Preparation 26 methyl 4-[2-[2,6-difluoro-4-[[2-[[3-[[8-(methylcar-bamoyl)-3,8-diazabicyclo[3.2.1]octan-3-yl]methyl]benzoyl]amino]benzothiophene-3-carbonyl]amino]phenyl]ethyl]benzoate

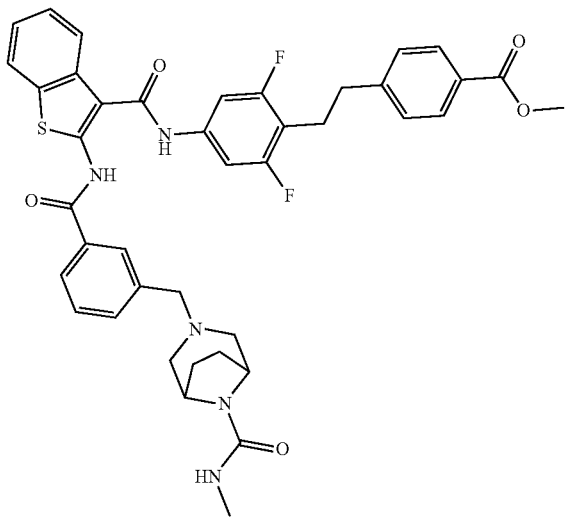 [SMILES: CNC(=O)N1C2CCC1CN(Cc1cccc(C(=O)Nc3sc4ccccc4c3C(=O)Nc3cc(F)c(CCc4ccc(C(=O)OC)cc4)c(F)c3)c1)C2]

20 mL scintillation vial is charged with methyl 4-[2-[4-[[2-[[3-(3,8-diazabicyclo[3.2.1]octan-3-ylmethyl)benzoyl]amino]-4,5,6,7-tetrahydrobenzothiophene-3-carbonyl]amino]-2,6-difluoro-phenyl]ethyl]benzoate dihydrochloride (1.04 g, 1.27 mmol), DCM (8 mL) and TEA (0.89 mL, 6.4 mmol). The resulting suspension is agitated at rt until all solids dissolved. A solution of methylaminoformyl chloride (144 mg, 1.46 mmol) in 2 mL of DCM is added dropwise with stirring and stirring is continued for additional 15 min. The rxn mixture is diluted with 5% aqueous NaHCO$_3$ (150 mL) and DCM (50 mL), and the layers are separated. The aqueous layer is extracted with DCM (2×50 mL). The organic extracts are combined, washed with saturated aqueous NaCl (50 mL), dried over anhydrous Na$_2$SO$_4$, filtered, and concentrated under reduced pressure. The resulting residue is purified by chromatography over C-18 silica, eluting with a gradient of 10-20% of a mixture of 5% MeOH in 10 mM ammonium bicarbonate in ACN over 5 min and 20-80% of a mixture of 5% MeOH in 10 mM ammonium bicarbonate in ACN over 15 minutes, to obtain the title compound as an off-white solid (53 mg, 68% yield) after solvent evaporation. The title compound was isolated as a minor component of the mixture as a yellowish green solid (177 mg, 17% yield). The material is used in the next step without further purification. LC-ES/MS (m/z) 752 [M+1].

Preparation 27 methyl 4-[2-[4-[[2-[[3-[(2,2-dimethylpiperazin-1-yl)methyl]benzoyl]amino]-4,5,6,7-tetrahydrobenzothi-ophene-3-carbonyl]amino]-2,6-difluoro-phenyl]ethyl]benzoate

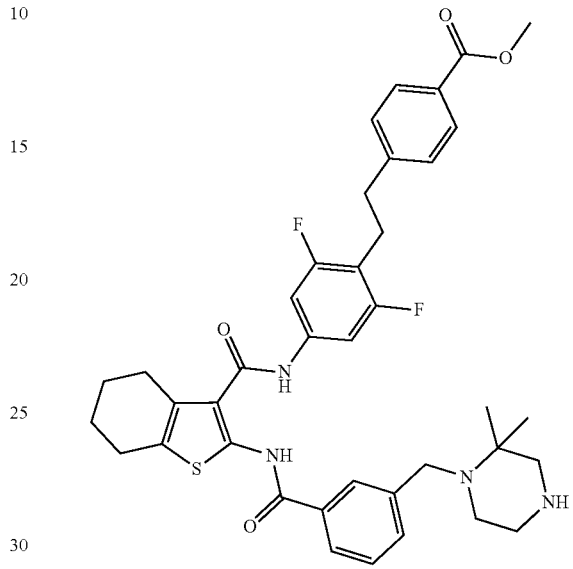

A solution of tert-butyl 4-[[3-[[3-[[3,5-difluoro-4-[2-(4-methoxycarbonyl phenyl)ethyl]phenyl]carbamoyl]-4,5,6,7-tetrahydrobenzothiophen-2-yl]carbamoyl]phenyl]methyl]-3,3-dimethyl-piperazine-1-carboxylate (480 mg, 0.599 mmol) in DCM (5 mL) is stirred at RT and 4 N HCl in dioxane (4 mL, 16 mmol) is added via syringe. Upon complete addition, the reaction is stirred at RT for 2 hours, during which time a precipitate formed. The resulting mixture is concentrated in vacuo to a light yellow solid then further dried under high vacuum at ambient temperature for 16 h to yield 464 mg of the intermediate hydrochloride salt as a light yellow solid. This solid is partitioned between saturated sodium bicarbonate and ethyl acetate. The layers are separated and the aqueous portion washed with an additional portion of ethyl acetate. The combined organic extracts are dried over sodium sulfate, decanted, then concentrated in vacuo and dried under vacuum at 55° C. for 16 h to yield the title product as a yellow-brown solid (323 mg, 0.461 mmol, 77% yield). LC-ES/MS (m/z) 701 [M+1].

Preparation 28 methyl 4-[2-[4-[[2-[[3-[(4-acetyl-2,2-dimethyl-piperazin-1-yl)methyl]benzoyl]amino]-4,5,6,7-tetrahydrobenzothiophene-3-carbonyl]amino]-2,6-difluorophenyl]ethyl]benzoate

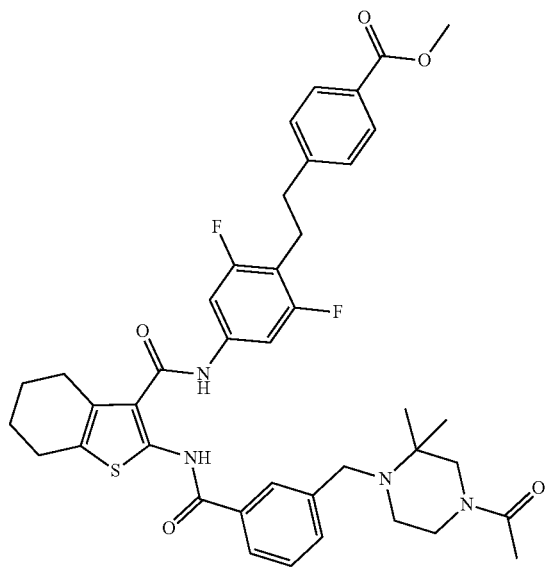 [SMILES: COC(=O)c1ccc(CCc2c(F)cc(NC(=O)c3c(NC(=O)c4cccc(CN5CCN(C(C)=O)CC5(C)C)c4)sc4c3CCCC4)cc2F)cc1]

A solution of methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate (226 mg, 0.322 mmol) in dichloromethane (10 mL) is stirred at RT and treated with acetyl chloride (46 μL, 0.645 mmol). To the resulting mixture is slowly added saturated aqueous sodium bicarbonate solution (5 mL). The mixture is stirred rapidly at r.t. for 1 h, and then diluted with saturated aqueous sodium bicarbonate solution (10 mL) and dichloromethane (15 mL). The layers are separated and the organic layer dried with magnesium sulfate. The mixture is filtered and the filter cake with dichloromethane. The resulting filtrate is dried in vacuo. The crude product is purified via normal phase flash chromatography, eluting with 3:1 ethyl acetate/hexanes under isocratic conditions, collecting fractions at 240 nM. Product containing fractions are pooled and concentrated in vacuo to afford the title product as light yellow solids (169 mg, 227 mmol, 71% yield). LC-ES/MS (m/z) 741 [M−1].

Preparation 29 methyl 4-(2,6-difluoro-4-(2-(3-(((1R,5S)-8-pentanoyl-3,8-diazabicyclo[3.2.1]octan-3-yl)methyl)benzamido)-4,5,6,7-tetrahydrobenzo[b]thiophene-3-carboxamido)phenethyl)benzoate

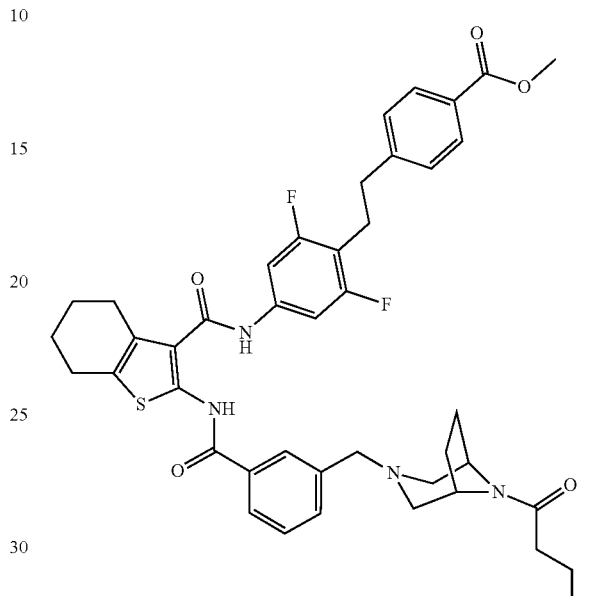

To a solution methyl 4-(4-(2-(3-(((1R,5S)-3,8-diazabicyclo[3.2.1]octan-3-yl)methyl)benzamido)-4,5,6,7-tetrahydrobenzo[b]thiophene-3-carboxamido)-2,6-difluorophenethyl)benzoate dihydrochloride (200 mg, 0.24 mmol) and TEA (0.145 mL, 4.0 eq., 1.04 mmol) in 2.60 mL of DCM, is added pentanoyl chloride dissolved in 0.5 mL DCM (87 mg, 1.5 eq., 0.39 mmol) via syringe. The resulting mixture is stirred at rt for 6 hr. The reaction mixture is concentrated in vacuo and the residue is partitioned between water (15 mL) and EtOAc (10 mL). The organic layer is separated, the aqueous layer is extracted with EtOAc (2×10 mL). The combined organic layers are washed with saturated aqueous NaCl (50 mL), dried over anhydrous $Na_2SO_4$, filtered, and concentrated to dryness under reduced pressure to afford the desired product as a light yellow solid (214 mg, 100% yield). LC-ES/MS (m/z) 783 [M+1].

Preparation 30 methyl 4-(4-(2-(3-(((1R,5S)-8-(dimethylglycyl)-3,8-diazabicyclo[3.2.1]octan-3-yl)methyl)benzamido)-4,5,6,7-tetrahydrobenzo[b]thiophene-3-carboxamido)-2,6-difluorophenethyl)benzoate

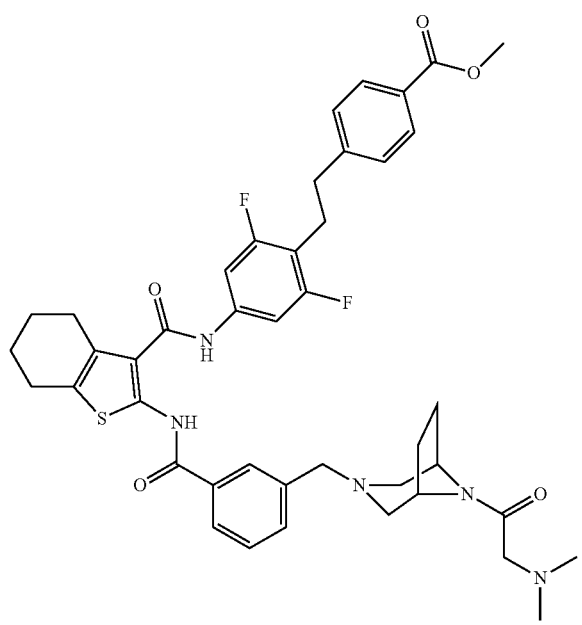 [SMILES: COC(=O)c1ccc(CCc2c(F)cc(NC(=O)c3c(NC(=O)c4cccc(CN5CC6CCC(C5)N6C(=O)CN(C)C)c4)sc4c3CCCC4)cc2F)cc1]

A solution of methyl 4-[2-[4-[[2-[[3-(3,8-diazabicyclo[3.2.1]octan-3-ylmethyl)benzoyl]amino]-4,5,6,7-tetrahydrobenzothiophene-3-carbonyl]amino]-2,6-difluoro-phenyl]ethyl]benzoate; dihydrochloride (200 mg, 0.2592 mmol), 2-(dimethylamino)acetic acid (40 mg, 0.39 mmol), triethylamine (4 equiv., 1.037 mmol), EDCI (74 mg, 1.5 equiv., 0.39 mmol) and 1-hydroxy-7-azobenzotriazole (53 mg, 1.5 equiv., 0.39 mmol) in DCM (2.6 mL) was stirred at it overnight. The reaction mixture is concentrated in vacuo and the residue is partitioned between water (15 mL) and EtOAc (10 mL). The organic layer is separated, the aqueous layer is extracted with EtOAc (2×10 mL). The combined organic layers are washed with saturated aqueous NaCl (50 mL), dried over anhydrous $Na_2SO_4$, filtered, and concentrated to dryness under reduced pressure. The residue was purified by column chromatography (0-5% MeOH/DCM) to afford the desired product as a pale yellow solid (135 mg, 66% yield). LC-ES/MS (m/z) 785 [M+1].

Preparation 31 methyl 4-[[3-[[3-[[3,5-difluoro-4-[2-(4-methoxycarbonylphenyl)ethyl]phenyl]carbamoyl]-4,5,6,7-tetrahydrobenzothiophen-2-yl]carbamoyl]phenyl]methyl]-3,3-dimethyl-piperazine-1-carboxylate

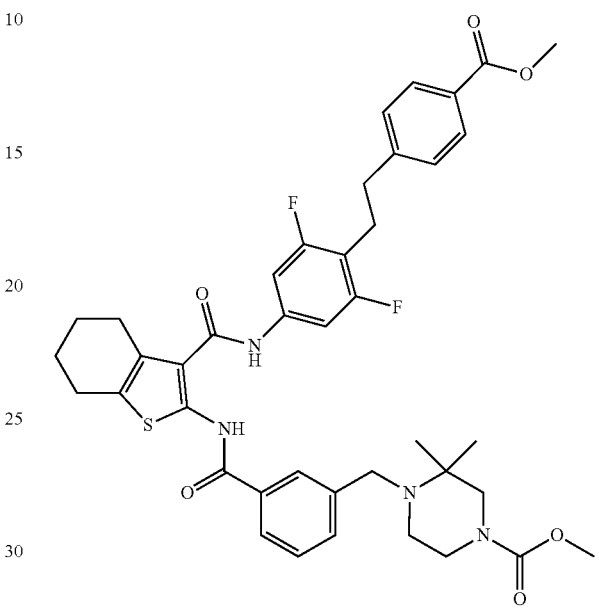

To a solution of methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl] benzoate dihydrochloride (200 mg, 0.26 mmol) and TEA (0.146 mL, 1.03 mmol) in 3 mL of DCM, methyl chloroformate (36 mg, 0.39 mmol) in 1 mL of DCM is added drop wise. The resulting mixture was stirred at room temperature overnight. The reaction mixture is diluted with a diluted with EtOAc and partitioned with water. The product was extracted with EtOAc. All organics were combined, washed with brine, dried over anhydrous $Na_2SO_4$, filtered, and concentrated under reduced pressure. The resulting residue is purified by chromatography over silica, eluting with a gradient of 0-30% of a mixture of EtOAc in hexanes, to afford the desired product as a tan foam (157 mg, 80% yield) after solvent evaporation. LC-ES/MS (m/z) 757 [M−1].

Preparation 32 methyl 4-[2-[4-[[2-[[3-[[2,2-dimethyl-4-(methylsulfamoyl)piperazin-1-yl]methyl]benzoyl]amino]-4,5,6,7-tetrahydrobenzothiophene-3-carbonyl]amino]-2,6-difluoro-phenyl]ethyl]benzoate

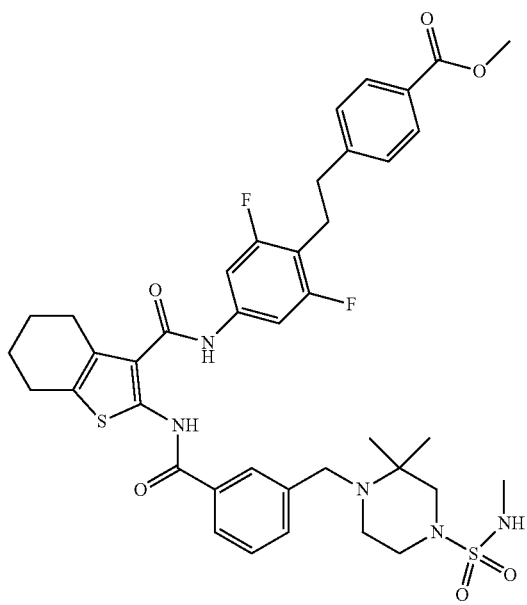 [SMILES: CNS(=O)(=O)N1CCN(Cc2cccc(C(=O)Nc3sc4c(c3C(=O)Nc3cc(F)c(CCc5ccc(C(=O)OC)cc5)c(F)c3)CCCC4)c2)C(C)(C)C1]

To a solution of methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride (201 mg, 0.26 mmol) and TEA (0.146 mL, 1.03 mmol) in 3 mL of DCM, N-methylsulfamoyl chloride (50 mg, 0.39 mmol) in 1 mL of DCM is added drop wise. The resulting mixture was stirred at room temperature overnight. The reaction mixture is diluted with a diluted with EtOAc and partitioned with water. The product was extracted with EtOAc. All organics were combined, washed with brine, dried over anhydrous $Na_2SO_4$, filtered, and concentrated under reduced pressure. The resulting residue is purified by chromatography over silica, eluting with a gradient of 0-50% of a mixture of EtOAc in hexanes, to afford the desired product as a tan foam (55 mg, 27% yield) after solvent evaporation. LC-ES/MS (m/z) 792 [M−1].

Preparation 33 methyl 4-[2-[2,6-difluoro-4-[[2-[[3-[[8-[1-(methoxymethyl)cyclopropanecarbonyl]-3,8-diazabicyclo[3.2.1]octan-3-yl]methyl]benzoyl]amino]-4,5,6,7-tetrahydrobenzothiophene-3-carbonyl]amino]phenyl]ethyl]benzoate

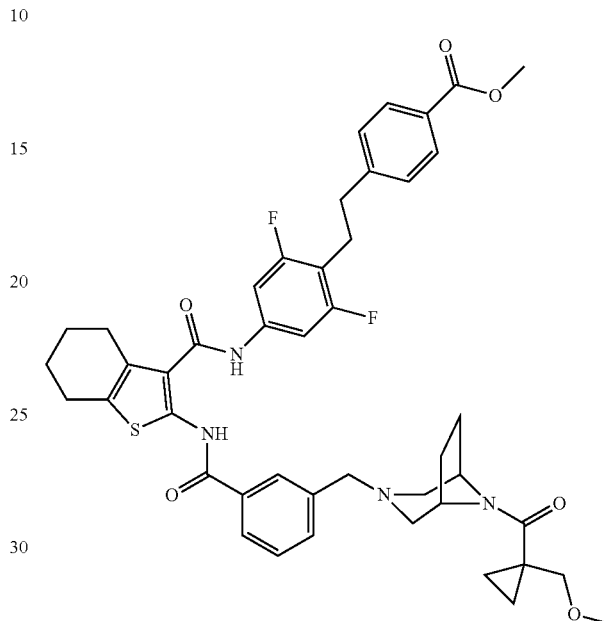

A solution of methyl 4-[2-[4-[[2-[[3-(3,8-diazabicyclo[3.2.1]octan-3-ylmethyl)benzoyl]amino]-4,5,6,7-tetrahydrobenzothiophene-3-carbonyl]amino]-2,6-difluoro-phenyl]ethyl]benzoate; dihydrochloride (150 mg, 0.194 mmol), 1-(methoxymethyl)cyclopropanecarboxylic acid (30 mg, 0.233 mmol), triethylamine (4 equiv., 0.972 mmol), EDCI (56 mg, 1.5 equiv., 0.29 mmol) and 1-hydroxy-7-azobenzotriazole (39 mg, 1.5 equiv., 0.29 mmol) in DCM (2.6 mL) was stirred at rt overnight. The reaction mixture is concentrated in vacuo and the residue is partitioned between water and EtOAc. The organic layer is separated, the aqueous layer is extracted with EtOAc. The combined organic layers are washed with saturated aqueous NaCl, dried over anhydrous $Na_2SO_4$, filtered, and concentrated to dryness under reduced pressure. The residue was purified by column chromatography (0-100% EtOAc/hexanes) to afford the desired product as a white foam (128 mg, 81% yield). LC-ES/MS (m/z) 810 [M−1].

Preparation 34 methyl 4-[2-[2,6-difluoro-4-[[2-[[3-[[8-[2-(4-methylpiperazin-1-yl)acetyl]-3,8-diazabicyclo[3.2.1]octan-3-yl]methyl]benzoyl]amino]-4,5,6,7-tetrahydrobenzothiophene-3-carbonyl]amino]phenyl]ethyl]benzoate

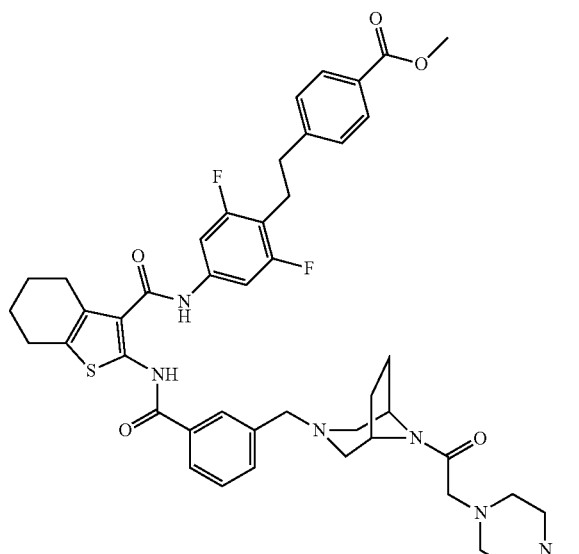

A solution of methyl 4-[2-[4-[[2-[[3-(3,8-diazabicyclo[3.2.1]octan-3-ylmethyl)benzoyl]amino]-4,5,6,7-tetrahydrobenzothiophene-3-carbonyl]amino]-2,6-difluoro-phenyl]ethyl]benzoate; dihydrochloride (200 mg, 0.26 mmol), 2-(4-methylpiperazin-1-yl)acetic acid (62 mg, 0.39 mmol), Hunig's Base (0.17 g, 1.30 mmol) and HATU (127 mg, 0.32 mmol) in DMF (2.6 mL) was stirred at rt overnight. The reaction mixture is concentrated in vacuo and the residue is partitioned between water and EtOAc. The organic layer is separated, the aqueous layer is extracted with EtOAc. The combined organic layers are washed with saturated aqueous NaCl, dried over anhydrous $Na_2SO_4$, filtered, and concentrated to dryness under reduced pressure. The residue was purified by column chromatography (0-10% MeOH/DCM) to afford the desired product as a white foam (220 mg, 100% yield). LC-ES/MS (m/z) 840 [M+1].

Preparations 35-41 below are prepared in a manner substantially similar to Preparation 29.

Preparation 35

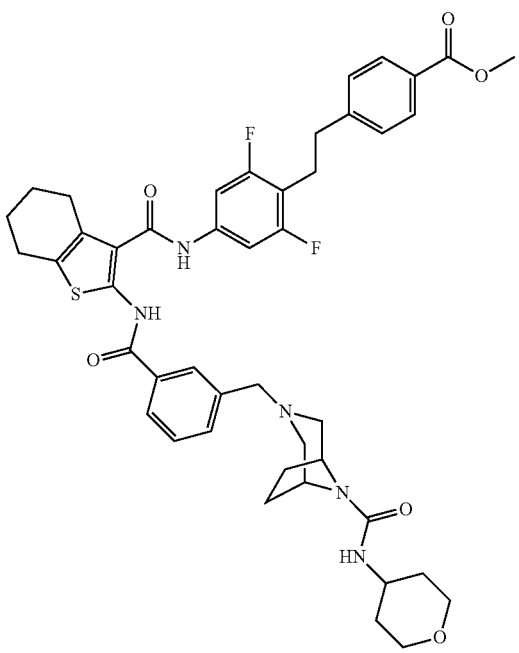 [SMILES: COC(=O)c1ccc(CCc2c(F)cc(NC(=O)c3c(NC(=O)c4cccc(CN5CC6CCC(C5)N6C(=O)NC5CCOCC5)c4)sc4c3CCCC4)cc2F)cc1]

methyl 4-[2-[2,6-difluoro-4-[[2-[[3-[[8-(tetrahydropyran-4-ylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate Prepared using 4-isocyantotetrahydropyran, 52% yield, MS (m/z) 824 [M−1]

Preparation 36

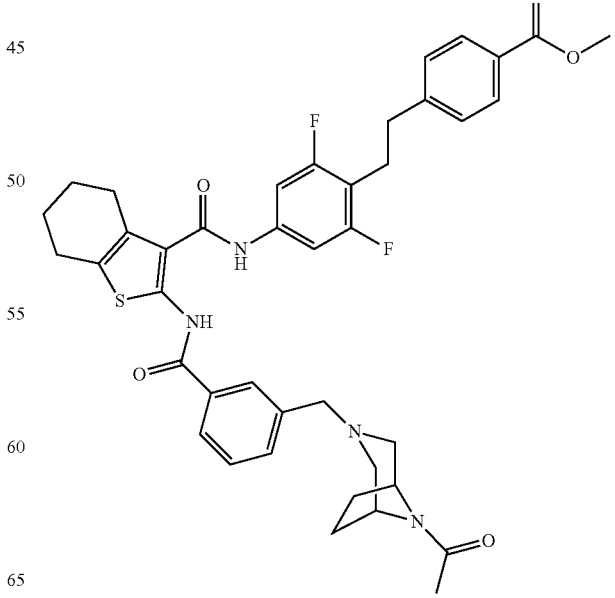

methyl 4-[2-[4-[[2-[[3-[(8-acetyl-3,8-diazabicyclo[3.2.1]octan-3-yl)methyl]benzoyl]amino]-4,5,6,7-tetrahydrobenzothiophene-3-carbonyl]amino]-2,6-difluoro-phenyl]ethyl]benzoate Prepared using acetyl chloride, 83% yield, MS (m/z) 741 [M+1]

Preparation 37

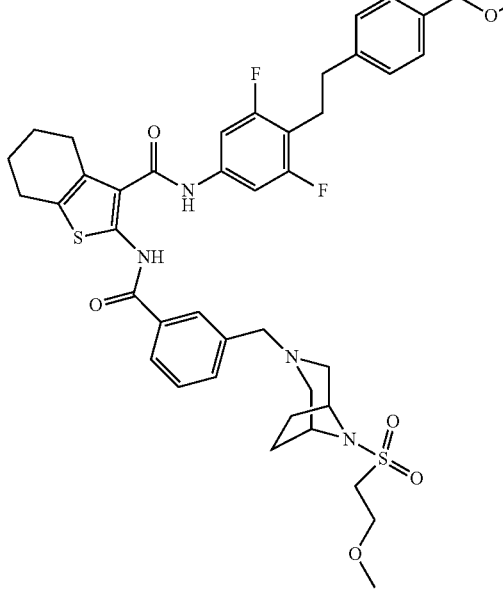

methyl 4-[2-[2,6-difluoro-4-[[2-[[3-[[8-(2-methoxy-ethylsulfonyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate Prepared using 2-methoxyethanesulfonyl chloride, 64% yield, MS (m/z) 820 [M−1]

Preparation 38

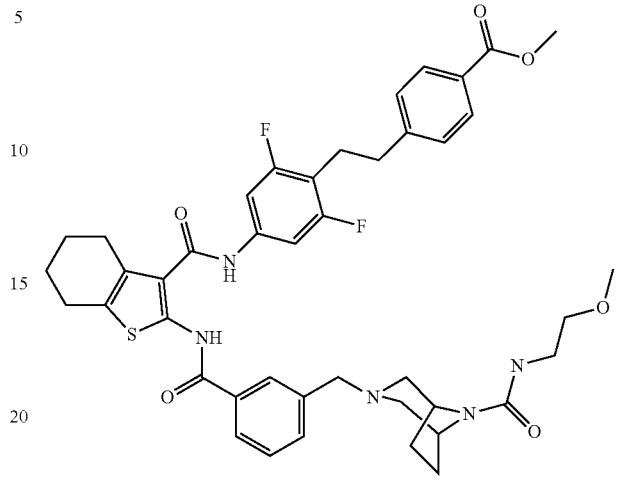

methyl 4-[2-[2,6-difluoro-4-[[2-[[3-[[8-(2-methoxy-ethylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate Prepared using 1-isocyanato-2-methoxy-ethane, 95% yield, MS (m/z) 800 [M+1]

Preparation 39

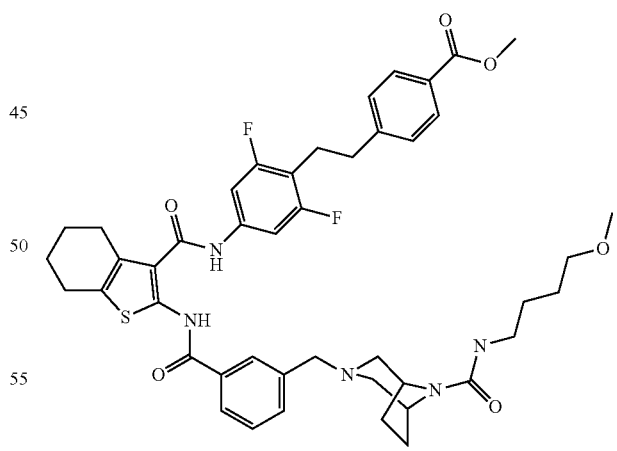

methyl 4-[2-[2,6-difluoro-4-[[2-[[3-[[8-(4-methoxy-butylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate Prepared using 1-isocyanato-4-methoxy-butane, 90% yield, MS (m/z) 827 [M−1]

Preparation 40

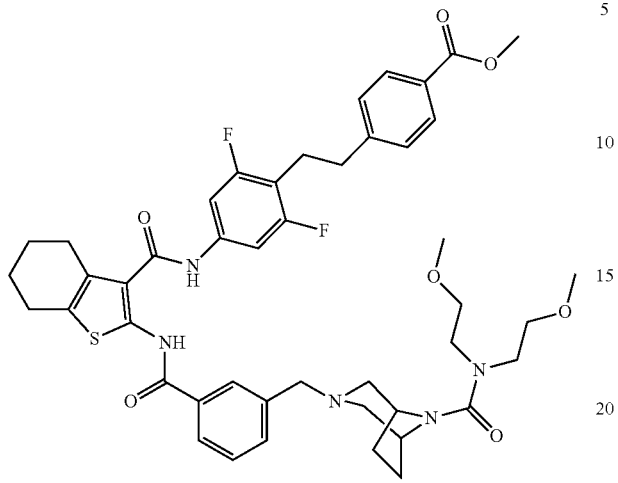

methyl 4-[2-[4-[[2-[[3-[[8-[bis(2-methoxyethyl)carbamoyl]-3,8-diazabicyclo[3.2.1]octan-3-yl]methyl]benzoyl]amino]-4,5,6,7-tetrahydrobenzothiophene-3-carbonyl]amino]-2,6-difluoro-phenyl]ethyl]benzoate Prepared using N,N-bis(2-methoxyethyl)carbamoyl chloride, 54% yield, MS (m/z) 857 [M−1]

Preparation 41

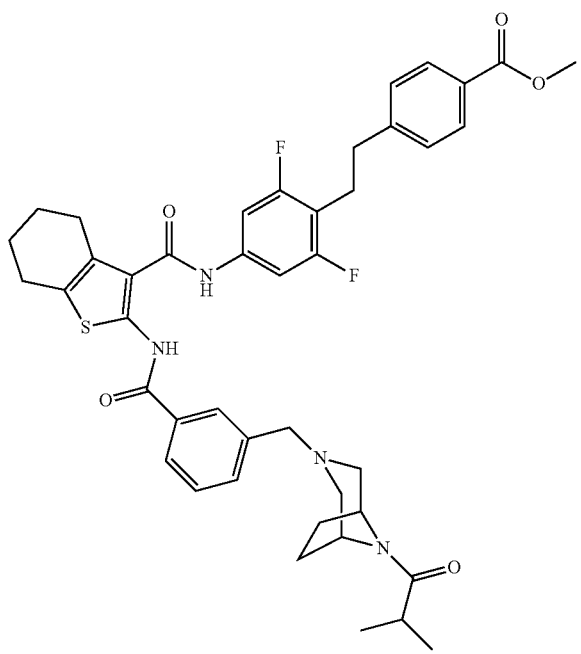 [SMILES: COC(=O)c1ccc(CCc2c(F)cc(NC(=O)c3c(NC(=O)c4cccc(CN5CC6CCC(C5)N6C(=O)C(C)C)c4)sc4c3CCCC4)cc2F)cc1]

methyl 4-[2-[2,6-difluoro-4-[[2-[[3-[[8-(2-methylpropanoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate Prepared using 2-methylpropanoyl chloride, 100% yield, MS (m/z) 767 [M−1]

Preparation 42 tert-butyl 4-[[3-[[3-[[3,5-difluoro-4-[2-(4-methoxycarbonylphenyl)ethyl]phenyl]carbamoyl]-4,5,6,7-tetrahydrobenzothiophen-2-yl]carbamoyl]phenyl]methyl]-3,3-dimethyl-piperazine-1-carboxylate

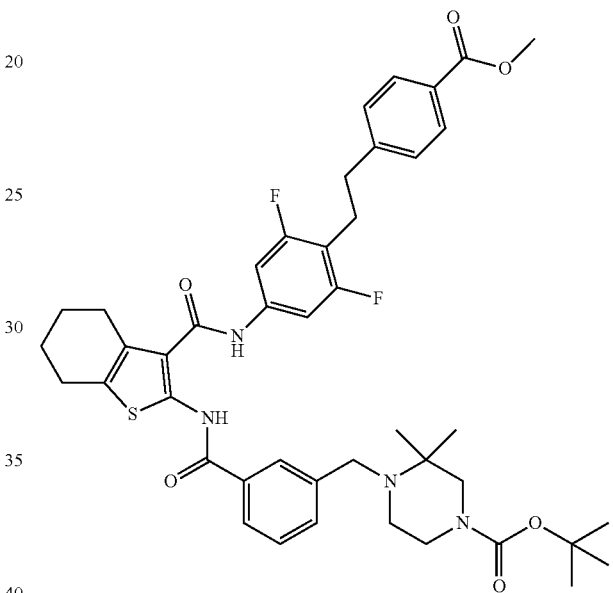

A 20 mL microwave reaction vessel is charged with methyl 4-[2-[4-[[2-[[3-(chloromethyl)benzoyl]amino]-4,5,6,7-tetrahydrobenzothiophene-3-carbonyl]amino]-2,6-difluoro-phenyl]ethyl]benzoate (1.85 g, 2.97 mmol), tert-butyl 3,3-dimethylpiperazine-1-carboxylate (0.91 g, 4.16 mmol), and DIPEA (2.07 mL, 11.9 mmol) in 15 mL of ACN. The resulting yellow suspension is heated in a BIOTAGE® Initiator microwave synthesizer at 110° C. for 4 hr. The reaction mixture is concentrated in vacuo and the residue is partitioned between 5% aqueous NaHCO$_3$ (150 mL) and DCM (50 mL). The organic layer is separated, the aqueous layer is extracted with DCM (2×25 mL). The combined organic layers are washed with saturated aqueous NaCl (50 mL), dried over anhydrous Na$_2$SO$_4$, filtered, and concentrated to dryness under reduced pressure. The resulting residue is purified by chromatography over silica, eluting with a gradient of 0-100% of a mixture of 9:1 DCM/acetone in hexane, to afford the title compound as a yellow solid (1.63 g, 69% yield) after solvent evaporation. $^1$H NMR (400.1 MHz, DMSO-d$_6$) δ 1.04 (s, 6H), 1.38 (s, 9H), 1.81-1.74 (m, 4H), 2.28 (t, J=5.0 Hz, 2H), 2.70 (br s, 4H), 2.91 (s, 4H), 3.13 (s, 2H), 3.26 (s, 2H), 3.52 (s, 2H), 3.84 (s, 3H), 7.31 (d, J=8.3 Hz, 2H), 7.44-7.39 (m, 2H), 7.55-7.46 (m, 2H), 7.75 (d, J=7.6 Hz, 1H), 7.87 (m, 3H), 9.99 (s, 1H), 11.49 (s, 1H). LC-ES/MS (m/z) 801 [M+1].

Preparation 43 methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride

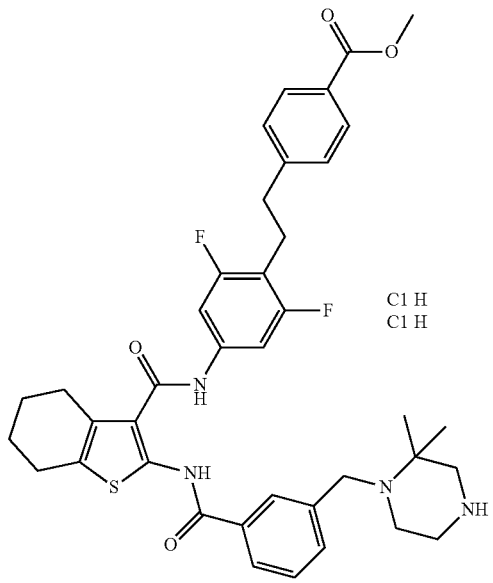 [SMILES: COC(=O)c1ccc(CCc2c(F)cc(NC(=O)c3c(NC(=O)c4cccc(CN5CCNCC5(C)C)c4)sc4c3CCCC4)cc2F)cc1]

A solution of tert-butyl 4-[[3-[[3-[[3,5-difluoro-4-[2-(4-methoxycarbonylphenyl)ethyl]phenyl]carbamoyl]-4,5,6,7-tetrahydrobenzothiophen-2-yl]carbamoyl]phenyl]methyl]-3,3-dimethyl-piperazine-1-carboxylate (1.13 g, 1.41 mmol) in DCM (14.1 mL) is stirred at RT and 4 N HCl in dioxane (3.5 mL, 14.1 mmol) is added via syringe. Upon complete addition, the reaction is stirred at RT overnight and concentrated to dryness under reduced pressure. The solid is triturated with DCM/Et₂O, the resulting precipitate is collected via vacuum filtration, and the filter cake is dried in a vacuum oven at 50° C. to afford the title compound as a white solid (0.93 g, 1.20 mmol, 85% yield). LC-ES/MS (m/z) 701 [M+1].

Preparation 44 methyl 4-[2-[4-[[2-(tert-butoxycarbonylamino)benzothiophene-3-carbonyl]amino]-2,6-difluoro-phenyl]ethyl]benzoate

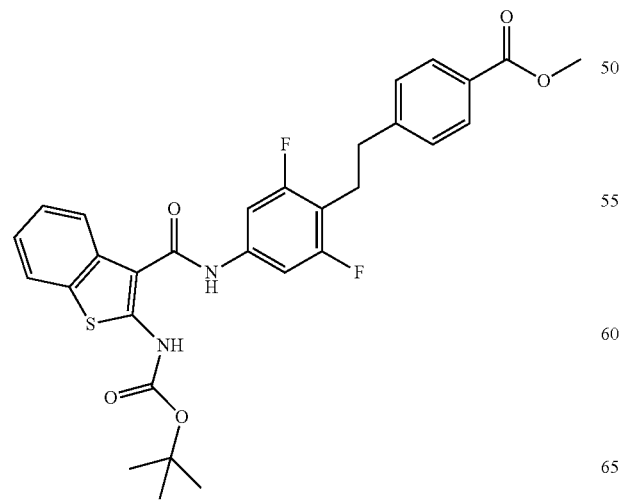

A round bottom flask is charged with 2-(tert-butoxycarbonylamino)benzothiophene-3-carboxylic acid (2.60 g, 8.87 mmol), methyl 4-[2-(4-amino-2,6-difluoro-phenyl)ethyl]benzoate (2.35 g, 8.07 mmol) and 30 mL of CH₂Cl₂. The resulting suspension is cooled in an ice/water bath, and DIPEA (5.63 mL, 32.3 mmol) is added drop wise to afford a yellow-brown turbid solution. Solid bis-(2-oxo-3-oxazolidinyl)phosphinic chloride (2.57 g, 10.1 mmol) is added in small portions over 30 min at 0° C. The reaction mixture is then warmed to RT and stirred for 48 hr. Additional solid 2-(tert-butoxycarbonylamino)benzothiophene-3-carboxylic acid (1.3 g, 4.43 mmol) is added followed by additional DIPEA (2.8 mL) and solid bis-(2-oxo-3-oxazolidinyl)phosphinic chloride (1.3 g, 5.1 mmol) in small portions over 5 min. The resulting turbid brown reaction mixture is stirred at RT for 12 hr. The reaction mixture is diluted with 40 mL of methylene chloride and then washed with 5% aqueous citric acid (150 mL), brine (2×25 mL). The organic layer is separated and dried over anhydrous Na₂SO₄, filtered, and concentrated under reduced pressure. The resulting brown foamy solid is purified by flash chromatography to yield the title compound (2.2 g, 48% yield). LC-ES/MS (m/z) 565 [M−1].

Preparation 45 methyl 4-[2-[4-[(2-aminobenzothiophene-3-carbonyl)amino]-2,6-difluoro-phenyl]ethyl]benzoate hydrochloride

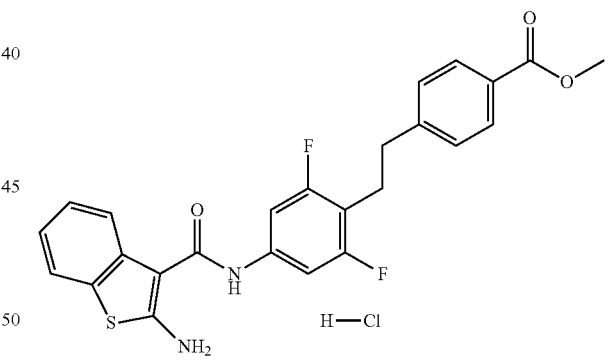

A round bottom flask is charged with methyl 4-[2-[4-[[2-(tert-butoxycarbonylamino)-benzothiophene-3-carbonyl]amino]-2,6-difluoro-phenyl]ethyl]benzoate (2.2 g, 3.9 mmol) in 30 mL of CH₂Cl₂. 4N HCl in dioxane (9.7 mL, 39 mmol) was added dropwise. The resulting mixture is allowed to stand at r.t. for 12 h. The light yellow suspension was concentrated to dryness under vacuum to yield 2.0 g (100%) of the title compound. LC-ES/MS (m/z) 467 [M+1].

Preparation 46 methyl 4-[2-[4-[[2-[[3-(chloromethyl)benzoyl]amino]benzothiophene-3-carbonyl]amino]-2,6-difluoro-phenyl]ethyl]benzoate

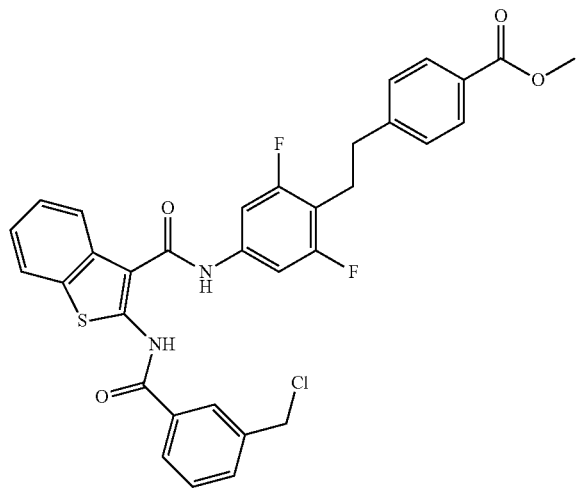 [SMILES: COC(=O)c1ccc(CCc2c(F)cc(NC(=O)c3c(NC(=O)c4cccc(CCl)c4)sc4ccccc34)cc2F)cc1]

A round bottom flask is charged with methyl 4-[2-[4-[(2-aminobenzothiophene-3-carbonyl)amino]-2,6-difluoro-phenyl]ethyl]benzoate; hydrochloride (2 g, 3.976 mmol) in 24 mL of $CH_2Cl_2$. The resulting suspension is cooled to 0° C. in an ice bath. Pyridine (0.804 mL, 9.940 mmol) was added dropwise. To the resulting yellow suspension, a solution of 3-(chloromethyl)-benzoyl chloride (0.622 mL, 4.374 mmol) in 6 mL of $CH_2Cl_2$ was added dropwise over 5 min to yield a dark yellow solution which is allowed to warm up to r.t. for 1 h. The reaction mixture is diluted with 75 mL of 10% aq $NaHCO_3$. The aqueous layer is washed with $CH_2Cl_2$ (2×25 mL). The combined organic layer is washed with brine, dried over anhydrous $Na_2SO_4$, filtered, and concentrated under reduced pressure. The crude product is triturated using 20 mL of EtOH. The resulting slurry is stirred at r.t. for 30 min and then filtered to yield 2.2 g (89%) of the title compound as light yellow solid. LC-ES/MS (m/z) 617 [M−1].

Preparation 47 methyl 4-[2-[2,6-difluoro-4-[[2-[[3-[[4-(4-hydroxy-butylcarbamoyl)-2,2-dimethyl-piperazin-1-yl]methyl]benzoyl]amino]benzothiophene-3-carbonyl]amino]phenyl]ethyl]benzoate

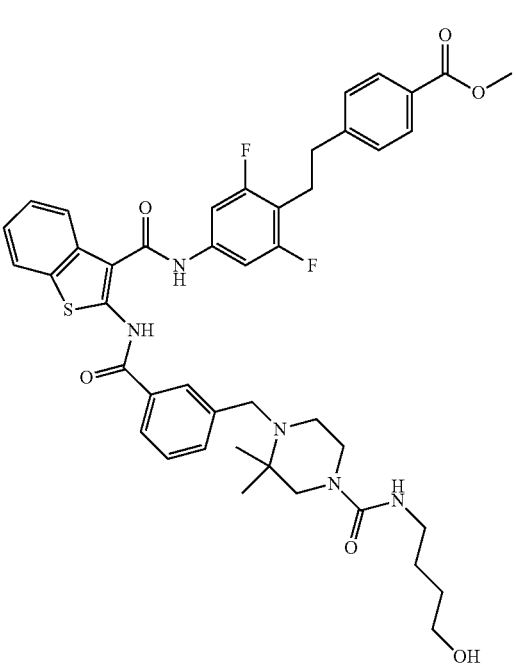 [SMILES: COC(=O)c1ccc(CCc2c(F)cc(NC(=O)c3c(NC(=O)c4cccc(CN5CCN(C(=O)NCCCCO)CC5(C)C)c4)sc4ccccc34)cc2F)cc1]

A microwave flask is charged with methyl 4-[2-[4-[[2-[[3-(chloromethyl)benzoyl]-amino]benzothiophene-3-carbonyl]amino]-2,6-difluoro-phenyl]ethyl]benzoate (0.98 g, 1.6 mmol), N-(4-hydroxybutyl)-3,3-dimethyl-piperazine-1-carboxamide; hydrochloride (0.59 g, 2.2 mmol) and a solution of DIPEA (1.1 mL, 6.3 mmol) in 12 mL of $CH_3CN$. The reaction mixture is heated to 110° C. in microwave for 4 h. The resulting yellow solution is cooled down to r.t. and concentrated to dryness under a vacuum. The residue is partitioned between 25 mL of $CH_2Cl_2$ and 75 mL of 5% aqueous $NaHCO_3$. The organic layer is washed with brine, dried over anhydrous $Na_2SO_4$, filtered, and concentrated under reduced pressure. 1.3 g (100%) of the title compound is yielded as a yellow foamy solid. LC-ES/MS (m/z) 812 [M+1].

Example 1

4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic Acid

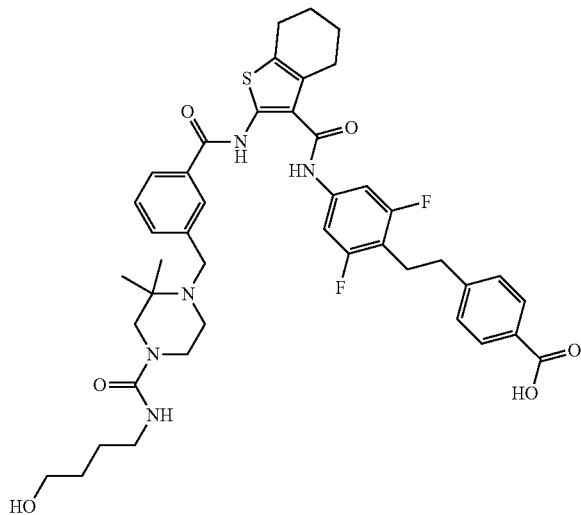 [SMILES: CC1(C)CN(C(=O)NCCCCO)CCN1Cc1cccc(C(=O)Nc2sc3c(c2C(=O)Nc2cc(F)c(CCc4ccc(C(=O)O)cc4)c(F)c2)CCCC3)c1]

A 30 mL scintillation vial is charged with methyl 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoate (196 mg, 0.24 mmol), lithium hydroxide monohydride (17.2 mg, 0.72 mmol), THF (4 mL), MeOH (2 mL) and H$_2$O (2 mL). The resulting suspension is stirred at RT for 12 hr. The reaction mixture is diluted with 4 mL of H$_2$O and concentrated under reduced pressure to approximately/z of the volume. An aqueous solution of 1 N HCl is added drop wise to provide a thick off-white suspension which is evaporated to dryness in vacuo. The resulting residue is purified by reverse phase chromatography over C-18 silica, eluting with a gradient of 0-100% of a mixture of 5% NH$_4$HCO$_3$ in H$_2$O/ACN, to afford the title compound as a pale yellow solid (82.5 mg, 41% yield) after solvent evaporation. $^1$H NMR (400.1 MHz, DMSO-d$_6$) δ 1.05 (s, 6H) 1.37-1.42 (m, 4H), 1.74-1.85 (m, 4H), 2.25-2.30 (m, 2H), 2.64-2.76 (m, 4H), 2.91 (s, 4H), 2.96-3.02 (m, 2H), 3.12-3.15 (m, 2H), 3.17-3.25 (m, 2H), 3.35-3.40 (m, 2H), 3.51 (s, 2H), 4.36 (t, J=5.1 Hz, 1H), 6.36 (t, J=5.4 Hz, 1H), 7.30 (d, J=8.3 Hz, 2H), 7.45-7.55 (m, 4H), 7.74-7.79 (m, 1H), 7.84-7.87 (m, 4H), 10.01 (s, 1H), 11.45 (s, 1H), 12.82 (br s, 1H). LC-ES/MS (m/z) 802 [M+1].

A spray-dried powder solid dispersion of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid is prepared as an amorphous product containing 30% 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium/70% PVP-VA (Polyvinylpyrrolidone-vinyl acetate). All materials are tested by ion exchange chromatography and are shown to be consistent with the intended stoichiometry. Cation exchange chromatography with evaporative light scattering detection (ELSD) is used to quantitate the levels of sodium in the active pharmaceutical ingredient (API) 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, and the solid dispersion formulation of this active pharmaceutical ingredient. Cation exchange chromatography (HPLC) is performed under conditions as follows: ELSD: 60° C., Pump: 2.0 mL/minute, Nitrogen: 1.4 L/min, Column Temp: 30° C., Column: PHENOMENEX® LUNA 5µ SCX 100A (15 cm×4.6 mm, 5 um), Injection Volume: 50 uL, Mobile Phase A: 0.1M Ammonium Formate Buffer, pH 4.5, Mobile Phase B: 100% ACN, Run time: 4 minutes.

Scale-up of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium, is performed by placing 126 mg of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, free base, in 5 mL of acetone at 60° C. while stirring at 1000 rpm, resulting in a slurry of white solid. 18 µL of sodium hydroxide (2.17 equivalents) is added. The sample turns yellow, and polarized light microscopy shows a semi-amorphous solid. The yellow solid is isolated by vacuum filtration, giving a cake of canary yellow material. 102 mg is recovered. X-ray powder diffraction (XRD) shows a poorly crystalline solid.

The solid dispersion of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium, is formulated as 30% 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium/70% PVP-VA. The scale-up of a spray dried solid dispersion containing a 30% drug load of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid is performed by placing 1040.5 mg of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, free base, and 2426.7 mg of PVP-VA in 50 mL methanol. The material is stirred resulting in a white slurry. 0.519 mL of 5N sodium hydroxide (2.0 mole equivalents) is added to the slurry and bath sonicated until a clear yellow solution is formed. The solution is slowly pumped into a spray dryer with a stream of hot nitrogen resulting in a solid powder that is collected and further dried in a vacuum oven at 50° C. under vacuum overnight to dry.

Conditions for spray drying are as follows:

| Equipment | Water Bath | Oil Bath | Nitrogen | Starting Temp. | Final Temp. |
| --- | --- | --- | --- | --- | --- |
| Setting | 60° C. | 200° C. | 60 psi | 45° C. | 50° C. |

The recovered spray dried material is observed to be microscopically non-birefringent particles of approximately 2.5 µm in diameter.

Observed levels of sodium in the active pharmaceutical ingredient, and the solid dispersion formulation of the active pharmaceutical ingredient are shown below:

| Material | Theoretical % Sodium | Observed % Sodium (n = 3) |
|---|---|---|
| Example 1, disodium salt | 5.43 | 5.59 |
| Example 1, disodium salt, solid dispersion | 1.63 | 1.73 |

Example 2

4-[2-[2,6-difluoro-4-[[2-[[3-[[4-(3-hydroxypropyl)-2,2-dimethyl-piperazin-1-yl]methyl]benzoyl]amino]-4,5,6,7-tetrahydrobenzothiophene-3-carbonyl]amino]phenyl]ethyl]benzoic Acid

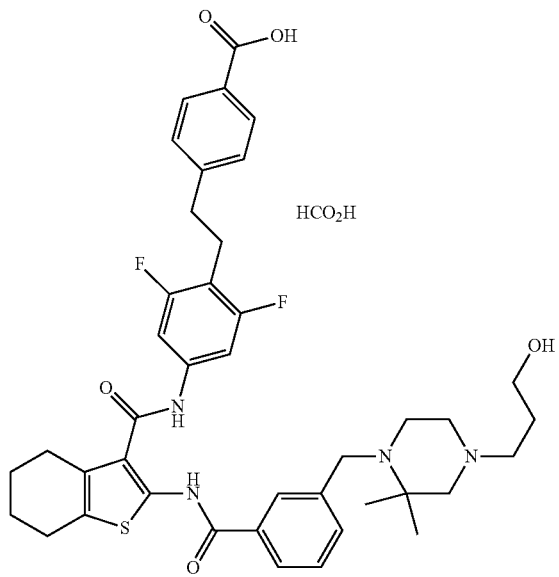 [SMILES: CC1(C)CN(CCCO)CCN1Cc1cccc(C(=O)Nc2sc3c(c2C(=O)Nc2cc(F)c(CCc4ccc(C(=O)O)cc4)c(F)c2)CCCC3)c1 ; "HCO2H"]

To a solution of methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride (214.6 mg, 0.28 mmol), DIPEA (0.097 mL, 0.55 mmol) in DCM (4 mL) in DCM (4 mL) are added 3-[(tert-butyldimethylsilyl)oxy]-1-propanal (55 mg, 0.28 mmol) and AcOH (25 µL). The resulting solution is allowed to stir at RT for 30 min. Sodium triacetoxyborohydride (0.12 g, 0.55 mmol) is added in one portion. The mixture is stirred at RT for 12 h, diluted with 10% aqueous NaHCO$_3$ (75 mL) and DCM (25 mL), and the layers are separated. The aqueous layer is extracted with DCM (2×25 mL). The organic extracts are combined, washed with saturated aqueous NaCl (25 mL), dried over anhydrous Na$_2$SO$_4$, filtered, and concentrated under reduced pressure. The resulting residue is dissolved in DCM (3 mL) and 4 M HCl in 1,4-dioxane is added. The resulting solution is stirred at RT for 24 hr. The organic solvent is removed under reduced pressure to afford a yellow solid. The material is dissolved in MeOH (2 mL) and LiOH (0.36 g, 1.4 mmol) is added. The resulting mixture is stirred at RT for 16 h, diluted with H$_2$O (4 mL), and concentrated under reduced pressure to ca. 50%° of the volume. An aqueous solution of 1 N HCl is added (5 mL), and the mixture is concentrated under reduced pressure. The resulting residue is purified by chromatography over C-18 silica, eluting with a gradient of 15-20% of a mixture of 0.1% formic acid/CH$_3$CN in 0.1% formic acid/H$_2$O for 5 minutes, then a gradient of 20-50% N of a mixture of 0.1% formic acid/CH$_3$CN in 0.1% formic acid/H$_2$O over 20 minutes, to obtain the title compound as mono-formic acid salt (73 mg, 33% yield) as a yellow solid after solvent evaporation. $^1$H NMR (400.1 MHz, DMSO-d$_6$): δ 1.10 (s, 6H), 1.55 (quintet, J=6.7 Hz, 2H), 1.85-1.69 (m, 4H), 2.41-2.09 (m, 8H), 2.81-2.61 (m, 4H), 2.91 (s, 4H), 3.65-3.36 (m, 4H), 7.29 (d, J=8.2 Hz, 2H), 7.57-7.36 (m, 4H), 7.75-7.72 (m, 1H), 7.94-7.80 (m, 3H), 8.15 (s, 1H), 11.1-9.1 (br, 3H). LC-ES/MS (m/z) 745 [M+1].

Example 3

4-[2-[4-[[2-[[3-[[4-[bis(2-methoxyethyl)sulfamoyl]-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic Acid

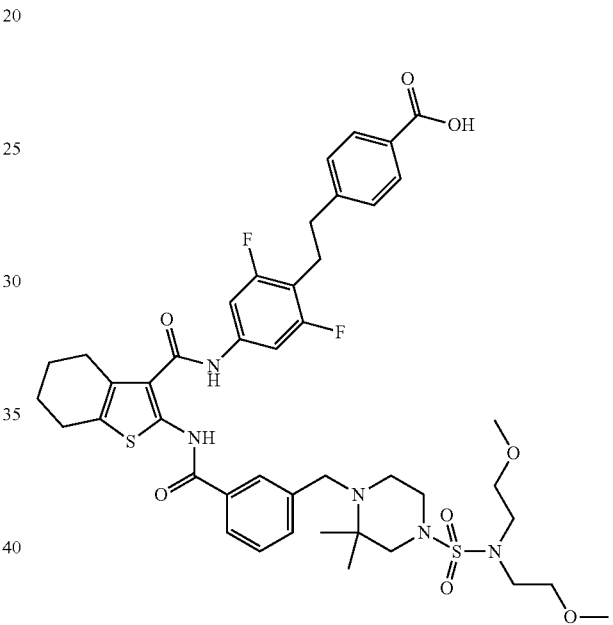

A solution of methyl 4-[2-[4-[[2-[[3-[[4-[bis(2-methoxyethyl)sulfamoyl]-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoate (148.4 mg, 0.17 mmol) and LiOH (0.016 g, 0.66 mmol) in a 2:1:1 mixture of THF:MeOH:H$_2$O (6 mL) is stirred at RT for 12 hr. The reaction mixture is diluted with H$_2$O (2 mL), concentrated under reduced pressure to ⅓ volume, and 1 N HCl (4 mL) is added. The mixture is subsequently concentrated to dryness under reduced pressure, and the resulting residue is purified by chromatography over C-18 silica, eluting with a gradient of 15-20% of a mixture of 0.1% formic acid/CH$_3$CN in 0.1% formic acid/H$_2$O for 5 minutes, then a gradient of 20-50% of a mixture of 0.1% formic acid/CH$_3$CN in 0.1% formic acid/H$_2$O over 20 minutes, to obtain the title compound as a yellow solid (99.0 mg, 67.8% yield) after solvent evaporation. $^1$H NMR (400.1 MHz, DMSO-d$_6$) δ 1.13 (s, 6H), 1.87-1.70 (m, 4H), 2.44-2.36 (m, 2H), 2.76-2.64 (m, 4H), 3.02-2.91 (m, 8H), 3.24 (s, 6H), 3.36-3.31 (m, 4H), 3.44 (t, J=5.8 Hz, 4H), 3.54-3.49 (br s, 2H), 7.30 (d, J=8.3 Hz, 2H), 7.59-7.39 (m, 4H), 7.75 (d, J=7.6 Hz, 1H), 7.90-7.81 (m, 3H), 10.01 (s, 1H), 11.47 (s, 1H), 12.83 (s, 1H). LC-ES/MS (m/z) 883 [M+1].

Example 4

4-[2-[4-[[2-[[3-[[4-(3-carboxypropyl)-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic Acid

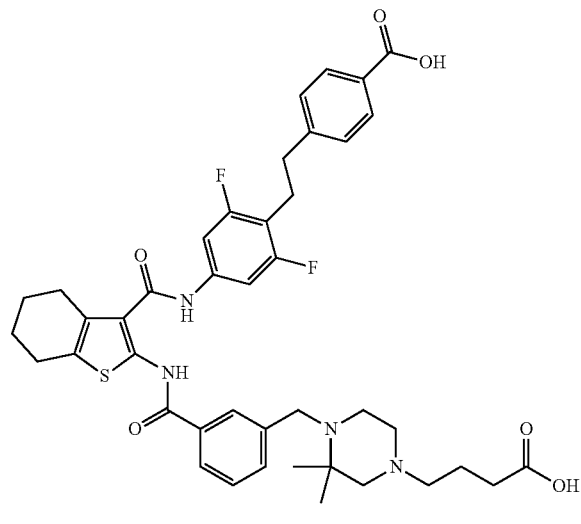 [SMILES: CC1(C)CN(CCCC(=O)O)CCN1Cc1cccc(C(=O)Nc2sc3c(c2C(=O)Nc2cc(F)c(CCc4ccc(C(=O)O)cc4)c(F)c2)CCCC3)c1]

A mixture of methyl 4-[2-[2,6-difluoro-4-[[2-[[3-[[4-(4-methoxy-4-oxo-butyl)-2,2-dimethyl-piperazin-1-yl]methyl]benzoyl]amino]-4,5,6,7-tetrahydrobenzo-thiophene-3-carbonyl]amino]phenyl]ethyl]benzoate (120.8 mg, 0.14 mmol) and LiOH (0.017 g, 0.71 mmol) in 2:1:1 mixture of THF:MeOH:H$_2$O (4 mL) is stirred at RT for 12 hr. The resulting solution is diluted with H$_2$O (2 mL) and then concentrated to ~⅓ of the volume under reduced pressure. An aqueous solution of 1 N HCl (4 mL) is added, and the solvent is removed under reduced pressure. The resulting residue is purified by chromatography over C18 silica, eluting with a gradient of 15-20% of a mixture of 0.1% formic acid/CH$_3$CN in 0.1% formic acid/H$_2$O for 5 minutes, then a gradient of 20-50% of a mixture of 0.1% formic acid/CH$_3$CN in 0.1% formic acid/H$_2$O over 20 minutes, to obtain the title compound as a yellow solid (72.5 mg, 62.3% yield) after solvent evaporation. $^1$H NMR (400.1 MHz, DMSO-d$_6$) δ 1.11 (s, 6H), 1.68-1.55 (m, 2H), 1.88-1.69 (m, 4H), 2.40-2.03 (m, 10H), 2.79-2.61 (m, 4H), 2.91 (s, 4H), 3.70-3.40 (m, 2H), 7.29 (d, J=8.3 Hz, 2H), 7.58-7.36 (m, 4H), 7.79-7.69 (m, 1H), 7.92-7.79 (m, 3H), 10.00 (br s, 1H), 11.45 (br s, 1H), 12.54 (br, 2H). LC-ES/MS (m/z) 773 [M+1].

Example 5

4-[2-[2,6-difluoro-4-[[2-[[3-[[4-(3-methoxypropyl)-2,2-dimethyl-piperazin-1-yl]methyl]benzoyl]amino]-4,5,6,7-tetrahydrobenzothiophene-3-carbonyl]amino]phenyl]ethyl]benzoic Acid, Formic Acid Salt

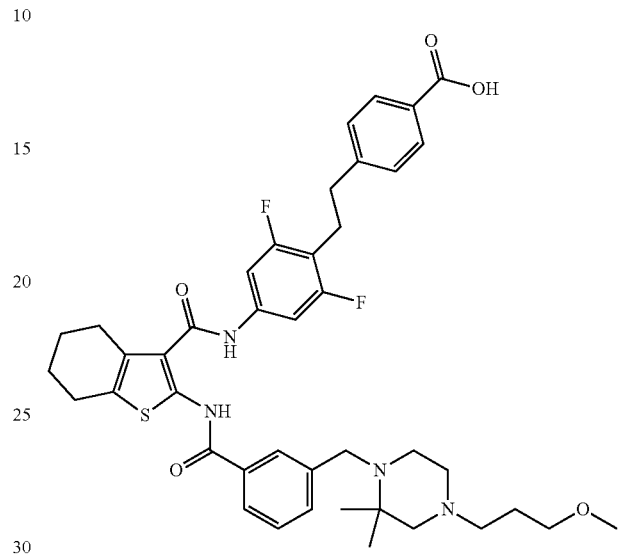

A mixture of methyl 4-[2-[2,6-difluoro-4-[[2-[[3-[[4-(3-methoxypropyl)-2,2-dimethyl-piperazin-1-yl]methyl]benzoyl]amino]-4,5,6,7-tetrahydrobenzothiophene-3-carbonyl]amino]phenyl]ethyl]benzoate (22.7 mg, 0.029 mmol) and LiOH (7 mg, 0.3 mmol) in a mixture of 2:1:1 THF:MeOH:H$_2$O (4 mL) is stirred at RT for 16 hr. The resulting mixture is diluted with H$_2$O (3 mL) and concentrated to ~½ volume under reduced pressure. An aqueous solution of 1 N HCl (5 mL) is added, and the solvent is removed under reduced pressure. The resulting residue is purified by chromatography over C-18 silica, eluting with a gradient of 15-70% over 10 minutes, to obtain the title compound as a yellow solid (16.2 mg, 68.3% yield) after solvent evaporation. $^1$H NMR (400.1 MHz, DMSO-d$_6$) δ 1.11 (s, 6H), 1.68-1.55 (m, 2H), 1.88-1.69 (m, 4H), 2.43-2.07 (m, 6H), 2.79-2.62 (m, 4H), 2.91 (s, 4H), 3.20 (s, 3H), 3.62-3.23 (m, 6H), 7.29 (d, J=8.3 Hz, 2H), 7.58-7.36 (m, 4H), 7.79-7.68 (m, 1H), 7.85 (d, J=8.2 Hz, 3H), 8.14 (s, 1H), 10.00 (br s, 1H), 11.45 (br s, 1H), 13.14-12.45 (br, 1H). LC-ES/MS (m/z) 759 [M+1].

Example 6

4-[2-[4-[[2-[[3-[[4-(2-aminoacetyl)-2,2-dimethyl-piperazin-1-yl]methyl]benzoyl]amino]-4,5,6,7-tetra-hydrobenzothiophene-3-carbonyl]amino]-2,6-difluoro-phenyl]ethyl]benzoic Acid

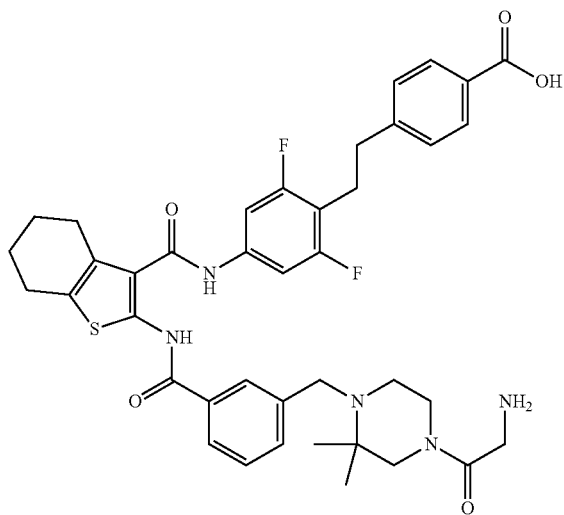 [SMILES: CC1(C)CN(C(=O)CN)CCN1Cc1cccc(C(=O)Nc2sc3c(c2C(=O)Nc2cc(F)c(CCc4ccc(C(=O)O)cc4)c(F)c2)CCCC3)c1]

To a 25 mL microwave reaction vial is charged methyl 4-[2-[4-[[2-[[3-[[4-[2-(tert-butoxycarbonylamino)acetyl]-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoate (0.451 g, 0.53 mmol), THF (12 mL), MeOH (8 mL), and 1 N LiOH in THF (2.5 mL, 2.5 mmol). The mixture is heated via microwave at 100° C. for 30 min. To this mixture is added 1 N aqueous HCl (2.5 mL), and the resulting mixture is stirred under a nitrogen stream to evaporate volatiles. The resulting oily residue is dissolved in EtOAc (25 mL), diluted with saturated aqueous NaCl (10 mL), and the layers separated. The organic layer is dried over MgSO$_4$, filtered, and the filter cake washed with solvent. The filtrate is concentrated under reduced pressure to afford the crude title compound (0.431 g) as a light yellow powder. To a round-bottomed flask is added the crude title compound (0.422 g, 0.56 mmol), DCM (25 mL), and 4 N HCl in dioxane (1.25 mL, 5 mmol). The mixture is diluted with THF (10 mL) and stirred at RT under nitrogen for 24 hr, then for 4 h at 50° C. At this point, an additional portion of 4 N HCl in dioxane (1.25 mL, 5 mmol) is added. Heating is continued for 2 hr, and the mixture is cooled to RT. The resulting slurry is diluted with hexanes (50 mL) and filtered to collect crude product (364 mg). The crude material is dissolved in MeOH/DMSO and purified by reverse phase HPLC on a Waters XBRIDGE® 30×75 mm 5 μm C-18 OBD column, eluting with a gradient of 27-50% of a mixture of 10 mM aqueous ammonium bicarbonate/ACN in MeOH at 85 mL/min over 6 min while monitoring at 205 and 237 nm. Appropriate fractions are concentrated to dryness under reduced pressure and dried for 18 hr at 40° C. to obtain the title compound (0.16 g, 43% yield). $^1$H NMR (400.13 MHz, DMSO) δ 7.93 (s, 1H), 7.88-7.79 (m, 3H), 7.46 (t, J=6.3 Hz, 1H), 7.42-7.36 (m, 3H), 7.31-7.28 (m, 2H), 4.00-3.97 (m, 30H, broad, exchangeable protons), 2.89-2.86 (m, 4H), 2.86-2.78 (m, 3H), 2.58-2.54 (m, 2H), 2.51-2.50 (m, 18H, DMSO), 2.44-2.41 (m, 3H), 1.76-1.72 (m, 4H), 1.06 (d, J=12.3 Hz, 6H). LC-ES/MS (m/z) 744 [M+1].

Example 7

4-[2-[2,6-difluoro-4-[[2-[[3-[[4-(4-methoxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic Acid

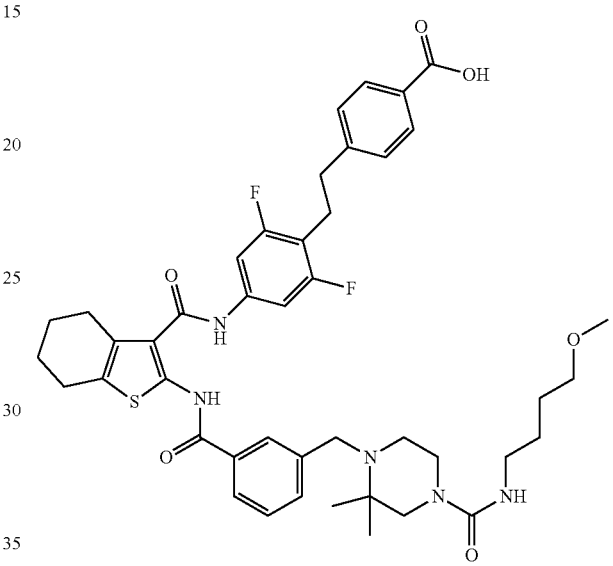

A solution of methyl 4-[2-[2,6-difluoro-4-[[2-[[3-[[4-(4-methoxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoate (93 mg, 0.11 mmol) in a 3:2:1 mixture of THF:MeOH:water (3 mL) is stirred at RT as LiOH (14 mg, 0.56 mmol) is added in one portion. The resulting reaction mixture is stirred at RT for 6 hours and concentrated in vacuo. The resulting residue is purified by reverse phase chromatography on a PHENOMENEX® GEMINI-NX® C-18 column, eluting with a gradient of 23-57% of a mixture of 5% MeOH in 10 mM aqueous ammonium bicarbonate (pH~10) and ACN over 7 min, to afford the title compound as a light yellow foamy solid (83 mg, 91%) after solvent evaporation. $^1$H NMR (400.1 MHz, DMSO-d$_6$) δ 1.03 (s, 6H), 1.38-1.43 (m, 4H), 1.72-1.76 (m, 4H), 2.22-2.28 (m, 2H), 2.60-2.67 (m, 2H), 2.67-2.75 (m, 2H), 2.88 (s, 4H), 2.95-3.02 (m, 2H), 3.095 (s, 2H), 3.18 (s, 3H); 3.15-3.22 (m, 2H), 3.23-3.28 (m, 2H), 3.49 (s, 2H), 6.34 (t, J=4.8 Hz, 1H), 7.27 (d, J=7.9 Hz, 2H), 7.35-7.42 (m, 2H), 7.40-7.48 (m, 1H), 7.47-7.52 (m, 1H), 7.72-7.77 (m, 1H), 7.81-7.88 (m, 3H), 10.01 (br s, 1H), 11.49 (br s, 1H), 12.75 (br s, 1H). LC-ES/MS (m/z) 816 [M+1].

Example 8

4-[4-[[3-[[3-[[4-[2-(4-carbamoylphenyl)ethyl]-3,5-difluoro-phenyl]carbamoyl]-4,5,6,7-tetrahydrobenzothiophen-2-yl]carbamoyl]phenyl]methyl]-3,3-dimethyl-piperazin-1-yl]-4-oxo-butanoic Acid

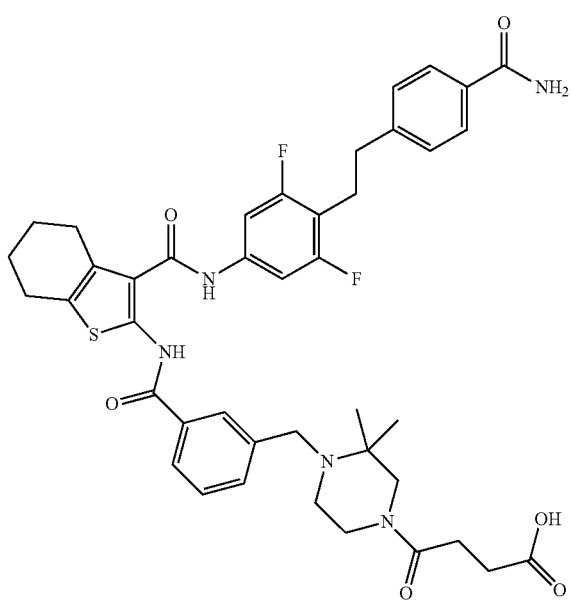 [SMILES: CC1(C)CN(C(=O)CCC(=O)O)CCN1Cc1cccc(C(=O)Nc2sc3c(c2C(=O)Nc2cc(F)c(CCc4ccc(C(N)=O)cc4)c(F)c2)CCCC3)c1]

DIPEA (0.1 mL, 0.55 mmol) is added to a solution of N-[4-[2-(4-carbamoylphenyl)ethyl]-3,5-difluoro-phenyl]-2-[[3-[(2,2-dimethylpiperazin-1-yl)methyl]benzoyl]amino]-4,5,6,7-tetrahydrobenzothiophene-3-carboxamide dihydrochloride (92.0 mg, 0.11 mmol) in DCM (4 mL) followed by succinic anhydride (160 mg, 1.65 mmol) all at once. The resulting solution is stirred at RT for 20 min, additional succinic anhydride (53.4 mg, 0.05 mmol) is added, and the resulting mixture is stirred for an additional 20 min. The reaction mixture is quenched by the addition of MeOH (0.5 mL), volatiles are removed in vacuo, and the resulting yellow oily residue is purified by reverse phase chromatography on a PHENOMENEX® GEMINI-NX® C-18 column, eluting with a gradient of 20-70% of a mixture of 5% MeOH in 10 mM aqueous ammonium bicarbonate (pH~10) and ACN over 6 min, to afford the title compound as a light yellow solid (50.9 mg, 61% yield) after solvent evaporation. $^1$H NMR (400.1 MHz, DMSO-d$_6$) δ 1.03 (s, 3H), 1.09 (s, 3H), 1.62-1.89 (m, 4H), 2.28 (m, 1H), 2.30 (m, 1H), 2.40-2.47 (m, 2H), 2.58-2.81 (br m, 4H), 2.88 (s, 4H), 3.27 (s, 2H), 3.30 (m, 2H, partial overlap with residual water peak), 3.38 (br s, 2H), 3.54 (s, 2H), 7.19-7.31 (m, 3H), 7.31-7.59 (m, 3H), 7.78 (d, J=8.1 Hz, 3H), 7.92-7.85 (m, 2H), 8.36 (br s, 1H), 8.56 (br s, 1H), 9.99 (br s, 1H), 11.51 (br s, 1H), 11.93 (br s, 1H). LC-ES/MS (m/z) 786 [M+1].

Example 9

4-[2-[2,6-difluoro-4-[[2-[[3-[(2,2,4-trimethylpiperazin-1-yl)methyl]benzoyl]amino]-4,5,6,7-tetrahydrobenzothiophene-3-carbonyl]amino]phenyl]ethyl] benzoic Acid Formic Acid Salt

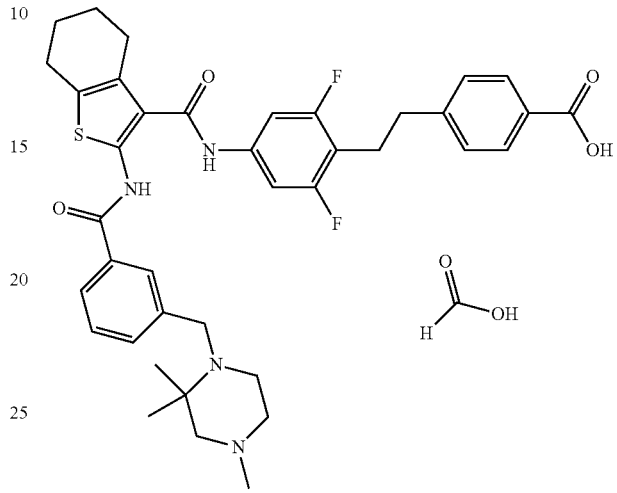

A solution of methyl 4-[2-[2,6-difluoro-4-[[2-[[3-[(2,2,4-trimethylpiperazin-1-yl)methyl]benzoyl]amino]-4,5,6,7-tetrahydrobenzothiophene-3-carbonyl]amino]phenyl]ethyl] benzoate (167 mg, 0.233 mmol) and lithium hydroxide (22 mg, 0.93 mmol) in a 2:1:1 mixture of THF:MeOH:H$_2$O (6 mL) is stirred at RT for 12 hr. The reaction mixture is diluted with water (2 mL), concentrated under reduced pressure to ~⅓ volume, and 1 N HCl (3 mL) is added. The mixture is subsequently concentrated to dryness under reduced pressure, and the resulting residue is purified by chromatography over C-18 silica, eluting with a gradient of 15-20% of a mixture of 0.1% formic acid/ACN in 0.1% formic acid/H$_2$O for 5 minutes, then a gradient of 20-50%0/of a mixture of 0.1% formic acid/ACN in 0.1% formic acid/H$_2$O over 20 minutes, to afford the title compound as a yellow solid (122 mg, 68% yield) after solvent evaporation. $^1$H NMR (400.1 MHz, DMSO-d$_6$): δ 1.11 (s, 6H), 1.89-1.67 (m, 4H), 2.15 (s, 3H), 2.41-2.30 (m, 4H), 2.70 (m, 4H), 2.91 (s, 4H), 4.10-3.10 (br, 4H), 7.29 (m, 2H), 7.57-7.36 (m, 4H), 7.75 (m, 1H), 7.90-7.81 (m, 3H), 8.15 (s, 1H), 10.8-9.7 (br, 1H), 12.9-11.1 (br, 1H). LC-ES/MS (m/z) 701 [M+1].

Example 10

4-[2-[4-[[2-[[3-[[2,2-dimethyl-4-(methylcarbamoyl)piperazin-1-yl]methyl]benzoyl]amino]-4,5,6,7-tetrahydrobenzothiophene-3-carbonyl]amino]-2,6-difluoro-phenyl]ethyl]benzoic Acid

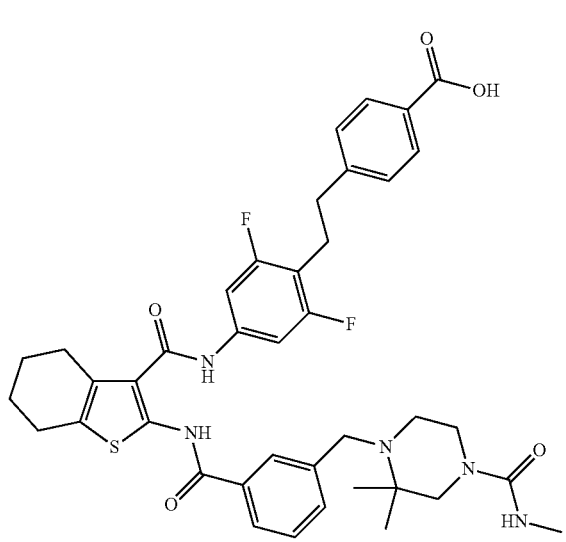 [SMILES: CNC(=O)N1CCN(Cc2cccc(C(=O)Nc3sc4c(c3C(=O)Nc3cc(F)c(CCc5ccc(C(=O)O)cc5)c(F)c3)CCCC4)c2)C(C)(C)C1]

20 mL scintillation vial is charged methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride (145 mg, 0.187 mmol) and a solution of TEA (0.13 mL, 0.94 mmol) in DCM (2 mL). The resulting suspension is stirred until it is clear. A solution of N-methylcarbamoyl chloride (21 mg, 0.22 mmol) in 1 mL of DCM is added dropwise. The resulting solution is allowed to stir at rt for 15 min. The rxn mixture is diluted with 5% aqueous NaHCO$_3$ (75 mL) and DCM (25 mL), and the layers are separated. The aqueous layer is extracted with DCM (2×25 mL). The organic extracts are combined, washed with saturated aqueous NaCl (25 mL), dried over anhydrous Na$_2$SO$_4$, filtered, and concentrated under reduced pressure. The resulting crude material and lithium hydroxide (23 mg, 0.94 mmol) are suspended in a 2:1:1 mixture of THF:MeOH:H$_2$O (4 mL) and stirred at rt for 12 hr. The reaction mixture is diluted with water (3 mL), concentrated under reduced pressure to ~⅓ volume, and 1 N HCl (4 mL) is added. The mixture is subsequently concentrated to dryness under reduced pressure, and the resulting residue is purified by chromatography over C-18 silica, eluting with a gradient of 10-15% of a mixture of 0.1% formic acid/ACN in 0.1% formic acid/H$_2$O for 5 minutes, then a gradient of 15-50% of a mixture of 0.1% formic acid/ACN in 0.1% formic acid/H$_2$O over 20 minutes, to afford the title compound as a pale yellow solid (108 mg, 77% yield) after solvent evaporation. $^1$H NMR (400.1 MHz, DMSO-d$_6$): δ 1.06 (s, 6H), 1.88-1.65 (m, 4H), 2.27 (s, 2H), 2.55 (d, J=4.3 Hz, 3H), 2.70 (m, 4H), 2.91 (s, 4H), 3.10 (s, 2H), 3.25-3.15 (m, 2H), 3.51 (s, 2H), 6.33 (m, 1H), 7.34-7.24 (m, 2H), 7.59-7.37 (m, 4H), 7.83-7.79 (m, 1H), 7.93-7.80 (m, 3H), 10.02 (br s, 1H), 11.46 (br s, 1H), 12.79 (br s, 1H). LC-ES/MS (m/z) 744 [M+1].

Example 11

4-[2-[4-[[2-[[3-[[2,2-dimethyl-4-(methylcarbamothioyl)piperazin-1-yl]methyl]benzoyl]amino]-4,5,6,7-tetrahydrobenzothiophene-3-carbonyl]amino]-2,6-difluoro-phenyl]ethyl]benzoic Acid

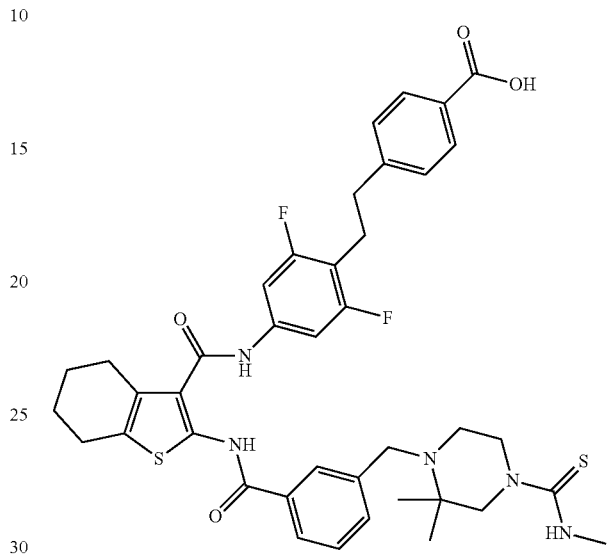

20 mL scintillation vial is charged with methyl 4-[2-[4-[[2-[[3-[(2,2-dimethylpiperazin-1-yl)methyl]benzoyl]amino]-4,5,6,7-tetrahydrobenzothiophene-3-carbonyl]amino]-2,6-difluoro-phenyl]ethyl]benzoate dihydrochloride (165 mg, 0.212 mmol) and a solution of TEA (0.15 mL, 1.1 mmol) in DCM (3 mL). The resulting suspension is stirred until it is clear. A solution of methyl isotiocyanate (18 mg, 0.24 mmol) in 1 mL of DCM is added dropwise. The resulting solution is allowed to stir at rt for 15 min. The rxn mixture is diluted with 5% aqueous NaHCO$_3$ (75 mL) and DCM (25 mL), and the layers are separated. The aqueous layer is extracted with DCM (2×25 mL). The organic extracts are combined, washed with saturated aqueous NaCl (25 mL), dried over anhydrous Na$_2$SO$_4$, filtered, and concentrated under reduced pressure. The resulting crude material and lithium hydroxide (26 mg, 1.1 mmol) are suspended in a 2:1:1 mixture of THF:MeOH:H$_2$O (4 mL) and stirred at rt for 12 hr. The reaction mixture is diluted with water (3 mL), concentrated under reduced pressure to ~⅓ volume, and 1 N HCl (4 mL) is added. The mixture is subsequently concentrated to dryness under reduced pressure, and the resulting residue is purified by chromatography over C-18 silica, eluting with a gradient of 15-20% of a mixture of 0.1% formic acid/ACN in 0.1% formic acid/H$_2$O for 5 minutes, then a gradient of 20-60% of a mixture of 0.1% formic acid/ACN in 0.1% formic acid/H$_2$O over 20 minutes, to afford the title compound as an off-white solid (73 mg, 45% yield) after solvent evaporation. $^1$H NMR (400.1 MHz, DMSO-d$_6$): δ 1.06 (s, 6H), 1.89-1.68 (m, 4H), 2.34 (m, 2H), 2.77-2.61 (m, 4H), 2.99-2.82 (m, 7H), 3.52 (s, 2H), 3.60 (s, 2H), 3.71 (br s, 2H), 7.35-7.22 (m, 2H), 7.53-7.35 (m, 3H), 7.68-7.53 (m, 2H), 7.80-7.68 (m, 1H), 7.94-7.80 (m, 3H), 10.02 (br s, 1H), 11.47 (br s, 1H), 12.79 (br s, 1H). LC-ES/MS (m/z) 760 [M+1].

Example 12

4-[2-[4-[[2-[[3-[[4-(2-carboxyethylcarbamoyl)-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic Acid

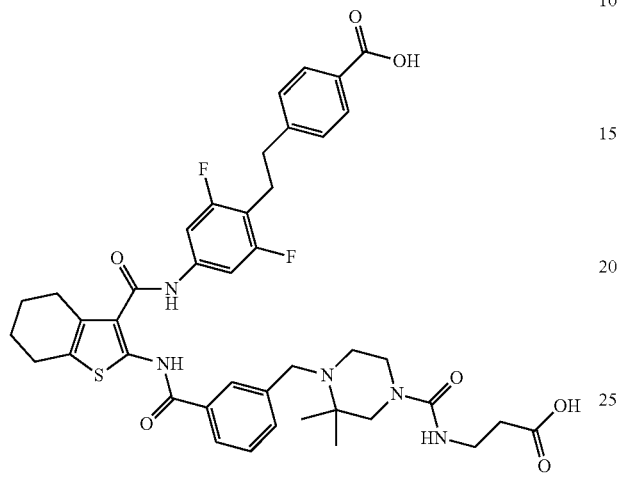

A solution of methyl 4-[2-[2,6-difluoro-4-[[2-[[3-[[4-[(3-methoxy-3-oxo-propyl)carbamoyl]-2,2-dimethyl-piperazin-1-yl]methyl]benzoyl]amino]-4,5,6,7-tetrahydrobenzothiophene-3-carbonyl]amino]phenyl]ethyl]benzoate (80 mg, 0.097 mmol) and lithium hydroxide (12 mg, 0.49 mmol) in a 2:1:1 mixture of THF:MeOH:H$_2$O (6 mL) is stirred at rt for 12 hr. The reaction mixture is diluted with H$_2$O (3 mL), concentrated under reduced pressure to ~⅓ volume, and 1 N HCl (2 mL) is added. The mixture is subsequently concentrated to dryness under reduced pressure, and the resulting residue is purified by chromatography over C-18 silica, eluting with a gradient of 10-15% of a mixture of 0.1% formic acid/ACN in 0.1% formic acid/H$_2$O for 1 minutes, then a gradient of 15-50% of a mixture of 0.1% formic acid/ACN in 0.1% formic acid/H$_2$O over 20 minutes, to obtain the title compound as an off-white solid (53 mg, 68% yield) after solvent evaporation. $^1$H NMR (400.1 MHz, DMSO-d$_6$): δ 1.05 (s, 6H), 1.88-1.66 (m, 4H), 2.31-2.20 (m, 2H), 2.42-2.31 (m, 2H), 2.79-2.60 (m, 4H), 2.91 (s, 4H), 3.11 (m, 2H), 3.27-3.15 (m, 4H), 3.51 (s, 2H), 6.48 (m, 1H), 7.35-7.23 (m, 2H), 7.60-7.36 (m, 4H), 7.80-7.68 (m, 1H), 7.94-7.80 (m, 3H), 10.02 (br s, 1H), 11.46 (br s, 1H), 12.78-12.15 (br, 1H). LC-ES/MS (m/z) 802 [M+1].

Example 13

4-[2-[2,6-difluoro-4-[[2-[[3-[[8-(methyl carbamoyl)-3,8-diazabicyclo[3.2.1]octan-3-yl]methyl]benzoyl]amino]benzothiophene-3-carbonyl]amino]phenyl]ethyl]benzoic Acid, Formic Acid Salt

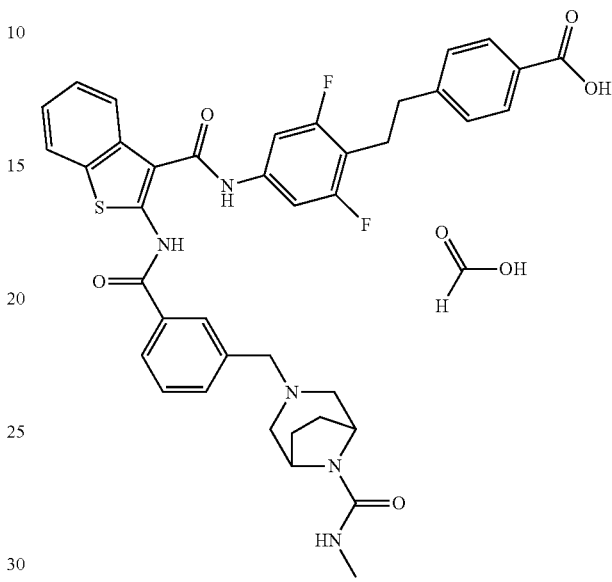

A solution of methyl 4-[2-[2,6-difluoro-4-[[2-[[3-[[8-(methylcarbamoyl)-3,8-diazabicyclo[3.2.1]octan-3-yl]methyl]benzoyl]amino]benzothiophene-3-carbonyl]amino]phenyl]ethyl]benzoate (100 mg, 0.13 mmol) and lithium hydroxide (15 mg, 0.63 mmol) in a 2:1:1 mixture of THF:MeOH:H$_2$O (4 mL) is stirred at rt for 12 hr. The reaction mixture is diluted with water (3 mL), concentrated under reduced pressure to ~⅓ volume, and 1 N HCl (3 mL) is added. The mixture is subsequently concentrated to dryness under reduced pressure, and the resulting residue is purified by chromatography over C-18 silica, eluting with 10% of a mixture of 0.1% formic acid/ACN in 0.1% formic acid/H$_2$O for 5 minutes, then a gradient of 10-65% of a mixture of 0.1% formic acid/ACN in 0.1% formic acid/H$_2$O over 15 minutes, to afford the title compound as a yellowish tan solid (67 mg, 67% yield) after solvent evaporation. $^1$H NMR (400.1 MHz, DMSO-d$_6$): δ 1.77-1.57 (m, 2H), 1.97-1.79 (m, 2H), 2.19 (d, J=10.2 Hz, 2H), 2.52 (overlaps with residual dmso resonance, 2H), 2.56 (m, 3H), 2.94 (s, 4H), 3.53 (s, 2H), 4.13 (br s, 2H), 6.37 (m, 1H), 7.65-7.25 (m, 8H), 8.08-7.78 (m, 6H), 8.14 (s, 1H), 10.63 (s, 1H), 11.93 (s, 1H), 12.79 (br s, 1H). LC-ES/MS (m/z) 738 [M+1].

Example 14

4-[2-[2,6-difluoro-4-[[2-[[3-[(4-methoxycarbonyl-2,2-dimethyl-piperazin-1-yl)methyl]benzoyl]amino]-4,5,6,7-tetrahydrobenzothiophene-3-carbonyl]amino]phenyl]ethyl]benzoic Acid

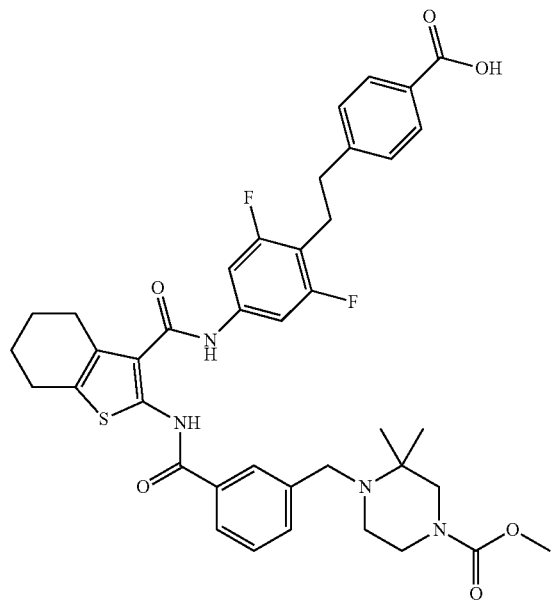 [SMILES: COC(=O)N1CCN(Cc2cccc(C(=O)Nc3sc4c(c3C(=O)Nc3cc(F)c(CCc5ccc(C(=O)O)cc5)c(F)c3)CCCC4)c2)C(C)(C)C1]

A 25 mL scintillation vial is charged with methyl 4-[[3-[[3-[[3,5-difluoro-4-[2-(4-methoxycarbonylphenyl)ethyl]phenyl]carbamoyl]-4,5,6,7-tetrahydrobenzothiophen-2-yl]carbamoyl]phenyl]methyl]-3,3-dimethyl-piperazine-1-carboxylate (152 mg, 0.20 mmol), lithium hydroxide (25 mg, 5 mmol), THF (1.5 mL), MeOH (1.0 mL) and H₂O (0.5 mL) and the resulting suspension is stirred at RT for 8 hr. The reaction mixture is evaporated, reconstituted in DMSO (2 mL) and purified on Phenomenex Kinetex EVO C18 column utilizing a gradient elution. (32-67% Acetonitrile/Aqueous 10 mM Ammonium bicarbonate pH10/5% MeOH). Eluent was concentrated under reduced pressure to give the title compound (124 mg, 83% yield) as an off-white solid. LC-ES/MS (m/z) 746 [M+1].

Example 15

4-[2-[4-[[2-[[3-[[2,2-dimethyl-4-(methylsulfamoyl)piperazin-1-yl]methyl]benzoyl]amino]-4,5,6,7-tetrahydrobenzothiophene-3-carbonyl]amino]-2,6-difluoro-phenyl]ethyl]benzoic Acid

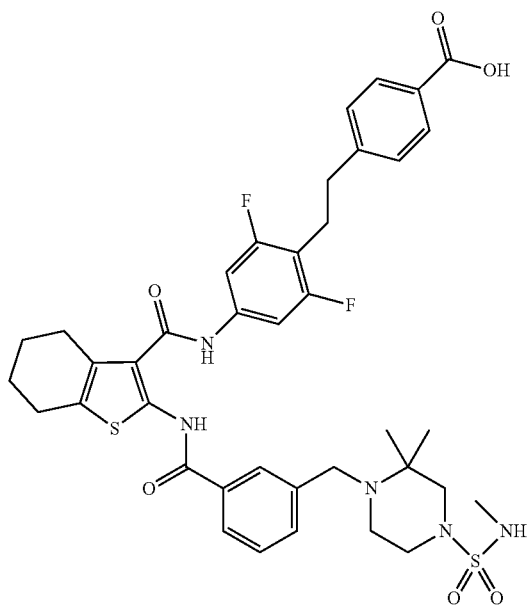 [SMILES: CNS(=O)(=O)N1CCN(Cc2cccc(C(=O)Nc3sc4c(c3C(=O)Nc3cc(F)c(CCc5ccc(C(=O)O)cc5)c(F)c3)CCCC4)c2)C(C)(C)C1]

A 25 mL scintillation vial is charged with methyl 4-[[3-[[3-[[3,5-difluoro-4-[2-(4-methoxycarbonylphenyl)ethyl]phenyl]carbamoyl]-4,5,6,7-tetrahydrobenzothiophen-2-yl]carbamoyl]phenyl]methyl]-3,3-dimethyl-piperazine-1-carboxylate (152 mg, 0.20 mmol), lithium hydroxide (25 mg, 5 mmol), THF (1.5 mL), MeOH (1.0 mL) and H₂O (0.5 mL) and the resulting suspension is stirred at RT for 8 hr. The reaction mixture is evaporated, reconstituted in DMSO (2 mL) and purified on Phenomenex Kinetex C18 column utilizing a gradient elution. (32-67% Acetonitrile/Aqueous 10 mM Ammonium bicarbonate pH10/5% MeOH). Eluent was concentrated under reduced pressure to give the title compound (124 mg, 83% yield) as an off-white solid. LC-ES/MS (m/z) 746 [M+1].

Example 16

4-(2,6-difluoro-4-(2-(3-(((R,5S)-8-pentanoyl-3,8-diazabicyclo[3.2.1]octan-3-yl)methyl)benzamido)-4,5,6,7-tetrahydrobenzo[b]thiophene-3-carboxamido)phenethyl)benzoic Acid

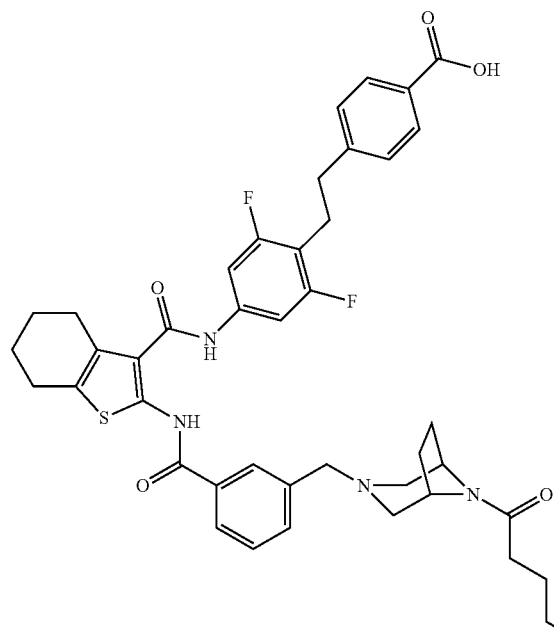

A 60 mL scintillation vial is charged with methyl 4-(2,6-difluoro-4-(2-(3-(((1R,5S)-8-pentanoyl-3,8-diazabicyclo[3.2.1]octan-3-yl)methyl)benzamido)-4,5,6,7-tetrahydrobenzo[b]thiophene-3-carboxamido)phenethyl)benzoate (214 mg, 0.27 mmol), lithium hydroxide (33 mg, 6.0 eq., 1.37 mmol), THF (1.5 mL), MeOH (1.0 mL) and H$_2$O (0.5 mL) and the resulting suspension is stirred at RT for 12 hr. The reaction mixture is diluted with H$_2$O (5 mL) and concentrated in vacuo to ~½ volume. The pH of the resulting mixture is adjusted to ~5-6 with 10% aqueous citric acid and the resulting colorless suspension is partitioned between 15 mL of water and 5 mL of 4:1 chloroform/isopropanol. The organic layer is separated, the pH of the aqueous layer is adjusted again to pH~5 with 10% aqueous citric acid, and the mixture is extracted twice with additional 4:1 chloroform/isopropanol (2×15 mL). The organic layers are combined, washed with saturated aqueous NaCl, dried over anhydrous Na$_2$SO$_4$, filtered, and the filtrate is concentrated under reduced pressure to give the title compound (114 mg, 54% yield) as an off-white solid. LC-ES/MS (m/z) 769 [M+1]. Examples 17-27 below are prepared in a manner substantially similar to Example 16.

Example 17

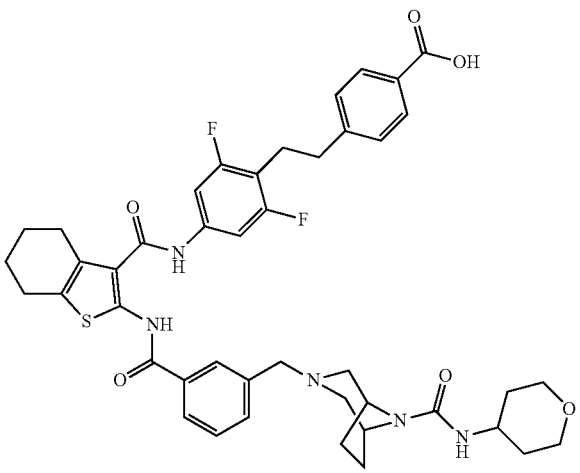 [SMILES: O=C(O)c1ccc(CCc2c(F)cc(NC(=O)c3c(NC(=O)c4cccc(CN5CC6CCC(C5)N6C(=O)NC5CCOCC5)c4)sc4c3CCCC4)cc2F)cc1]

4-[2-[2,6-difluoro-4-[[2-[[3-[[8-(tetrahydropyran-4-ylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoic Acid 17% Yield, MS m/z 812 [M+1]

Example 18

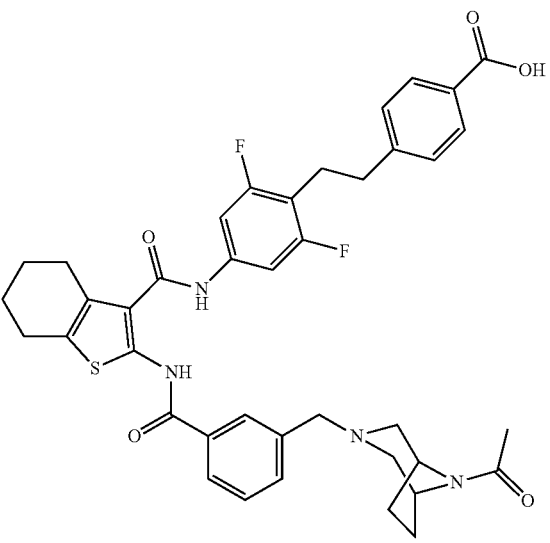 [SMILES: CC(=O)N1C2CCC1CN(Cc1cccc(C(=O)Nc3sc4c(c3C(=O)Nc3cc(F)c(CCc5ccc(C(=O)O)cc5)c(F)c3)CCCC4)c1)C2]

4-[2-[4-[[2-[[3-[(8-acetyl-3,8-diazabicyclo[3.2.1]octan-3-yl)methyl]benzoyl]amino]-4,5,6,7-tetrahydrobenzothiophene-3-carbonyl]amino]-2,6-difluorophenyl]ethyl]benzoate 85% yield, MS m/z 727 [M+1]

Example 19

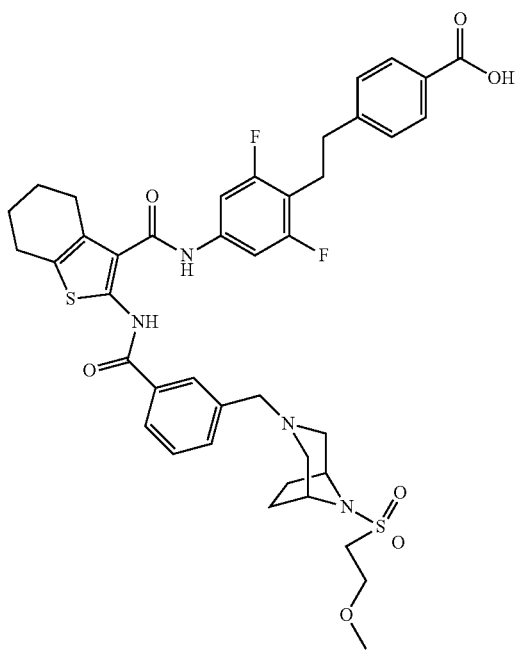

4-[2-[2,6-difluoro-4-[[2-[[3-[[8-(2-methoxyethyl-sulfonyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate 70% yield, MS m/z 807 [M+1]

Example 20

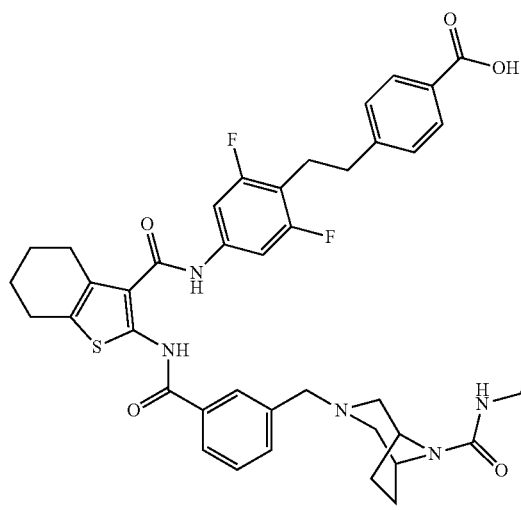 [SMILES: CC(C)C(=O)N1C2CCC1CN(Cc1cccc(C(=O)Nc3sc4c(c3C(=O)Nc3cc(F)c(CCc5ccc(C(=O)O)cc5)c(F)c3)CCCC4)c1)C2]

4-[2-[2,6-difluoro-4-[[2-[[3-[[8-(2-methoxyethylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate 28% yield, MS m/z 786 [M+1]

Example 21

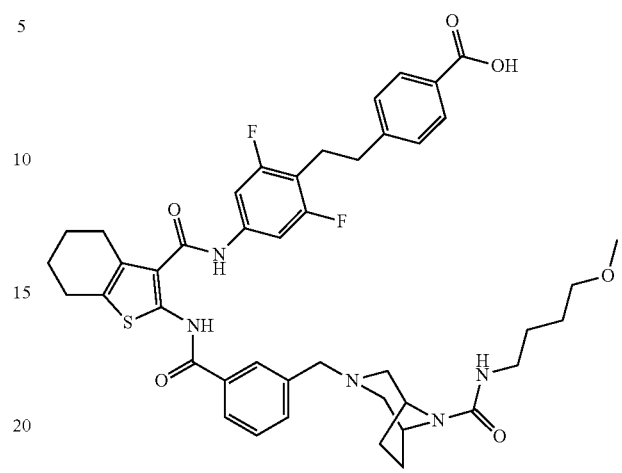

4-[2-[2,6-difluoro-4-[[2-[[3-[[8-(4-methoxybutylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate 84% yield, MS m/z 815 [M+1]

Example 22

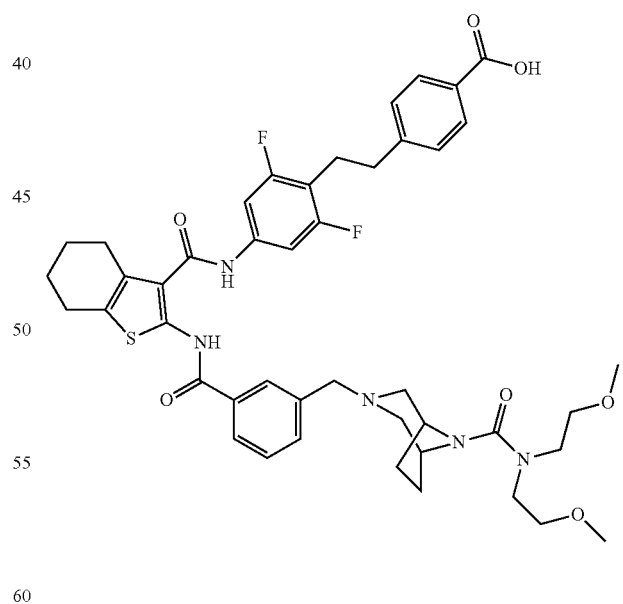

4-[2-[4-[[2-[[3-[[8-[bis(2-methoxyethyl)carbamoyl]-3,8-diazabicyclo[3.2.1]octan-3-yl]methyl]benzoyl]amino]-4,5,6,7-tetrahydrobenzothiophene-3-carbonyl]amino]-2,6-difluoro-phenyl]ethyl]benzoate 23% yield, MS m/z 844 [M+1]

Example 23

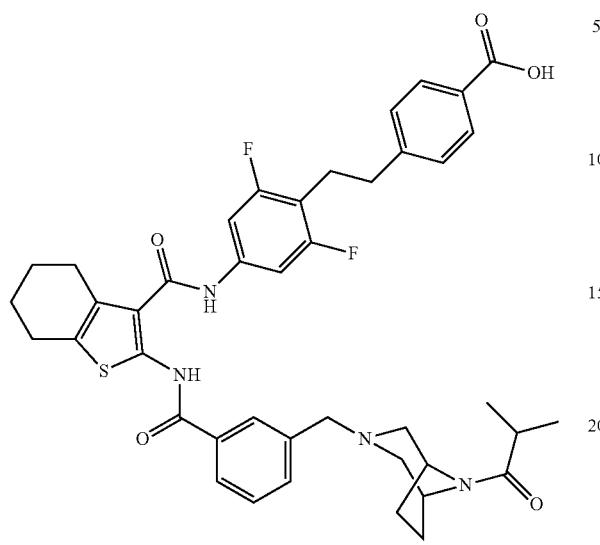

4-[2-[2,6-difluoro-4-[[2-[[3-[[8-(2-methylpropanoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate 62% yield, MS m/z 755 [M+1]

Example 24

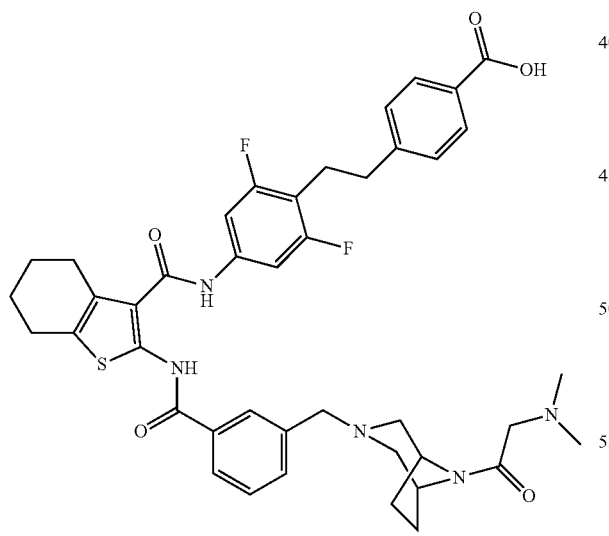

4-[2-[4-[[2-[[3-[[8-[2-(dimethylamino)acetyl]-3,8-diazabicyclo[3.2.1]octan-3-yl]methyl]benzoyl]amino]-4,5,6,7-tetrahydrobenzothiophene-3-carbonyl]amino]-2,6-difluoro-phenyl]ethyl]benzoic acid 73% yield, MS m/z 770 [M+1]

Example 25

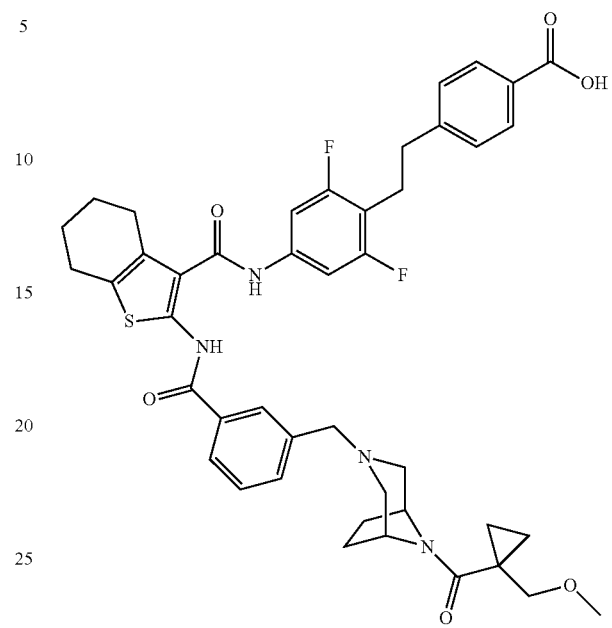

4-[2-[2,6-difluoro-4-[[2-[[3-[[8-[1-(methoxymethyl)cyclopropanecarbonyl]-3,8-diazabicyclo[3.2.1]octan-3-yl]methyl]benzoyl]amino]-4,5,6,7-tetrahydrobenzothiophene-3-carbonyl]amino]phenyl]ethyl]benzoic Acid 98% yield MS m/z 797 [M+1]

Example 26

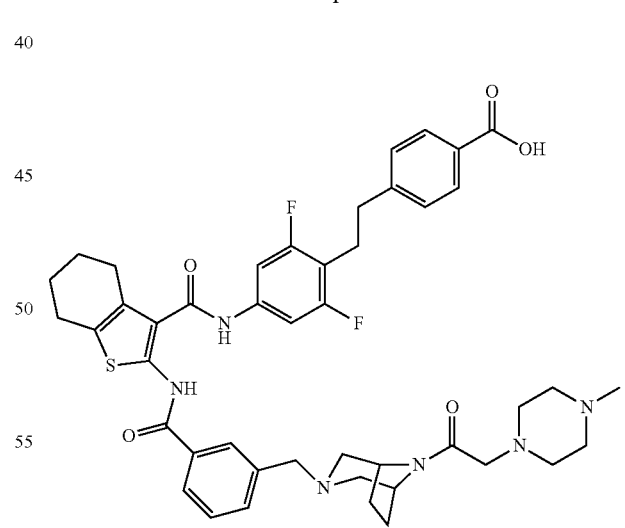

4-[2-[2,6-difluoro-4-[[2-[[3-[[8-[2-(4-methylpiperazin-1-yl)acetyl]-3,8-diazabicyclo[3.2.1]octan-3-yl]methyl]benzoyl]amino]-4,5,6,7-tetrahydrobenzothiophene-3-carbonyl]amino]phenyl]ethyl]benzoic Acid 59% yield, MS m/z 825 [M+1]

Example 27

4-[2-[4-[[2-[[3-[(4-acetyl-2,2-di methyl-piperazin-1-yl)methyl]benzoyl]amino]-4,5,6,7-tetrahydrobenzo-thiophene-3-carbonyl]amino]-2,6-difluoro-phenyl]ethyl]benzoic acid

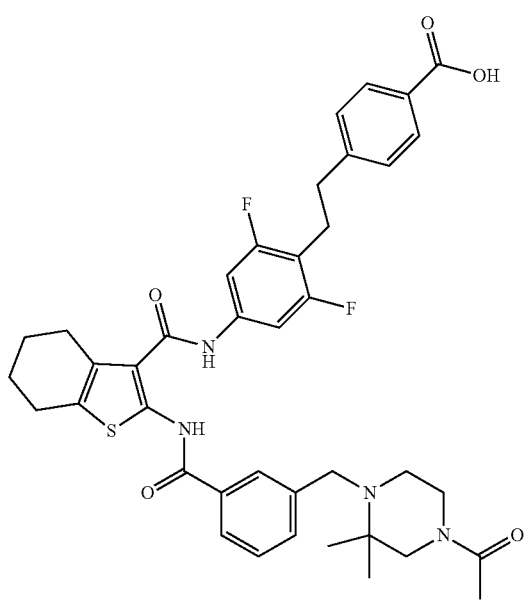 [SMILES: CC(=O)N1CCN(Cc2cccc(C(=O)Nc3sc4c(c3C(=O)Nc3cc(F)c(CCc5ccc(C(=O)O)cc5)c(F)c3)CCCC4)c2)C(C)(C)C1]

To a 25 mL microwave reaction vial is charged methyl methyl 4-[2-[4-[[2-[[3-[(4-acetyl-2,2-dimethyl-piperazin-1-yl)methyl]benzoyl]amino]-4,5,6,7-tetrahydrobenzothi-ophene-3-carbonyl]amino]-2,6-difluoro-phenyl]ethyl]benzoate (169 mg, 0.227 mmol), tetrahydrofuran (12 mL, 148 mmol), methanol (8 mL, 197 mmol), and 1M aqueous lithium hydroxide solution (1.14 mL, 1.14 mmol). The vial is capped and the resulting mixture is stirred and heated via microwave irradiation at 100° C. for 30 minutes. The reaction mixture is then carefully treated with 1M aqueous hydrochloric acid solution (1.14 mL, 1.14 mmol), resulting in a reaction mixture pH of ~4. The resulting mixture is concentrated to dryness in vacuo and the product is purified via low pH, reversed phase chromatography. 1H NMR (400.1 MHz, DMSO-$d_6$) δ 1.04 (s, 3H), 1.09 (s, 3H), 1.84-1.72 (m, 4H), 1.97 (bs, 3H), 2.29-2.27 (m, 1H), 2.37-2.33 (m, 1H), 2.75-2.65 (m, 4H), 2.91 (s, 4H), 3.25-3.3.24 (m, 2H), 3.38-3.34 (m, 2H), 3.54 (s, 2H), 7.29 (d. J=7.6 Hz, 2H), 7.45-7.37 (m, 2H), 7.51-7.46 (m, 1H), 7.55 (d, J=7.5 Hz, 1H), 7.76 (d, J=7.5 Hz, 1H), 7.85 (d, J=8.0 Hz, 2H), 7.91 (s, 1H), 9.99 (s, 1H), 11.49 (s, 1H), 12.84 (s, 1H). LC-ES/MS (m/z) 729 [M+1].

Example 28

4-[2-[2,6-difluoro-4-[[2-[[3-[[4-(4-hydroxybutylcar-bamoyl)-2,2-dimethyl-piperazin-1-yl]methyl]ben-zoyl]amino]benzothiophene-3-carbonyl]amino]phe-nyl]ethyl]benzoic Acid

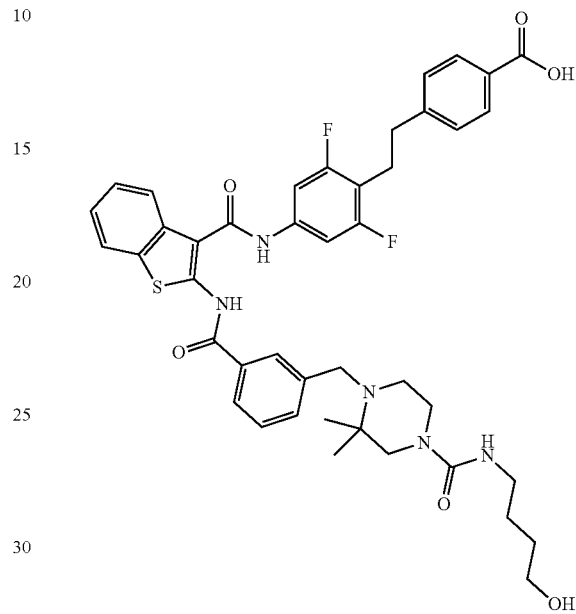

To a solution of methyl 4-[2-[2,6-difluoro-4-[[2-[[3-[[4-(4-hydroxybutylcarbamoyl)-2,2-dimethyl-piperazin-1-yl]methyl]benzoyl]amino]benzothiophene-3-carbonyl]amino]phenyl]-ethyl]benzoate (0.20 g, 0.25 mmol) in 8 mL of a mixed solvent (THF/CH$_3$OH/H$_2$O in 2:1:1 ratio), LiOH (18 mg, 0.75 mmol) is added. The resulting mixture is allowed to stand at r.t. for 12 h. Additional LiOH (18 mg, 0.75 mmol) is added. And the mixture is allowed to stand at r.t. for 48 h and diluted with 1 mL of 4N HCl in dioxane. The solvent is removed under a vacuum. The crude product is purified by flash chromatography to yield 120 mg (57%) of the title compound as a white solid. $^1$H NMR (399.80 MHz, DMSO-$d_6$): δ 1.06 (s, 6H), 1.31-1.48 (m, 4H), 2.34 (s, 2H), 2.87-2.97 (m, 4H), 3.07-3.09 (m, 2H), 3.09-3.18 (s, 2H), 3.18-3.28 (m, 2H), 3.38 (partially overlaps with res water peak, 1H), 3.54 (s, 2H), 4.38 (m, 2H), 6.33 (m, 2H), 7.25-7.71 (m, 8H), 7.73-8.08 (m, 6H), 10.64 (s, 1H), 11.99 (s, 1H), 12.8 (br s, 1H). LC-ES/MS (m/z) 798 [M+1].

Inhibition of NaPi-IIb In Vitro

Inhibition of $^{33}$P uptake is measured in human and mouse NaPi-IIb T-REX™-CHO stable cell lines. cDNA for NaPi-IIb is subcloned in plasmid SLC34A2 pcDNA5/TO (human) and SLC34A2 pcDNA5/TO (mouse) and stable cell lines are generated from clonal isolation for both human and mouse respectively. Mouse and human stable lines are maintained in continuous culture in growth media (Dulbecco's Modified Eagle Medium: Nutrient Mixture F-12 (3:1), 10% Heat Inactivated FBS, 1% penicillin/streptomycin/FUNGI-EZONE® (HYCLONE™), 20 mM HEPES, 250 μg/mL hygromycin, 5 μg/mL blasticidin). Cells are harvested from T225 cell culture flasks (CORNING®) using 0.25%

Trypsin, and plated in 96 well CYTOSTAR-T™ scintillating microplates (Amersham Systems) at 40,000 cells/well in 100 µL of growth media plus 100 ng/mL of tetracycline. Cell plates are incubated overnight at 37° C. and 5% C02. The next day, compounds are serially diluted using one to three dilutions in 100% DMSO. Cell plates may remain in the incubator until ready to be assayed. A cell plate is removed from the incubator and media removed. Cells are washed 3 times with 200 µL assay buffer (137 mM NaCl, 5.4 mM KCl, 2.8 mM CaCl$_2$), 1.2 mM MgSO$_4$, and 14 mM Tris-HCl buffer, pH~7.5), removing buffer in between washes. Serially diluted compounds in DMSO are further diluted 50 fold in assay buffer and 50 µL added to the CYTOSTAR-T™ assay plate, immediately followed by the addition of 50 µL of $^{33}$P solution (PERKIN-ELMER®, Walton, Mass.; 0.05 µCi/50 µL). CYTOSTAR-T™ assay plates are covered with foil to protect from light and incubated for 60 min at RT. After the 60 min incubation, 100 µL of a stop solution (assay buffer+400 µM Phloretin) is added to the assay plate to stop $^{33}$P uptake. The plate is immediately read on a Wallac MICROBETA® Trilux liquid scintillation counter and luminometer after stop solution is added with 1 minute count per well. Each plate may be processed separately and staggered in time so there may be no delay in counting after stop solution is added. Percent inhibition at all concentrations tested (final assay concentrations 100-0.005 µM) are calculated relative to 1% DMSO (minimum effect), and the effect of 100 µM of a fully efficacious NaPi-IIb inhibitor (maximum effect). IC$_{50}$ values were calculated using a 4 parameter logistic curve fitting equation. The numbers presented are the geometric means with standard deviation (SD) calculated where n is the number of runs. Thus. Table 1 describes the relative IC$_{50}$ values for Examples 1-28 against human NaPi-IIb and murine NaPi-IIb, respectively.

TABLE 1

Relative IC$_{50}$ (rel IC$_{50}$) values for Examples 1-28 against human and murine NaPi-IIb in vitro data in T-REX ™ Chinese Hamster Ovarian-stable cell lines.

| Example | h NaPi-IIb rel IC50 (nM), (SD) | n | m NaPi-IIb rel IC50 (nM), (SD) | n |
|---|---|---|---|---|
| 1 | 32.4, (23.0) | 3 | 43.9, (24.2) | 3 |
| 2 | 13.6, (18.2) | 4 | 17.5, (9.05) | 3 |
| 3 | 51.1, (32.3) | 2 | 40.9 | 1 |
| 4 | 18.6, (9.8) | 3 | 26.0, (37.3) | 3 |
| 5 | 76.3, (4.2) | 2 | 23.6, (8.2) | 2 |
| 6 | 8.7, (6.7) | 6 | 9.9, (4.2) | 3 |
| 7 | 16.2, (2.6) | 2 | 8.56 | 1 |
| 8 | 32.6, (19.5) | 3 | 35, (7.8) | 2 |
| 9 | 197, (162) | 5 | 314, (526) | 5 |
| 10 | 3.4, (4.1) | 5 | 5.9, (5.0) | 5 |
| 11 | 10.8, (5.6) | 4 | 12.6, (2.2) | 4 |
| 12 | 156, (73.6) | 3 | 217, (122) | 3 |
| 13 | 4.3, (9.4) | 2 | 9.0 | 1 |
| 14 | 5.3, (2.5) | 3 | 11.3, (0.8) | 4 |
| 15 | 6.5, (4.4) | 4 | 16.8, (8.5) | 4 |
| 16 | 60.0, (50.1) | 3 | 31.2, (6.7) | 3 |
| 17 | 3.5, (4.6) | 3 | 8.8, (4.3) | 3 |
| 18 | 5.1, (9.2) | 3 | 20.3, (37.4) | 3 |
| 19 | 60.3, (36.3) | 2 | 20.0, (31.6) | 3 |
| 20 | 9.5, (23.1) | 3 | 9.1, (15.5) | 3 |
| 21 | 19.6, (8.7) | 2 | 5.3, (11.7) | 2 |
| 22 | 9.4, (14.4) | 3 | 27.3, (16.6) | 2 |
| 23 | 46.5, (47.8) | 3 | 47.1, (6.5) | 3 |
| 24 | 16.6, (12.7) | 3 | 30.2, (9.6) | 3 |

TABLE 1-continued

Relative IC$_{50}$ (rel IC$_{50}$) values for Examples 1-28 against human and murine NaPi-IIb in vitro data in T-REX ™ Chinese Hamster Ovarian-stable cell lines.

| Example | h NaPi-IIb rel IC50 (nM), (SD) | n | m NaPi-IIb rel IC50 (nM), (SD) | n |
|---|---|---|---|---|
| 25 | 22.5, (3.2) | 2 | 8.3, (11.0) | 3 |
| 26 | 2.4 | 1 | 15.3 | 1 |
| 27 | 25.9, (1.9) | 3 | 22.6, (6.4) | 3 |
| 28 | 6.2, (1.2) | 3 | 7.6, (1.6) | 3 |

Inhibition of NaPi-IIb In Vivo

For test article and vehicle control preparation, add vehicle, 20% hydroxypropyl-beta-cyclodextrin (HPBCD) in water, to the test article. Sonicate to reduce particle size in an ultrasonic water bath as needed. If necessary, use a polytron to break down any visible particles in test article solution. Add 1 N NaOH as indicated in Table 2 below. The pH of the vehicle control is adjusted to 8.0 to 8.5 with 1N NaOH.

TABLE 2

Amount of 1N NaOH to add to indicated testing compound.

| Example No. | 1N NaOH per mg of compound (µL) |
|---|---|
| 1 | 2.5 |
| 2 | 3.8 |
| 3 | 2.3 |
| 4 | 3.9 |
| 5 | 3.7 |
| 6 | 2.7 |
| 7 | 2.5 |
| 8 | 2.5 |

Radioactive phosphate preparation: Prepare a 16.25 mM Na$_2$HPO$_4$ solution using 0.9% saline as the vehicle. Mix until a clear solution is formed. Adjust pH to approximately 7.4. Filter using a sterile 0.2 µm polyethersulfone membrane. For the final preparation of the radioactive phosphate dosing solution, add 0.5 µl of stock H$_3$$^3$PO$_4$ per 1 mL of Na$_2$HPO$_4$. Mix thoroughly then sterile filter the H$_3$$^{33}$PO4+Na$_2$HPO$_4$ solution using a 0.2 µm polyethersulfone membrane prior to dosing. Measure the radioactivity of each sample with the scintillation counter. If the DPMs are between 100,000 and 150,000 proceed with dosing.

In-vivo protocol: Male C57B16 male mice at the age of about 8-9 wks old are fasted for 16 hrs the day before the study. They are assigned to treatment groups based on body weight on the day of study. Mice are dosed orally with either the test article, prepared as described above, or vehicle control at a 10 mls/kg dose volume. Fifteen minutes later, the radioactive phosphate dosing solution is given by oral gavage. Fifteen minutes later, blood is collected by orbital bleed. Plasma is prepared and 50 µl of EDTA plasma from each mouse is mixed with 10 ml of scintillation fluid and the counts determined by scintillation counting. The effect of the test article is determined by comparing the counts in the plasma from the test article treated animals to counts in the plasma of the vehicle control treated animals [Percent Inhibition=(counts in the plasma of test article treated animals/counts in the plasma of vehicle treated animals)×100%].

Percent inhibition is measured at 30 minutes post administration of the compound or vehicle, and at 15 minutes post administration of the labelled phosphate. Percent Inhibition for indicated Examples are illustrated in Table 3 below.

TABLE 3

In vivo data for Example compounds 4, 6, and 8

| Example | Treatment | n | Percent Inhibition | SEM |
|---------|-----------|---|--------------------|-----|
| 4 | 5 mg/kg | 6 | 52 | 5.4 |
| 6 | 5 mg/kg | 6 | 62 | 2.5 |
| 8 | 5 mg/kg | 6 | 60 | 5.2 |

Alternative vehicles, for example poly-1-vinylpyrrolidone-co-vinyl acetate (PVP-VA), at varying concentrations, may be used. Example 1 can be assayed in PVP-VA, and for this study the compound is formulated as described in the solid dispersion preparation of Example 1, followed by dissolving in water then dosing by oral gavage. The vehicle control is water with varying concentrations of PVP-VA, matching the concentration found in the highest dose of Example 1, the lowest dose of Example 1, and an intermediate dose of Example 1. No effect of varying PVP-VA on the uptake of radiolabeled phosphate is observed over several studies, and thus all the vehicles are averaged to calculate percent inhibition.

TABLE 4

In vivo data for Example 1 in PVP-VA formulation

| Group | Treatment | n | Percent Inhibition | SEM |
|-------|-----------|---|--------------------|-----|
| 1 | Vehicle | 23 | 0 | 5.12 |
| 2 | 30 mg/kg Example 1 | 7 | 75.83 | 3.54 |
| 3 | 10 mg/kg Example 1 | 7 | 75.64 | 4.02 |
| 4 | 3 mg/kg Example 1 | 7 | 68.71 | 4.30 |
| 5 | 1 mg/kg Example 1 | 7 | 66.90 | 3.10 |
| 6 | 0.3 mg/kg Example 1 | 7 | 51.21 | 7.71 |
| 7 | 0.1 mg/kg Example 1 | 7 | 30.61 | 7.57 |
| 8 | 0.03 mg/kg Example 1 | 7 | 0.75 | 14.45 |

The effect of a test compound on gastric emptying can be assessed by dosing the compound and radiolabeled phosphate in a manner similar to that used to assess a compound's ability to inhibit NaPi-IIb in vivo. After bleeding the mice, they were sacrificed and their stomachs harvested. The harvested stomachs are digested in 10 ml of 1N NaOH overnight, and the recovered radiolabeled phosphate DPMs determined by scintillation counting. The compound mediated effect on the rate of gastric emptying is determined by comparing the dpms in the stomach of animals treated with compound, to that of animals treated with vehicle.

Compounds of the invention, for instance Example 1, show advantageous pharmacological properties, such as potency, in vivo distribution, in vivo efficacy, and favorable lack of toxicity in preclinical testing. For instance Example 1 shows surprisingly advantageous margin of NaPi-IIb inhibition with respect to inhibition of in vivo gastric emptying. In addition, Example 1 is generally well tolerated when administered in vivo to normal rats for a period of four days, and shows an advantageous lack of toxicity in this in vivo experiment.

We claim:
1. A compound of the formula:

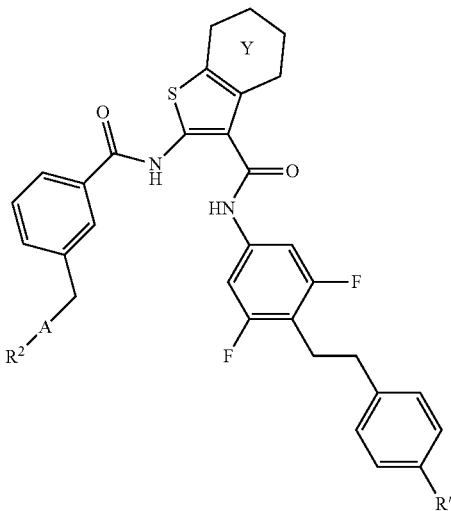

Formula II wherein Y is a fused cyclohexane ring or a fused phenyl ring, wherein A is

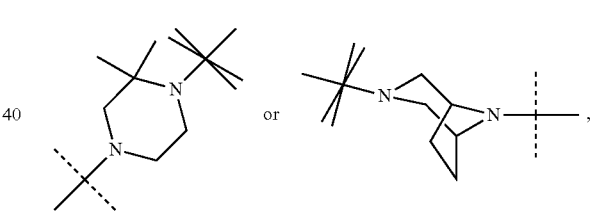

wherein the crossed lines indicate bonds for the point of attachment to the core of Formula II, and the dashed lines indicate bonds for the point of attachment to $R^2$, wherein $R^2$ is selected from the group consisting of
—$CH_3$, —$(CH_2)_3OH$, —$(CH_2)_2OCH_3$, —$(CH_2)_3CO_2H$, —$COOCH_3$, —$COCH_3$, —$CO(CH_2)_3CH_3$, —$COCH(CH_3)_2$, —$CO(CH_2)_2CO_2H$, —$COCH_2NH_2$, —$COCH_2N(CH_3)_2$, —$SO_2N[(CH_2)_2OCH_3]_2$, —$SO_2NHCH_3$, —$SO_2(CH_2)_2OCH_3$, —$CONH(CH_2)_4OH$, —$CONH(CH_2)_4OCH_3$, —$CONHCH_3$, —$CONH(CH_2)_2CO_2H$, —$CONH(CH_2)_2OCH_3$, —$CON(CH_2CH_2OCH_3)_2$, —$CSNHCH_3$,

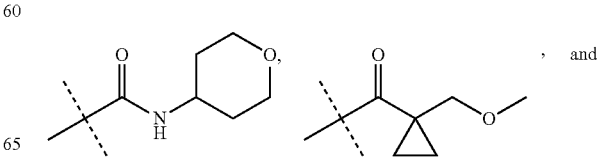

, and

-continued

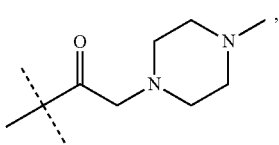

wherein the dashed lines represent the point of attachment,
wherein R' is —CO$_2$H or —CONH$_2$,
or a pharmaceutically acceptable salt thereof.

2. The compound of C claim 1, wherein Y is a fused cyclohexane ring, A is

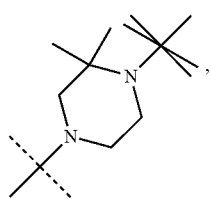

and R' is —CO$_2$H, or a pharmaceutically acceptable salt thereof.

3. The compound of claim 1, wherein Y is a fused cyclohexane ring, A is

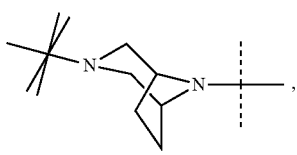

and R' is —CO$_2$H, or a pharmaceutically acceptable salt thereof.

4. The compound of claim 1 which is of the formula:

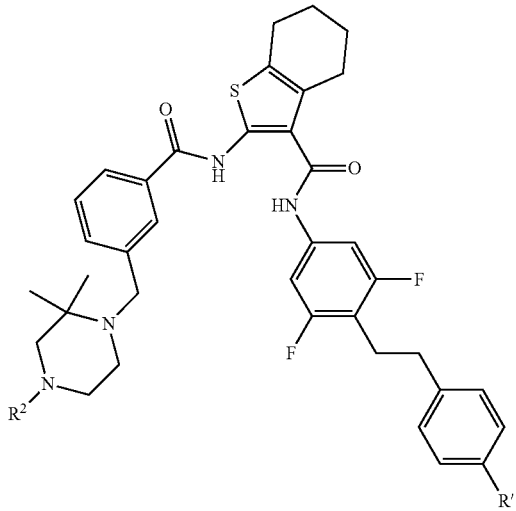

wherein R$^2$ is selected from the group consisting of —(CH$_2$)$_3$OH, —(CH$_2$)$_3$OCH$_3$, —(CH$_2$)$_3$CO$_2$H, —CONH(CH$_2$)$_4$OH, —COCH$_2$NH$_2$, —SO$_2$N[(CH$_2$)$_2$OCH$_3$]$_2$, —CONH(CH$_2$)$_4$OCH$_3$, and —CO(CH$_2$)$_2$CO$_2$H, wherein R' is —CO$_2$H or —CONH$_2$, or a pharmaceutically acceptable salt thereof.

5. The compound of claim 4 wherein R' is —CO$_2$H, or a pharmaceutically acceptable salt thereof.

6. The compound of claim 1 which is 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, which can be structurally represented as:

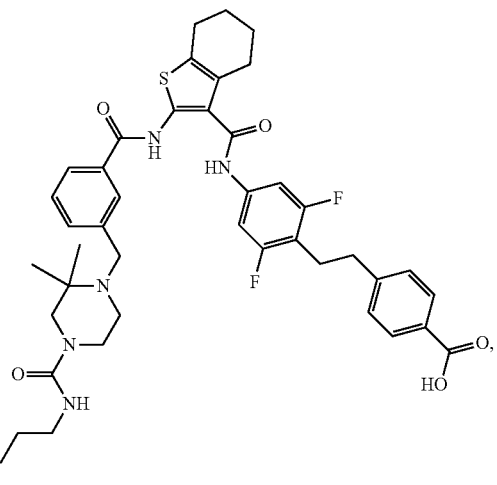

or a pharmaceutically acceptable salt thereof.

7. The compound claim 1 which is 4-[2-[2,6-difluoro-4-[[2-[[3-[[4-(3-hydroxypropyl)-2,2-dimethyl-piperazin-1-yl]methyl]benzoyl]amino]-4,5,6,7-tetrahydrobenzothiophene-3-carbonyl]amino]phenyl]ethyl]benzoic acid, which can be structurally represented as:

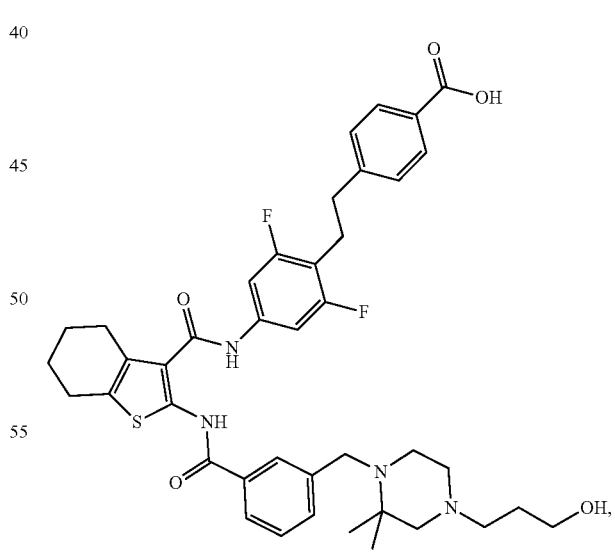

or a pharmaceutically acceptable salt thereof.

8. The compound claim 1 which is 4-[2-[4-[[2-[[3-[[4-[bis(2-methoxyethyl)sulfamoyl]-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic acid, which can be structurally represented as:

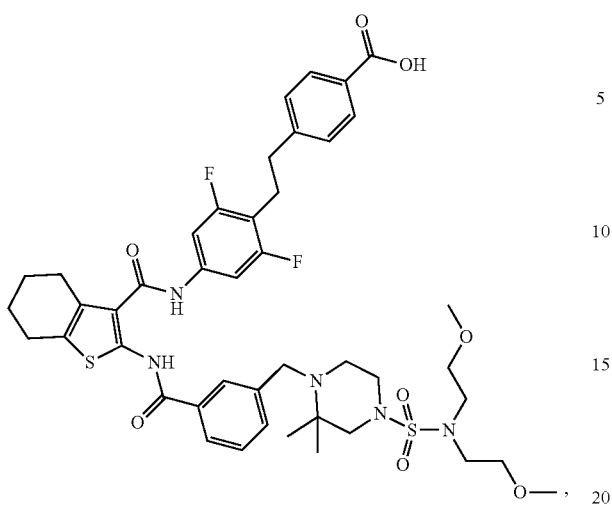

or a pharmaceutically acceptable salt thereof.

9. The compound claim 1 which is 4-[2-[4-[[2-[[3-[[4-(3-carboxypropyl)-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic acid, which can be structurally represented as:

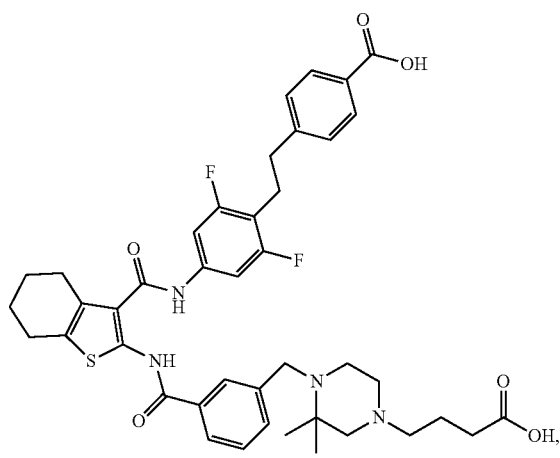 [SMILES: CC1(C)CN(CCCC(=O)O)CCN1Cc1cccc(C(=O)Nc2sc3c(c2C(=O)Nc2cc(F)c(CCc4ccc(C(=O)O)cc4)c(F)c2)CCCC3)c1]

or a pharmaceutically acceptable salt thereof.

10. The compound claim 1 which is 4-[2-[2,6-difluoro-4-[[2-[[3-[[4-(3-methoxypropyl)-2,2-dimethyl-piperazin-1-yl]methyl]benzoyl]amino]-4,5,6,7-tetrahydrobenzothiophene-3-carbonyl]amino]phenyl]ethyl]benzoic acid, which can be structurally represented as:

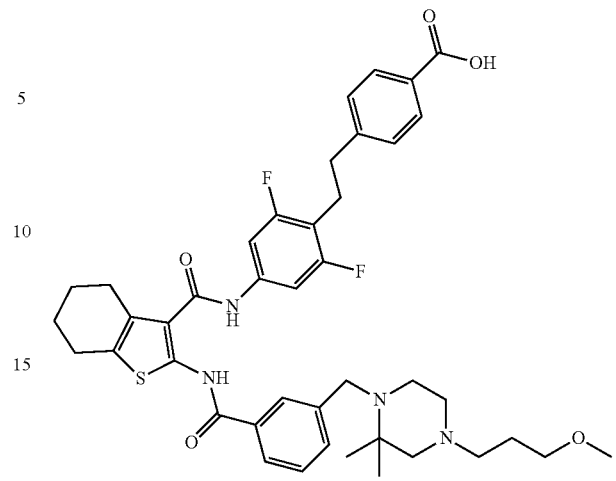

or a pharmaceutically acceptable salt thereof.

11. The compound G claim 1 which is 4-[2-[4-[[2-[[3-[[4-(2-aminoacetyl)-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic acid, which can be structurally represented as:

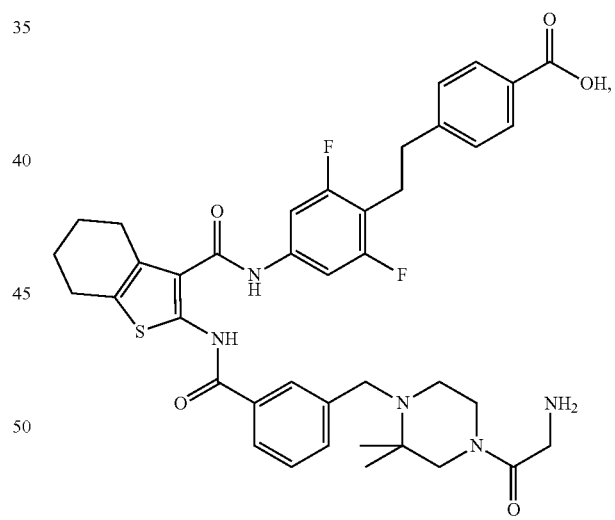

or a pharmaceutically acceptable salt thereof.

12. The compound claim 1 which is 4-[2-[2,6-difluoro-4-[[2-[[3-[[4-(4-methoxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, which can be structurally represented as:

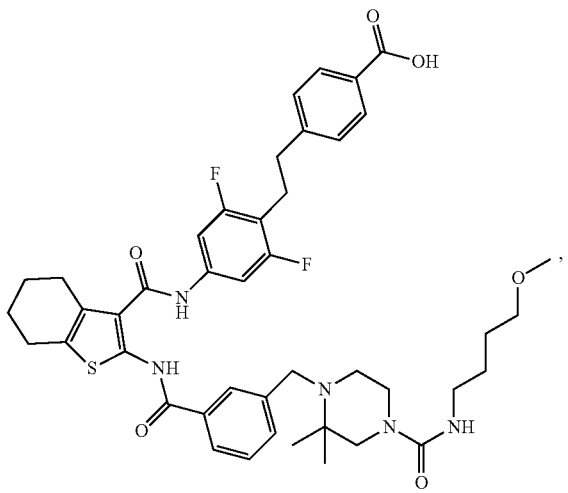 [SMILES: COCCCCNC(=O)N1CCN(Cc2cccc(C(=O)Nc3sc4c(c3C(=O)Nc3cc(F)c(CCc5ccc(C(=O)O)cc5)c(F)c3)CCCC4)c2)C(C)(C)C1]

or a pharmaceutically acceptable salt thereof.

13. The compound claim 1 which is 4-[4-[[3-[[3-[[4-[2-(4-carbamoylphenyl)ethyl]-3,5-difluoro-phenyl]carbamoyl]-4,5,6,7-tetrahydrobenzothiophen-2-yl]carbamoyl]phenyl]methyl]-3,3-dimethyl-piperazin-1-yl]-4-oxo-butanoic acid, which can be structurally represented as:

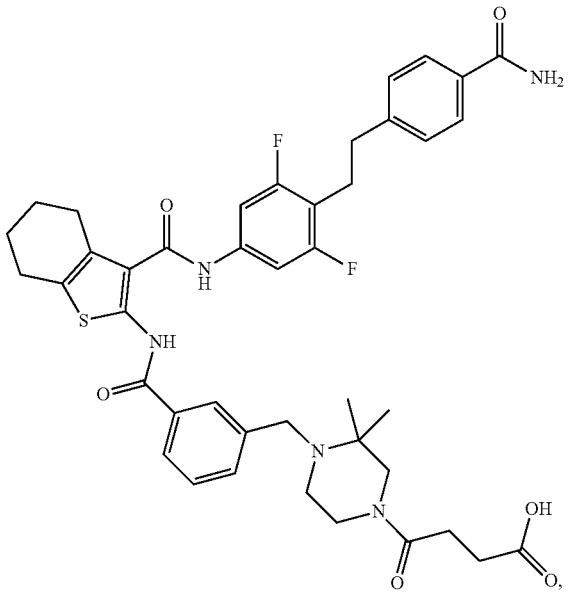 [SMILES: CC1(C)CN(C(=O)CCC(=O)O)CCN1Cc1cccc(C(=O)Nc2sc3c(c2C(=O)Nc2cc(F)c(CCc4ccc(C(N)=O)cc4)c(F)c2)CCCC3)c1]

or a pharmaceutically acceptable salt thereof.

14. A compound of claim 1, or a pharmaceutically acceptable salt thereof, selected from the group consisting of:

4-[2-[2,6-difluoro-4-[[2-[[3-[(2,2,4-trimethylpiperazin-1-yl)methyl]benzoyl]amino]-4,5,6,7-tetrahydrobenzothiophene-3-carbonyl]amino]phenyl]ethyl]benzoic acid formic acid salt;

4-[2-[4-[[2-[[2,2-dimethyl-4-(methylcarbamoyl)piperazin-1-yl]methyl]benzoyl]amino]-4,5,6,7-tetrahydrobenzothiophene-3-carbonyl]amino]-2,6-difluoro-phenyl]ethyl]benzoic acid;

4-[2-[4-[[2-[[3-[[2,2-dimethyl-4-(methylcarbamothioyl)piperazin-1-yl]methyl]benzoyl]amino]-4,5,6,7-tetrahydrobenzothiophene-3-carbonyl]amino]-2,6-difluoro-phenyl]ethyl]benzoic acid;

4-[2-[4-[[2-[[3-[[4-(2-carboxyethylcarbamoyl)-2,2-dimethyl-piperazin-1-yl]methyl]benzoyl]amino]-4,5,6,7-tetrahydrobenzothiophene-3-carbonyl]amino]-2,6-difluoro-phenyl]ethyl]benzoic acid;

4-[2-[2,6-difluoro-4-[[2-[[3-[[8-(methylcarbamoyl)-3,8-diazabicyclo[3.2.1]octan-3-yl]methyl]benzoyl]amino]benzothiophene-3-carbonyl]amino]phenyl]ethyl]benzoic acid, formic acid salt;

4-[4-[2,6-difluoro-4-[[2-[[3-[(4-methoxycarbonyl-2,2-dimethyl-piperazin-1-yl)methyl]benzoyl]amino]-4,5,6,7-tetrahydrobenzothiophene-3-carbonyl]amino]phenyl]ethyl]benzoic acid;

4-(2,6-difluoro-4-(2-(3-(((1R,5S)-8-pentanoyl-3,8-diazabicyclo[3.2.1]octan-3-yl)methyl)benzamido)-4,5,6,7-tetrahydrobenzo[b]thiophene-3-carboxamido)phenethyl)benzoic acid;

4-[2-[4-[[2-[[3-[[2,2-dimethyl-4-(methylsulfamoyl)piperazin-1-yl]methyl]benzoyl]amino]-4,5,6,7-tetrahydrobenzothiophene-3-carbonyl]amino]-2,6-difluoro-phenyl]ethyl]benzoic acid;

4-[2-[2,6-difluoro-4-[[2-[[3-[[8-(tetrahydropyran-4-ylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoic acid;

4-[2-[4-[[2-[[3-[(8-acetyl-3,8-diazabicyclo[3.2.1]octan-3-yl)methyl]benzoyl]amino]-4,5,6,7-tetrahydrobenzothiophene-3-carbonyl]amino]-2,6-difluoro-phenyl]ethyl]benzoate;

4-[2-[2,6-difluoro-4-[[2-[[3-[[8-(2-methoxyethylsulfonyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate;

4-[2-[2,6-difluoro-4-[[2-[[3-[[8-(2-methoxyethylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate;

4-[2-[2,6-difluoro-4-[[2-[[3-[[8-(4-methoxybutylcarbamoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate;

4-[2-[4-[[2-[[3-[[8-[bis(2-methoxyethyl)carbamoyl]-3,8-diazabicyclo[3.2.1]octan-3-yl]methyl]benzoyl]amino]-4,5,6,7-tetrahydrobenzothiophene-3-carbonyl]amino]-2,6-difluoro-phenyl]ethyl]benzoate;

4-[2-[2,6-difluoro-4-[[2-[[3-[[8-(2-methylpropanoyl)-3,8-diazabicyclo[3.2.1]octan-3-yl]methyl]benzoyl]amino]-4,5,6,7-tetrahydrobenzothiophene-3-carbonyl]amino]phenyl]ethyl]benzoate;

4-[2-[4-[[2-[[3-[[8-[2-(dimethylamino)acetyl]-3,8-diazabicyclo[3.2.1]octan-3-yl]methyl]benzoyl]amino]-4,5,6,7-tetrahydrobenzothiophene-3-carbonyl]amino]-2,6-difluoro-phenyl]ethyl]benzoic acid;

4-[2-[2,6-difluoro-4-[[2-[[3-[[8-[1-(methoxymethyl)cyclopropanecarbonyl]-3,8-diazabicyclo[3.2.1]octan-3-yl]methyl]benzoyl]amino]-4,5,6,7-tetrahydrobenzothiophene-3-carbonyl]amino]phenyl]ethyl]benzoic acid;

4-[2-[2,6-difluoro-4-[[2-[[3-[[8-[2-(4-methylpiperazin-1-yl)acetyl]-3,8-diazabicyclo[3.2.1]octan-3-yl]methyl]benzoyl]amino]-4,5,6,7-tetrahydrobenzothiophene-3-carbonyl]amino]phenyl]ethyl]benzoic acid;

4-[2-[2,6-difluoro-4-[[2-[[3-[[4-(4-hydroxybutylcarbamoyl)-2,2-dimethyl-piperazin-1-yl]methyl]benzoyl]amino]benzothiophene-3-carbonyl]amino]phenyl]ethyl]benzoic acid; and 4-[2-[4-[[2-[[3-[(4-acetyl-2,2-dimethyl-piperazin-1-yl)methyl]benzoyl]amino]-4,5,6,7-tetrahydrobenzothiophene-3-carbonyl]amino]-2,6-difluoro-phenyl]ethyl]benzoic acid.

15. The compound of claim 6 which is 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium.

16. A pharmaceutical composition comprising a compound or salt according to claim 1, and a pharmaceutically acceptable carrier, diluent or excipient.

17. A solid dispersion formulation comprising 30% of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium and 70% polyvinylpyrrolidone-vinyl acetate.

18. A method of treating hyperphosphatemia comprising administrating to a patient in need thereof an effective amount of a compound or salt according to claim 1.

19. A method of treating chronic kidney disease comprising administrating to a patient in need thereof an effective amount of a compound or salt according to claim 1.

20. A method of treating cardiovascular disease associated with chronic kidney disease comprising administrating to a patient in need thereof an effective amount of a compound or salt according to claim 1.

21. A method of treating cardiovascular disease associated with chronic kidney disease comprising administrating to a patient in need thereof an effective amount of 4-[2-[2,6-difluoro-4-[[2-[[3-[[4-(4-hydroxybutylcarbamoyl)-2,2-dimethyl-piperazin-1-yl]methyl]benzoyl]amino]-4,5,6,7-tetrahydrobenzothiophene-3-carbonyl]amino]phenyl]ethyl]benzoic acid, disodium.

* * * * *